US010940207B2

(12) United States Patent
DeRosa et al.

(10) Patent No.: US 10,940,207 B2
(45) Date of Patent: Mar. 9, 2021

(54) ICE-BASED LIPID NANOPARTICLE FORMULATION FOR DELIVERY OF MRNA

(71) Applicant: Translate Bio, Inc., Lexington, MA (US)

(72) Inventors: Frank DeRosa, Lexington, MA (US); Michael Heartlein, Lexington, MA (US); Shrirang Karve, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 16/773,638

(22) Filed: Jan. 27, 2020

(65) Prior Publication Data

US 2020/0155691 A1 May 21, 2020

Related U.S. Application Data

(62) Division of application No. 16/599,928, filed on Oct. 11, 2019, which is a division of application No. 15/809,605, filed on Nov. 10, 2017, now Pat. No. 10,471,153.

(60) Provisional application No. 62/420,421, filed on Nov. 10, 2016, provisional application No. 62/420,428, filed on Nov. 10, 2016, provisional application No. 62/421,021, filed on Nov. 11, 2016, provisional application No. 62/421,007, filed on Nov. 11, 2016, provisional application No. 62/464,330, filed on Feb. 27, 2017, provisional application No. 62/464,327, filed on Feb. 27, 2017.

(51) Int. Cl.

| | |
|---|---|
| ***A61K 47/54*** | (2017.01) |
| ***A61K 38/17*** | (2006.01) |
| ***A61K 47/28*** | (2006.01) |
| ***A61K 47/60*** | (2017.01) |
| ***A61K 47/69*** | (2017.01) |
| ***A61K 48/00*** | (2006.01) |
| ***A61K 9/00*** | (2006.01) |
| ***A61K 9/127*** | (2006.01) |
| ***A61P 11/12*** | (2006.01) |

(52) U.S. Cl.

CPC .......... *A61K 47/554* (2017.08); *A61K 9/0078* (2013.01); *A61K 9/1272* (2013.01); *A61K 38/1709* (2013.01); *A61K 47/28* (2013.01); *A61K 47/543* (2017.08); *A61K 47/60* (2017.08); *A61K 47/6911* (2017.08); *A61K 48/0008* (2013.01); *A61K 48/0033* (2013.01); *A61K 48/0041* (2013.01); *A61K 48/0066* (2013.01); *A61K 48/0075* (2013.01); *A61P 11/12* (2018.01)

(58) Field of Classification Search

None

See application file for complete search history.

(56) References Cited

U.S. PATENT DOCUMENTS

| | | | | |
|---|---|---|---|---|
| 6,375,980 | B1 | 4/2002 | Densmore, Jr. et al. | |
| 9,181,321 | B2 | 11/2015 | Heartlein et al. | |
| 10,143,758 | B2 | 12/2018 | Guild et al. | |
| 10,471,153 | B2 | 11/2019 | DeRosa et al. | |
| 2013/0195967 | A1 * | 8/2013 | Guild ..................... | C12N 15/67 424/450 |
| 2016/0151409 | A1 | 6/2016 | DeRosa et al. | |
| 2018/0161451 | A1 | 1/2018 | Fotin-Mleczek et al. | |
| 2020/0038515 | A1 | 2/2020 | DeRosa et al. | |

FOREIGN PATENT DOCUMENTS

| | | | |
|---|---|---|---|
| EP | 0814777 | A1 | 7/1998 |
| WO | WO 2014/153052 | A2 | 9/2014 |
| WO | WO 20109/207060 | A1 | 10/2019 |

OTHER PUBLICATIONS

Monnard, et ao. (1997) "Entrapment of nucleic acids in liposomes", Biochimica et Biophysica Acta, 1329: 39-50. (Year: 1997).*

Edwards, et al. (2007) "DNA-Oligonucleotide Encapsulating Liposomes as a Secondary Signal Amplification Means", Analytical Chemistry, 79: 1806-15. (Year: 2007).*

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).

Robinson et al., "Lipid Nanoparticle-Delivered Chemically Modified mRNA Restores Chloride Secretion in Cystic Fibrosis", Molecular Therapy, 26(8): 1-13 (2018).

Ruiz et al., "A clinical inflammatory syndrome attributable to aerosolized lipid-DNA administration in cystic fibrosis", Hum Gene Therapy, 12(7): 751-61 (2001).

International Search Report and Written Opinion for PCT/US17/61100 (dated Mar. 5, 2018).

* cited by examiner

*Primary Examiner* — Robert M Kelly

(74) *Attorney, Agent, or Firm* — Proskauer Rose LLP; Fangli Chen; Sang-Ah Kim

(57) ABSTRACT

The present invention provides, among other things, compositions and methods of formulating nucleic acid-containing nanoparticles comprising no more than three distinct lipids components, one distinct lipid component being a sterol-based cationic lipid. In some embodiments, the present invention provides compositions and methods in which the lipid nanoparticles further comprise helper lipids and PEG-modified lipids. The resulting formulation comprises a high encapsulation percentage for nucleic acids.

16 Claims, 16 Drawing Sheets

Specification includes a Sequence Listing.

ICE-BASED LIPID NANOPARTICLE FORMULATION FOR DELIVERY OF MRNA

RELATED APPLICATIONS

This application is a divisional application of U.S. application Ser. No. 16/599,928 filed on Oct. 11, 2019, which is a divisional application of U.S. application Ser. No. 15/809,605 filed on Nov. 10, 2017, now U.S. Pat. No. 10,471,153, which claims priority to U.S. Provisional Application Ser. No. 62/420,421, filed Nov. 10, 2016, U.S. Provisional Application Ser. No. 62/420,428, filed Nov. 10, 2016, U.S. Provisional Application Ser. No. 62/421,021, filed Nov. 11, 2016, U.S. Provisional Application Ser. No. 62/421,007, filed Nov. 11, 2016, U.S. Provisional Application Ser. No. 62/464,327, filed Feb. 27, 2017, and U.S. Provisional Application Ser. No. 62/464,330, filed Feb. 27, 2017, the disclosures of which are hereby incorporated by reference.

SEQUENCE LISTING

The present specification makes reference to a Sequence Listing (submitted electronically as a .txt file named "MRT-1247US3_SL" on Jan. 27, 2020). The .txt file was generated Jan. 27, 2020 and is 57,495 bytes in size. The entire contents of the Sequence Listing are herein incorporated by reference.

BACKGROUND

Nucleic acid-based technologies are increasingly important for various therapeutic applications including, but not limited to, messenger RNA therapy. Efforts to deliver nucleic acids have included the creation of compositions formulated to protect nucleic acids from degradation when delivered in vivo. One type of delivery vehicle for nucleic acids has been lipid nanoparticles. Important parameters to consider for the successful use of lipid nanoparticles as a delivery vehicle include lipid nanoparticle formation, physical properties of lipid components, nucleic acid encapsulation efficiencies, in vivo nucleic acid release potential, and lipid nanoparticle toxicity.

SUMMARY OF THE INVENTION

This present invention offers a unique solution wherein sterol-based cationic lipid, helper lipid and PEG-modified lipid form a lipid nanoparticle formulation of RNA. This inventive three lipid component system upon formulation shows high RNA encapsulation efficiencies and successful efficacious delivery in vivo, particularly pulmonary delivery. Such formulation systems offer additional advantages of lower lipid load (compared to other conventional four lipid component systems) and higher tolerability/lower toxicity as the metabolized products of the cationic lipid (cholesterol derivative lipid) is cholesterol.

The invention is based, in part, on the surprising discovery that a three lipid component system based on sterol-based cationic lipids is unexpectedly effective in delivering mRNA and producing encoded protein or peptide in vivo, particularly in the lung. Indeed, prior to the present invention, cationic lipids have been extensively explored as an important component of liposomes used to encapsulate nucleic acids, including mRNA, for in vivo delivery. Due to the uniquely fragile and long structure of mRNA and the complicated in vivo translation process, cationic lipids used in the liposomes typically play two roles. First, cationic lipids promote interaction with negatively charged mRNA during encapsulation, circulation and endocytosis, thereby capturing and protecting the mRNA. Then, once inside cytosol, cationic lipids need to be able to release the mRNA so that the mRNA can be translated to produce the encoded protein or peptide. Some cationic lipids, in particular, known as titratable cationic lipids, are particularly effective in delivering mRNA. Surprisingly, the present inventors found that liposomes comprising the sterol-based cationic lipids described herein can have an even higher encapsulation percentage for mRNA and can be even more effective in delivering various mRNA in vivo. Particularly, liposomes comprising the sterol-based cationic lipids described herein can be incredibly effective for pulmonary delivery of mRNA, and surprisingly successful for delivering mRNA via nebulization. Thus, the present inventors have demonstrated that the three lipid component system can be uniquely useful in delivering mRNA for highly efficient and sustained production of protein or peptide (e.g., therapeutic protein) in vivo, particularly in the pulmonary system. The present invention therefore permits an improved mRNA therapy that can significantly reduce the required amount of mRNA and associated lipids, administration frequency, and possible side effects, providing safer, more potent, and patient friendly mRNA therapy for various diseases.

In one aspect, the present invention provides methods of delivering nucleic acids in vivo comprising administering by pulmonary delivery to a subject in need of delivery a composition comprising nucleic acids; and lipid nanoparticles encapsulating the nucleic acids, wherein each individual lipid nanoparticle comprises no more than three distinct lipid components, one distinct lipid component being a sterol-based cationic lipid.

In another aspect, the present invention provides methods of delivering nucleic acids in vivo comprising administering by pulmonary delivery to a subject in need of delivery a composition comprising nucleic acids, wherein the nucleic acids encode a Cystic Fibrosis Transmembrane Conductance Regulator (CFTR) protein; and lipid nanoparticles encapsulating the nucleic acids, wherein each individual lipid nanoparticle comprises no more than three distinct lipid components, one distinct lipid component being a sterol-based cationic lipid.

In some embodiments, the pulmonary delivery comprises nebulization. In some embodiments, said subject is a subject in need of delivery.

In some embodiments, the lipid nanoparticles have an encapsulation percentage for nucleic acids of at least 70% (e.g., at least 75%, at least 80%, at least 85%, at least 90%, at least 95%, at least 96%, at least 97%, at least 98%, at least 99%).

In some embodiments, the three distinct lipid components comprise one or both of helper lipids and PEG-modified lipids.

In some embodiments, the sterol-based cationic lipid has a structure according to Formula (A), B-$L^1$-S (Formula A), or a protonated form thereof, wherein B is a basic functional group wherein the protonated form has a $pK_a$ that is no more than about 8.0; $L^1$ is an optionally substituted linker group that is a $C_1$-$C_{20}$ alkylene or a 2- to 20-membered heteroalkylene; and S is a sterol.

In some embodiments, B is an optionally substituted 5- or 6-membered nitrogen-containing heteroaryl. In some embodiments, B is a group selected from pyrrolyl, imidazolyl, pyrazolyl, triazolyl, tetrazolyl, pyridyl, pyrimidyl, pyrazinyl, and pyridazinyl, each of which is optionally substituted. In some embodiments, B is a group selected from pyrrolyl, pyrazolyl, triazolyl, tetrazolyl, pyridyl, pyrimidyl, pyrazinyl, and pyridazinyl, each of which is optionally substituted. In some embodiments, B is a group selected from pyrrolyl, pyrazolyl, triazolyl, tetrazolyl, pyrimidyl, pyrazinyl, and pyridazinyl, each of which is optionally substituted.

In some embodiments, $L^1$ is an optionally substituted linker group that is a $C_1$-$C_{20}$ alkylene. In some embodiments, $L^1$ is an optionally substituted linker group that is a 2- to 20-membered heteroalkylene. In some embodiments, $L^1$ is a 2- to 20-membered heteroalkylene that is non-peptidic. In some embodiments, $L^1$ comprises a moiety that is an ester group, an amide group, a carbamate group, a carbonate group, or a urea group. In some embodiments, $L^1$ comprises a moiety that is an amide group, a carbamate group, a carbonate group, or a urea group. In some embodiments, $L^1$ comprises a moiety that is an amide group, a carbonate group, or a urea group. In some embodiments, $L^1$ is $-X^1-C(X^3)-X^2$, $-(C_1$-$C_{19}$ alkylene)$-X^1-C(X^3)-X^2$, $-X^1-C(X^3)-X^2(C_1$-$C_{19}$ alkylene)-, $-(C_1$-$C_{19}$ alkylene)$-X^1-$, $-X^1-(C_1$-$C_{19}$ alkylene)-, wherein each $X^1$ and $X^2$ is independently, a covalent bond, —O—, —S—, or —NH—; $X^3$ is independently =O, =S, or =NH; and wherein said $C_1$-$C_{19}$ alkylene is optionally substituted. In some embodiments, $L^1$ does not comprise substituents having the structure $-N(R')_2$, or a positively charged form thereof, wherein each R' is independently hydrogen or optionally substituted $C_1$-$C_{20}$ alkyl.

In some embodiments, S is a zoosterol, or an oxidized or reduced form thereof. In some embodiments, S is a phytosterol, or an oxidized or reduced form thereof. In some embodiments, S is a synthetic sterol, or an oxidized or reduced form thereof. In some embodiments, S is a sterol selected from cholesterol, an oxidized form of cholesterol, a reduced form of cholesterol, alkyl lithocholate, stigmasterol, stigmastanol, campesterol, ergosterol, and sitosterol. In some embodiments, S is a sterol selected from an oxidized form of cholesterol, a reduced form of cholesterol, alkyl lithocholate, stigmasterol, stigmastanol, campesterol, ergosterol, and sitosterol. In some embodiments, S is a sterol selected from

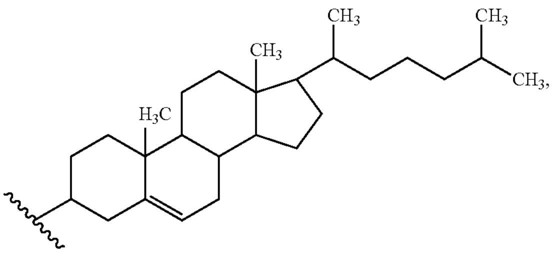

(cholesterol)

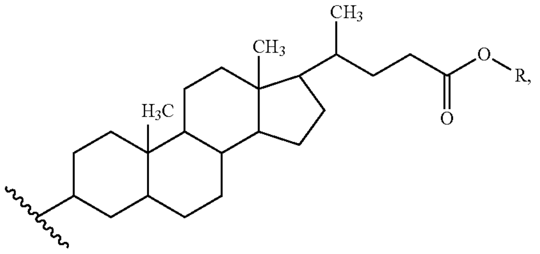

(alkyl lithocholate)

-continued

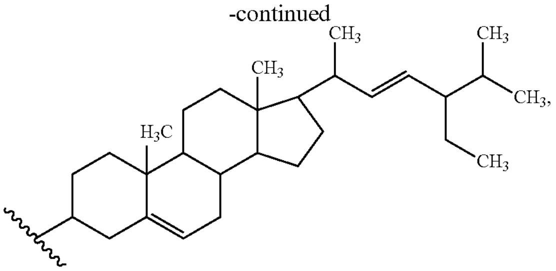

(stigmasterol)

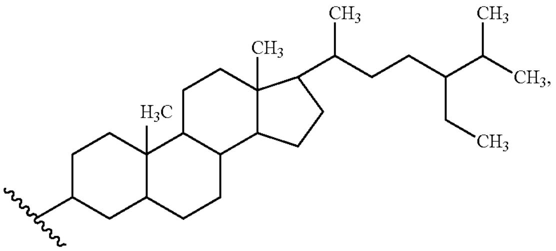

(stigmastanol)

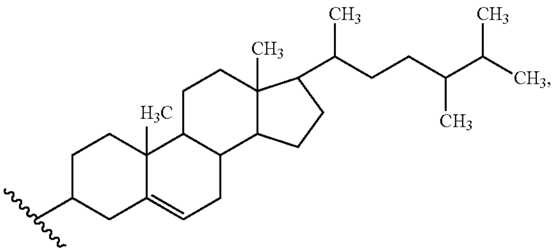

(campesterol)

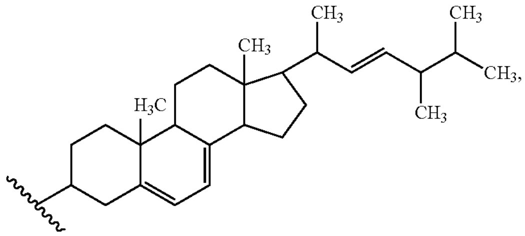

and (ergosterol)

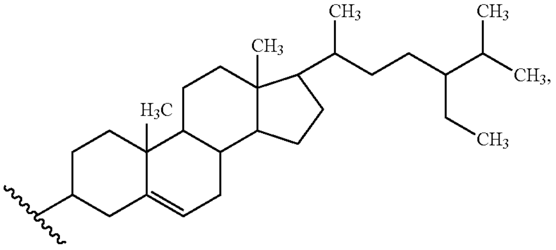

(sitosterol)

wherein R is optionally substituted $C_1$-$C_{20}$ alkyl. In some embodiments, S is a sterol selected from

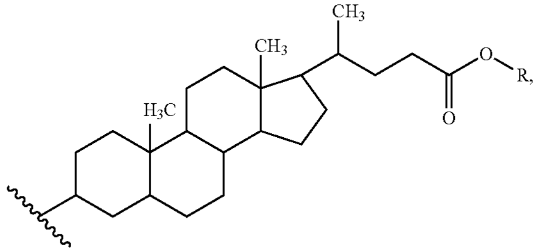

(alkyl lithocholate)

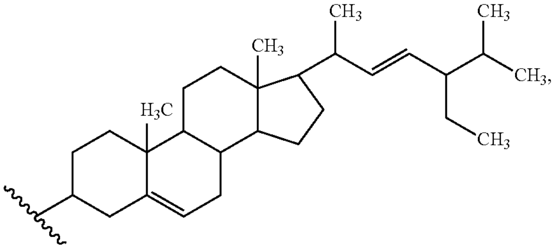

(stigmasterol)

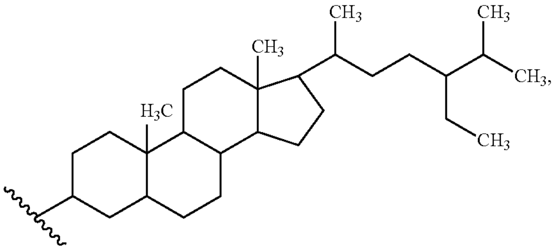

(stigmastanol)

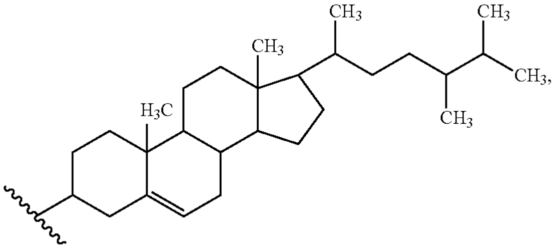

(campesterol)

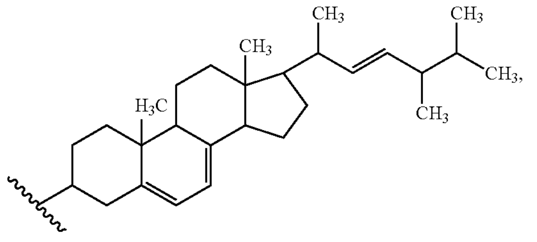

and (ergosterol)

-continued

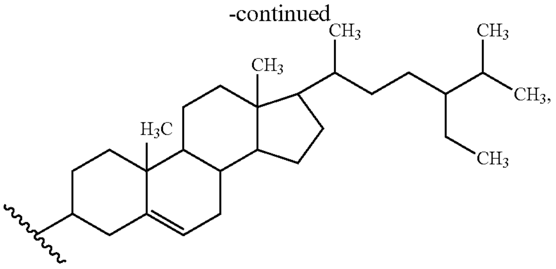

(sitosterol)

wherein R is optionally substituted $C_1$-$C_{20}$ alkyl.

In some embodiments, the sterol-based cationic lipid comprises imidazole cholesterol ester (ICE). In some embodiments, the sterol-based cationic lipid does not comprise imidazole cholesterol ester (ICE).

In some embodiments, the nucleic acids are selected from DNA, siRNA, microRNA, and/or mRNA. In some embodiments, the nucleic acids are mRNA encoding a protein or a peptide. In some embodiments, the mRNA encoding a protein or a peptide is codon-optimized. In some embodiments, the mRNA comprises one or more modified nucleotides. In some embodiments, the mRNA comprises a modification of the 5' untranslated region of said mRNA. In some embodiments, said modification of the 5' untranslated region comprises the inclusion of a Cap1 structure. In some embodiments, the mRNA comprises a modification of the 3' untranslated region of said mRNA. In some embodiments, said modification of the 3' untranslated region comprises the inclusion of a poly A tail.

In some embodiments, the lipid nanoparticles have a size less than about 100 nm, 95 nm, 90 nm, 85 nm, 80 nm, 75 nm, 70 nm, 65 nm, 60 nm, 55 nm, 50 nm, 45 nm or 40 nm.

In another aspect, the present invention provides compositions formulated for nebulization comprising nucleic acids; and lipid nanoparticles encapsulating the nucleic acids, wherein each individual lipid nanoparticle comprises no more than three distinct lipid components, one distinct lipid component being a sterol-based cationic lipid, and further wherein the lipid nanoparticles have an encapsulation percentage for nucleic acids of at least 70% (e.g., at least 75%, at least 80%, at least 85%, at least 90%, at least 95%, at least 96%, at least 97%, at least 98%, at least 99%).

In another aspect, the present invention provides compositions comprising nucleic acids; and lipid nanoparticles encapsulating the nucleic acids, wherein each individual lipid nanoparticle comprises no more than three distinct lipid components, one distinct lipid component being a sterol-based cationic lipid, and further wherein the lipid nanoparticles have an encapsulation percentage for nucleic acids of at least 70% (e.g., at least 75%, at least 80%, at least 85%, at least 90%, at least 95%, at least 96%, at least 97%, at least 98%, at least 99%).

In some embodiments, the lipid nanoparticles have an encapsulation percentage for nucleic acids of at least 85%. In some embodiments, the lipid nanoparticles have an encapsulation percentage for nucleic acids of at least 90%.

In another aspect, the present invention provides compositions comprising mRNA encoding a Cystic Fibrosis Transmembrane Conductance Regulator (CFTR) protein; and lipid nanoparticles encapsulating the mRNA, wherein each individual lipid nanoparticle comprises no more than three distinct lipid components, one distinct lipid component being a sterol-based cationic lipid, and further wherein the lipid nanoparticles have an encapsulation percentage for mRNA of at least 80%.

In some embodiments, the lipid nanoparticles have an encapsulation percentage for mRNA of at least 85% or at least 90%.

In another aspect, the present invention provides compositions comprising nucleic acids; and lipid nanoparticles encapsulating the nucleic acids, wherein each individual lipid nanoparticle comprises no more than three distinct lipid components, one distinct lipid component being a sterol-based cationic lipid, and further wherein the sterol-based cationic lipid constitutes no more than 70% of the total lipids (e.g., no more than 68%, no more than 67%, no more than 66%, no more than 65%, no more than 60%, no more than 55%, no more than 50%, no more than 45%, or no more than 40%).

In another aspect, the present invention provides compositions comprising mRNA encoding a Cystic Fibrosis Transmembrane Conductance Regulator (CFTR) protein; and lipid nanoparticles encapsulating the mRNA, wherein each individual lipid nanoparticle comprises no more than three distinct lipid components, one distinct lipid component being a sterol-based cationic lipid, and further wherein the sterol-based cationic lipid constitutes no more than 70% of the total lipids (e.g., no more than 68%, no more than 67%, no more than 66%, no more than 65%, no more than 60%, no more than 55%, no more than 50%, no more than 45%, or no more than 40%).

In some embodiments, the sterol-based cationic lipid constitutes no more than 65% of the total lipids. In some embodiments, the sterol-based cationic lipid constitutes no more than 60% of the total lipids. In some embodiments, the three distinct lipid components comprise one or both of helper lipids and PEG-modified lipids.

In some embodiments, the sterol-based cationic lipid has a structure according to Formula (A), $B\text{-}L^1\text{-}S$ (Formula A), or a protonated form thereof, wherein B is a basic functional group wherein the protonated form has a $pK_a$ that is no more than about 8.0; $L^1$ is an optionally substituted linker group that is a $C_1$-$C_{20}$ alkylene or a 2- to 20-membered heteroalkylene; and S is a sterol.

In some embodiments, B is an optionally substituted 5- or 6-membered nitrogen-containing heteroaryl. In some embodiments, B is a group selected from pyrrolyl, imidazolyl, pyrazolyl, triazolyl, tetrazolyl, pyridyl, pyrimidyl, pyrazinyl, and pyridazinyl, each of which is optionally substituted. In some embodiments, B is a group selected from pyrrolyl, pyrazolyl, triazolyl, tetrazolyl, pyridyl, pyrimidyl, pyrazinyl, and pyridazinyl, each of which is optionally substituted. In some embodiments, B is a group selected from pyrrolyl, pyrazolyl, triazolyl, tetrazolyl, pyrimidyl, pyrazinyl, and pyridazinyl, each of which is optionally substituted.

In some embodiments, $L^1$ is an optionally substituted linker group that is a $C_1$-$C_{20}$ alkylene. In some embodiments, $L^1$ is an optionally substituted linker group that is a 2- to 20-membered heteroalkylene. In some embodiments, $L^1$ is a 2- to 20-membered heteroalkylene that is non-peptidic. In some embodiments, $L^1$ comprises a moiety that is an ester group, an amide group, a carbamate group, a carbonate group, or a urea group. In some embodiments, $L^1$ comprises a moiety that is an amide group, a carbamate group, a carbonate group, or a urea group. In some embodiments, $L^1$ comprises a moiety that is an amide group, a carbonate group, or a urea group. In some embodiments, $L^1$ is $-X^1-C(X^3)-X^2$, $-(C_1\text{-}C_{19}\text{ alkylene})\text{-}X^1-C(X^3)-X^2$, $-X^1-C(X^3)-X^2(C_1\text{-}C_{19}\text{ alkylene})\text{-}$, $-(C_1\text{-}C_{19}\text{ alkylene})\text{-}X^1-$, $-X^1-(C_1\text{-}C_{19}\text{ alkylene})\text{-}$, wherein each $X^1$ and $X^2$ is independently, a covalent bond, $-O-$, $-S-$, or $-NH-$; $X^3$ is independently $=O$, $=S$, or $=NH$; and wherein said $C_1$-$C_{19}$ alkylene is optionally substituted. In some embodiments, $L^1$ does not comprise substituents having the structure $-N(R')_2$, or a positively charged form thereof, wherein each R' is independently hydrogen or optionally substituted $C_1$-$C_{20}$ alkyl.

In some embodiments, S is a zoosterol, or an oxidized or reduced form thereof. In some embodiments, S is a phytosterol, or an oxidized or reduced form thereof. In some embodiments, S is a synthetic sterol, or an oxidized or reduced form thereof. In some embodiments, S is a sterol selected from cholesterol, an oxidized form of cholesterol, a reduced form of cholesterol, alkyl lithocholate, stigmasterol, stigmastanol, campesterol, ergosterol, and sitosterol. In some embodiments, S is a sterol selected from an oxidized form of cholesterol, a reduced form of cholesterol, alkyl lithocholate, stigmasterol, stigmastanol, campesterol, ergosterol, and sitosterol. In some embodiments, S is a sterol selected from

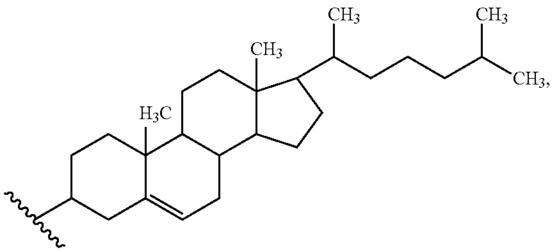

(cholesterol)

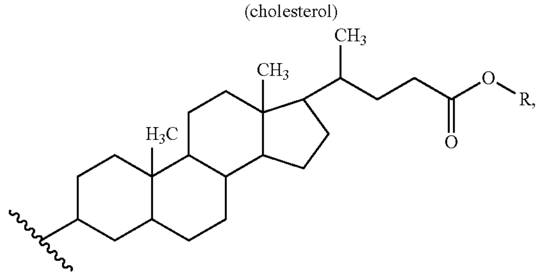

(alkyl lithocholate)

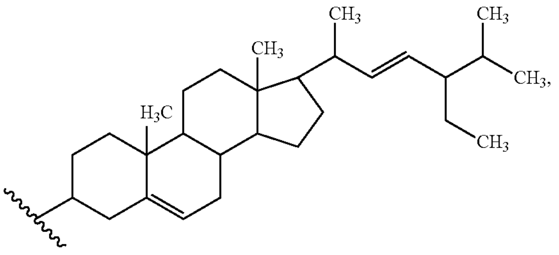

(stigmasterol)

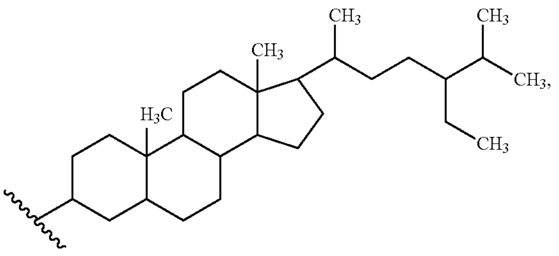

(stigmastanol)

-continued

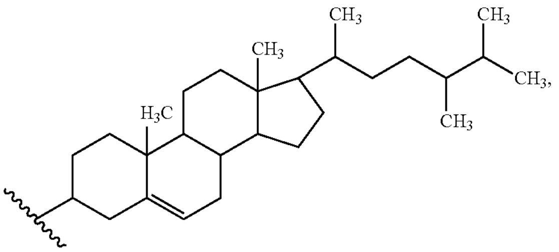

(campesterol)

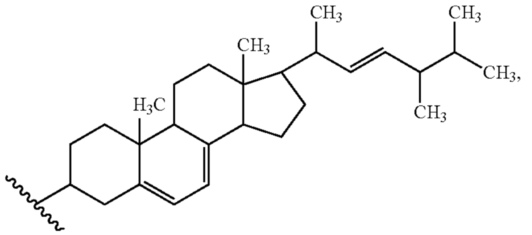

and (ergosterol)

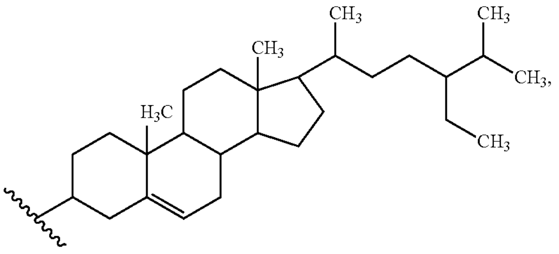

(sitosterol)

wherein R is optionally substituted $C_1$-$C_{20}$ alkyl. In some embodiments, S is a sterol selected from

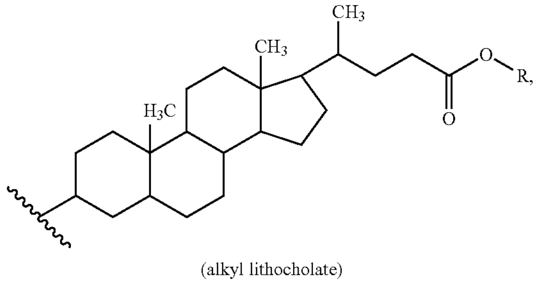

(alkyl lithocholate)

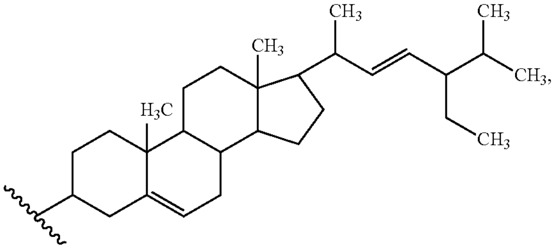

(stigmasterol)

-continued

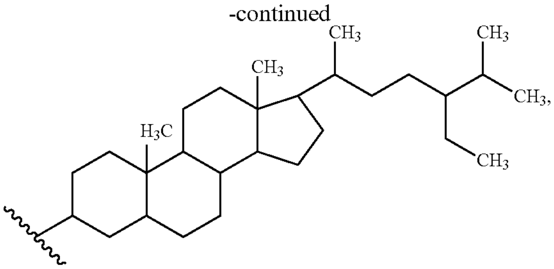

(stigmastanol)

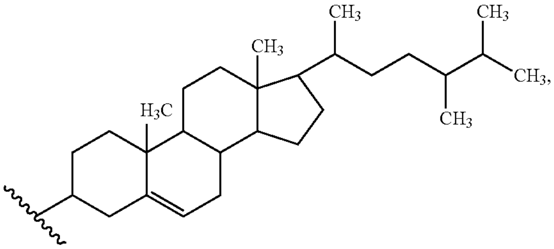

(campesterol)

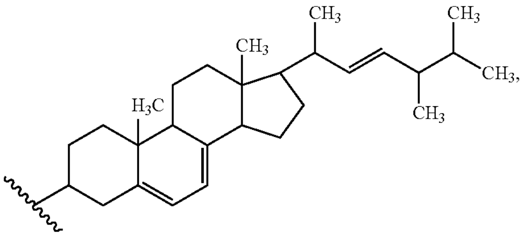

and (ergosterol)

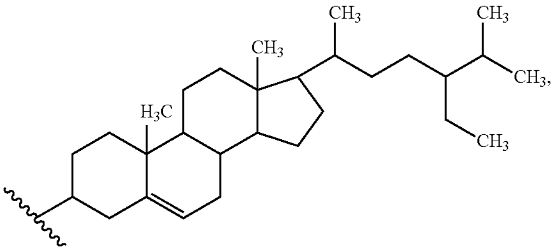

(sitosterol)

wherein R is optionally substituted $C_1$-$C_{20}$ alkyl.

In some embodiments, the sterol-based cationic lipid comprises imidazole cholesterol ester (ICE). In some embodiments, the sterol-based cationic lipid does not comprise imidazole cholesterol ester (ICE).

In some embodiments, the nucleic acids are selected from DNA, siRNA, microRNA, and/or mRNA. In some embodiments, the nucleic acids are mRNA encoding a protein or a peptide. In some embodiments, the mRNA encoding a protein or a peptide is codon-optimized. In some embodiments, the mRNA comprises one or more modified nucleotides. In some embodiments, the mRNA comprises a modification of the 5' untranslated region of said mRNA. In some embodiments, said modification of the 5' untranslated region comprises the inclusion of a Cap1 structure. In some embodiments, the mRNA comprises a modification of the 3' untranslated region of said mRNA. In some embodiments, said modification of the 3' untranslated region comprises the inclusion of a poly A tail.

In some embodiments, the lipid nanoparticle has a size less than about 100 nm, 95 nm, 90 nm, 85 nm, 80 nm, 75 nm, 70 nm, 65 nm, 60 nm, 55 nm, 50 nm, 45 nm or 40 nm.

In some embodiments, the mRNA encoding a CFTR protein comprises SEQ ID NO: 1. In some embodiments, the mRNA encoding a CFTR protein comprises a polynucleotide sequence at least 70%, 75%, 80%, 85%, 90%, or 95% identical to SEQ ID NO: 1.

In some embodiments, the lipid nanoparticle is formed by mixing an mRNA solution and a lipid solution into a 20% ethanol. In some embodiments, the lipid nanoparticles are further purified by Tangential Flow Filtration.

In another aspect, the present invention provides methods of delivering mRNA in vivo comprising administering a composition to a subject. In some embodiments, said subject is a subject in need of delivery. In some embodiments, the composition is administered intravenously. In some embodiments, the composition is administered by pulmonary delivery. In some embodiments, the pulmonary delivery comprises nebulization.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

DEFINITIONS

Figure 1:
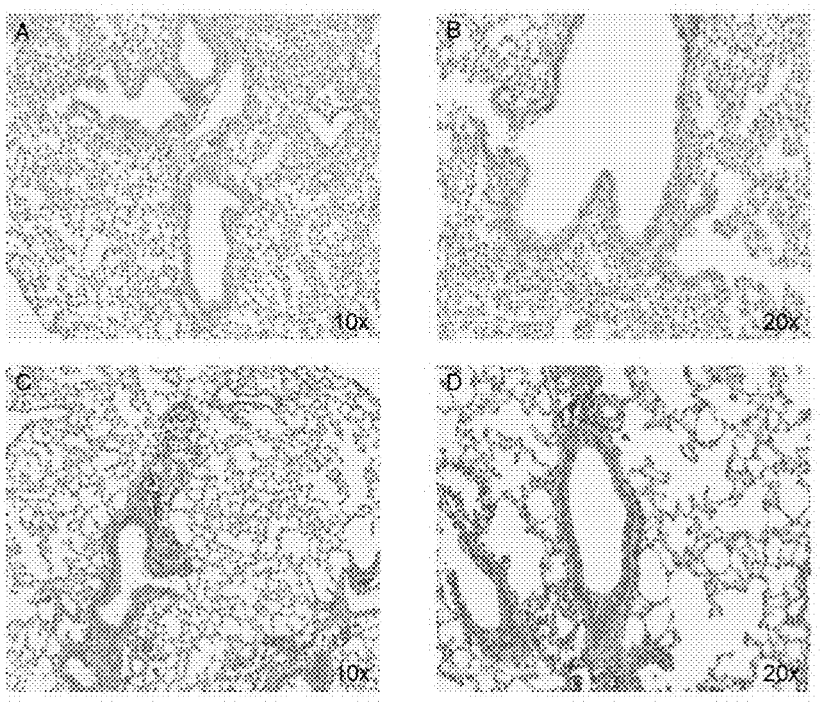
FIG. 1 depicts exemplary immunohistochemical detection of human Cystic Fibrosis Transmembrane Conductance Regulator (hCFTR) protein in mouse lung 24 hours after treatment with ICE-based LNPs encapsulating codon-optimized hCFTR mRNA, B=Untreated mouse lung at 10× & 20× magnification, respectively. C, D=CO-hCFTR mRNA ICE LNP-treated mouse lung at 10× & 20× magnification, respectively.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl (Cm), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—C(H)(R)—COHO. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Encapsulation: As used herein, the term "encapsulation," or grammatical equivalent, refers to the process of confining an mRNA molecule within a nanoparticle.

Expression: As used herein, "expression" of a nucleic acid sequence refers to translation of an mRNA into a peptide, polypeptide, or protein, assembly of multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein or peptide encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US 2012/0195936 and international publication WO 2011/012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguano sine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N\pm(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder (e.g., cystic fibrosis) but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease to be treated. In some embodiments, target tissues include those tissues that display disease-associated pathology, symptom, or feature.

Transfer vehicle: In some embodiments, the transfer vehicle is a liposomal vesicle, or other means to facilitate the transfer of a nucleic acid to target cells and tissues. Suitable transfer vehicles include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides, among other things, methods and compositions for delivering mRNA in vivo using improved liposomes incorporating a sterol-based cationic lipid, a helper lipid, and a PEG or PEG-modified lipid as described herein.

Lipid Nanoparticles

According to the present invention, suitable compositions described herein comprise nucleic acids; and lipid nanoparticles encapsulating the nucleic acids, wherein said lipid nanoparticles comprise distinct lipid components. In some embodiments, there are no more than three distinct lipid components and exemplary distinct lipid components include sterol-based cationic lipids, helper lipids (e.g., non-cationic lipids), and PEG-modified lipids.

In some embodiments, the lipid nanoparticles have an encapsulation percentage of nucleic acids that is at least about 50%, about 55%, about 60%, about 65%, about 70%, about 75%, about 80%, about 85%, about 90%, or about 95%.

In some embodiments, the percentage of lipid nanoparticles in a composition that encapsulate a nucleic acid is at least about 50%, about 55%, about 60%, about 65%, about 70%, about 75%, about 80%, about 85%, about 90%, or about 95%.

Sterol-Based Cationic Lipids

As used herein, the phrase "sterol-based lipid" or "sterol-based cationic lipid" refers to a cationic lipid comprising a steroid moiety. As used herein, the phrase "cationic lipid" refers to any of a number of lipid species that carry a net positive charge at a selected pH, such as physiological pH.

In embodiments, a sterol-based cationic lipid has a structure according to Formula (A), $B\text{-}L^1\text{-}S$ (Formula A), or a protonated form thereof.

B is a basic functional group (e.g., wherein the protonated form has a $pK_a$ that is no more than about 8.0).

$L^1$ is an optionally substituted linker group (e.g., a $C_1$-$C_{20}$ alkylene or a 2- to 20-membered heteroalkylene).

S is a sterol.

In some embodiments, B is a basic functional group wherein the protonated form has a $pK_a$ that is no more than about 9.0, about 8.5, about 8.0, about 7.5, or about 7.0. In embodiments, B is a basic functional group wherein the protonated form has a $pK_a$ that is no more than about 8.0 or about 7.5.

In some embodiments, B is a basic functional group wherein the protonated form has a $pK_a$ that is about 4.0 to about 9.0, about 4.0 to about 8.0, about 4.5 to about 8.0, about 5.0 to about 8.0, about 5.5 to about 8.0, or about 6.0 to about 8.0.

In some embodiments, B is an optionally substituted 5- or 6-membered nitrogen-containing heteroaryl.

In some embodiments, B is a group selected from pyrrolyl, imidazolyl, pyrazolyl, triazolyl, tetrazolyl, pyridyl, pyrimidyl, pyrazinyl, and pyridazinyl, each of which is optionally substituted. For any optionally substituted group described herein (e.g., a group that has 0, 1, 2, 3, or 4 independent substituent groups), exemplary substituent groups include but are not limited to: halogen (e.g., —F, —Cl, —Br, or —I), $C_{1-20}$ alkyl (e.g., a $C_{1-6}$ alkyl), $C_{1-20}$ haloalkyl (e.g., a $C_{1-6}$ haloalkyl), —CN, —OH, —O($C_{1-20}$ alkyl) (e.g., —O($C_{1-6}$ alkyl)), —O($C_{1-20}$ haloalkyl) (e.g., —O($C_{1-6}$ haloalkyl)), —$NH_2$, —NH($C_{1-6}$ alkyl), and —NH($C_{1-6}$ alkyl)$_2$.

In some embodiments, B is a group selected from pyrrolyl, pyrazolyl, triazolyl, tetrazolyl, pyridyl, pyrimidyl, pyrazinyl, and pyridazinyl, each of which is optionally substituted.

In some embodiments, B is a group selected from pyrrolyl, pyrazolyl, triazolyl, tetrazolyl, pyrimidyl, pyrazinyl, and pyridazinyl, each of which is optionally substituted.

In some embodiments, $L^1$ is a linker group that is optionally substituted $C_1$-$C_{20}$ alkylene (e.g., an optionally substituted $C_1$-$C_{10}$ alkylene or an optionally substituted $C_1$-$C_5$ alkylene). As used herein, the term "alkylene" represents a saturated divalent straight or branched chain hydrocarbon group and is exemplified by methylene, ethylene, isopropylene and the like.

In some embodiments, $L^1$ is a linker group that is optionally substituted 2- to 20-membered heteroalkylene (e.g., an optionally substituted 2- to 12-membered heteroalkylene or an optionally substituted 2- to 6-membered heteroalkylene). As used herein, the term "heteroalkylene" refers to a divalent heteroalkyl group. The term "heteroalkyl group" refers to a stable straight or branched chain hydrocarbon radical, having the stated number of atoms, wherein the atoms are selected from carbon and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group.

In some embodiments, $L^1$ is a linker group that is optionally substituted 2- to 20-membered heteroalkylene, and wherein $L^1$ is non-peptidic (that is, a non-peptidic linker $L^1$ is one that does not comprise amino acid residues).

In some embodiments, $L^1$ is a linker group that comprises a moiety that is an ester group, an amide group, a carbamate group, a carbonate group, or a urea group.

In some embodiments, $L^1$ is a linker group that comprises a moiety that is an amide group, a carbamate group, a carbonate group, or a urea group.

In some embodiments, $L^1$ is a linker group that comprises a moiety that is an amide group, a carbonate group, or a urea group.

In some embodiments, $L^1$ is a linker group represented by a formula that is: —$X^1$—C($X^3$)—$X^2$, —($C_1$-$C_{19}$ alkylene)-$X^1$—C($X^3$)—$X^2$, —$X^1$—C($X^3$)—$X^2$($C_1$-$C_{19}$ alkylene)-, —($C_1$-$C_{19}$ alkylene)-$X^1$—, —$X^1$—($C_1$-$C_{19}$ alkylene)-.

Each $X^1$ and $X^2$ is independently, a covalent bond, —O—, —S—, or —NH—.

$X^3$ is independently =O, =S, or =NH.

The $C_1$-$C_{19}$ alkylene group (e.g., a $C_1$-$C_5$ alkylene or a $C_1$-$C_{10}$ alkylene group) is independently optionally substituted.

In some embodiments, $L^1$ is unsubstituted.

In some embodiments, $L^1$ does not comprise substituents having the structure —N(R')$_2$, or a positively charged form thereof, wherein each R' is independently hydrogen or optionally substituted $C_1$-$C_{20}$ alkyl.

In some embodiments, S is a zoosterol, or an oxidized or reduced form thereof. In embodiments, S is a zoosterol. In embodiments, S is an oxidized form of a zoosterol. In embodiments, S is a reduced form of a zoosterol.

In some embodiments, S is a phytosterol, or an oxidized or reduced form thereof. In embodiments, S is a phytosterol. In embodiments, S is an oxidized form of a phytosterol. In embodiments, S is a reduced form of a phytosterol.

In some embodiments, S is a synthetic sterol (e.g., non-naturally occurring), or an oxidized or reduced form thereof. In embodiments, S is a synthetic sterol. In embodiments, S is an oxidized form of a synthetic sterol. In embodiments, S is a reduced form of a synthetic sterol.

In some embodiments, S is an oxidized form of a sterol as described herein.

In some embodiments, an oxidized form of a sterol is one in which the parent sterol has been modified to include further oxygen-containing groups. In embodiments, an oxidized form of a sterol includes one or more (e.g., 1, 2, 3, or 4) additional hydroxyl groups and/or carbonyl-containing groups (e.g., a ketone, an aldehyde, a carboxylic acid, or a carboxylic ester moiety) as compared to the parent sterol.

In some embodiments, an oxidized form of a sterol is one in which the parent sterol has been modified to include unsaturated carbon-carbon bonds (e.g., carbon-carbon double bonds). In embodiments, an oxidized form of a sterol includes one or more (e.g., 1, 2, or 3) additional carbon-carbon double bonds as compared to the parent sterol.

In some embodiments, S is a reduced form of a sterol as described herein.

In some embodiments, a reduced form of a sterol is one in which the parent sterol has been modified to include fewer oxygen-containing groups. In embodiments, a reduced form of a sterol includes a reduced number (e.g., 1, 2, 3, or 4 fewer moieties) of hydroxyl groups and/or carbonyl-containing groups (e.g., a ketone, an aldehyde, a carboxylic acid, or a carboxylic ester moiety) as compared to the parent sterol.

In some embodiments, a reduced form of a sterol is one in which the parent sterol has been modified to include fewer unsaturated carbon-carbon bonds (e.g., carbon-carbon double bonds). In embodiments, a reduced form of a sterol includes a reduced number (e.g., 1, 2, or 3 fewer) of carbon-carbon double bonds as compared to the parent sterol.

In some embodiments, S is a sterol that is cholesterol, alkyl lithocholate, stigmasterol, stigmastanol, campesterol, ergosterol, or sitosterol, or any oxidized or reduced form thereof.

In some embodiments, S is a sterol selected from cholesterol, an oxidized form of cholesterol, a reduced form of cholesterol, alkyl lithocholate, stigmasterol, stigmastanol, campesterol, ergosterol, and sitosterol.

In some embodiments, S is a sterol selected from an oxidized form of cholesterol, a reduced form of cholesterol, alkyl lithocholate, stigmasterol, stigmastanol, campesterol, ergosterol, and sitosterol.

In some embodiments, S is a sterol that is cholesterol, alkyl lithocholate, stigmasterol, stigmastanol, campesterol, ergosterol, or sitosterol.

In some embodiments, S is a sterol that is an oxidized form of: cholesterol, alkyl lithocholate, stigmasterol, stigmastanol, campesterol, ergosterol, or sitosterol.

In some embodiments, S is a sterol that is a reduced form of: cholesterol, alkyl lithocholate, stigmasterol, stigmastanol, campesterol, ergosterol, or sitosterol.

In some embodiments, S is a sterol that is cholesterol, an oxidized form of cholesterol, or a reduced form of cholesterol.

In some embodiments, S is a sterol that is alkyl lithocholate, an oxidized form of alkyl lithocholate, or a reduced form of alkyl lithocholate.

In some embodiments, S is a sterol that is stigmasterol, an oxidized form of stigmasterol, or a reduced form of stigmasterol.

In some embodiments, S is a sterol that is stigmastanol, an oxidized form of stigmastanol, or a reduced form of stigmastanol.

In some embodiments, S is a sterol that is campesterol, an oxidized form of campesterol, or a reduced form of campesterol.

In some embodiments, S is a sterol that is ergosterol, an oxidized form of ergosterol, or a reduced form of ergosterol.

In some embodiments, S is a sterol that is sitosterol, an oxidized form of sitosterol, or a reduced form of sitosterol.

In some embodiments, S is a sterol that is a bile acid or an alkyl ester thereof, or an oxidized form thereof, or a reduced form thereof.

In some embodiments, S is a sterol that is cholic acid or an alkyl ester thereof, or an oxidized form thereof, or a reduced form thereof.

In some embodiments, S is a sterol selected from

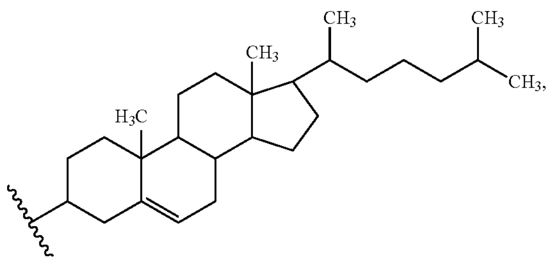

(cholesterol)

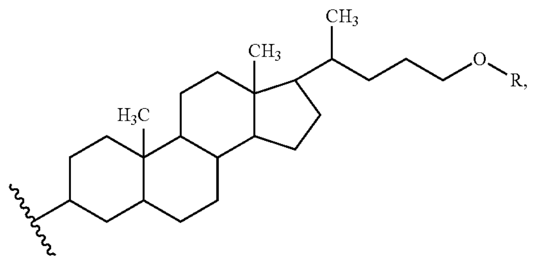

(alkyl lithocholate)

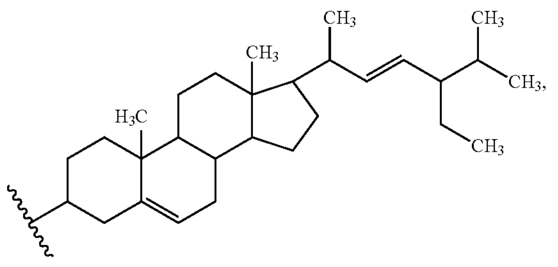

(stigmasterol)

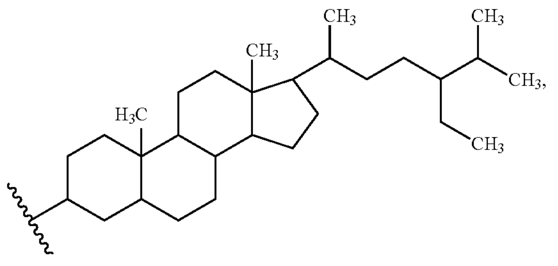

(stigmastanol)

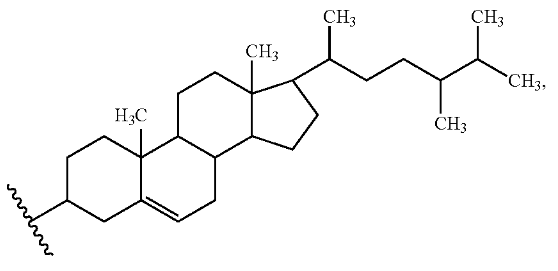

(campesterol)

-continued

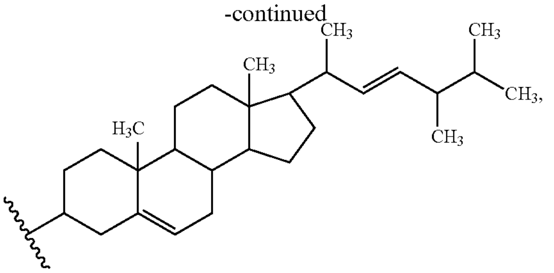

(ergosterol)

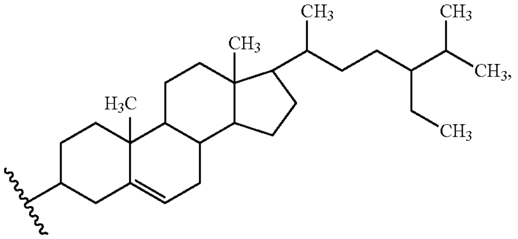

and (sitosterol)

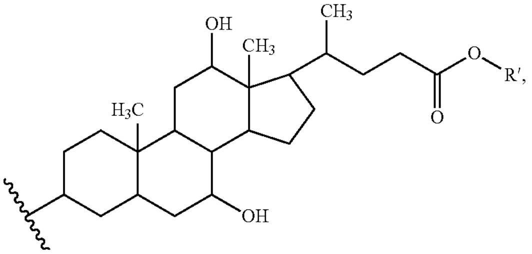

(cholic acid)

wherein R is optionally substituted $C_1$-$C_{20}$ alkyl, and R' is H or optionally substituted $C_1$-$C_{20}$ alkyl.

In some embodiments, S is a sterol that is

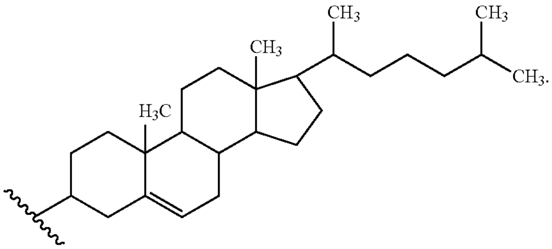

(cholesterol)

In some embodiments, S is a sterol selected from

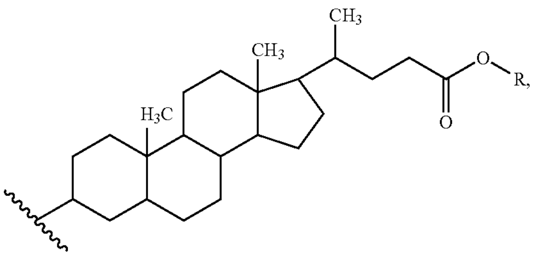

(alkyl lithocholate)

-continued

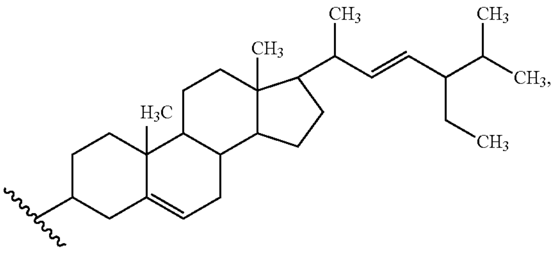

(stigmasterol)

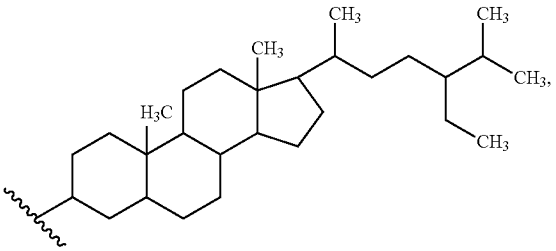

(stigmastanol)

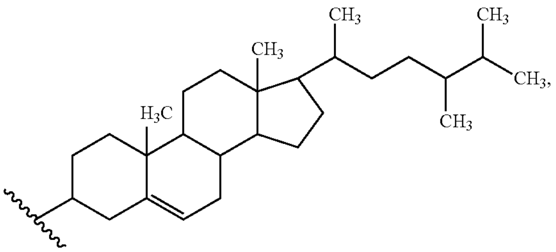

(campesterol)

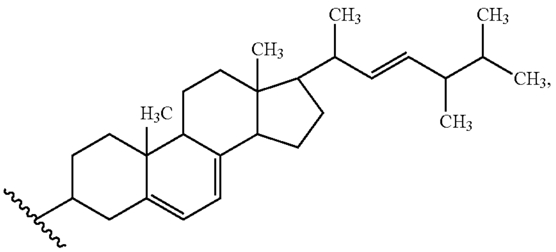

(ergosterol)

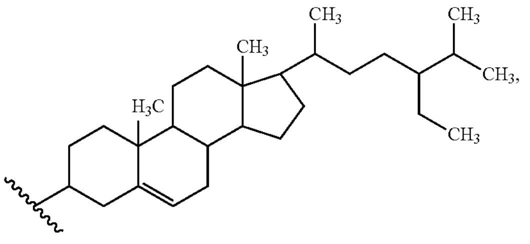

and (sitosterol)

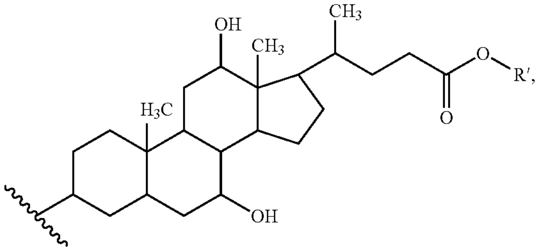

(cholic acid)

wherein R is optionally substituted $C_1$-$C_{20}$ alkyl, and R' is H or optionally substituted $C_1$-$C_{20}$ alkyl.

In some embodiments, a sterol-based cationic lipid comprises imidazole cholesterol ester (ICE).

In some embodiments, a sterol-based cationic lipid does not comprise imidazole cholesterol ester (ICE).

In some embodiments, a sterol-based cationic lipid is a cholesterol-based cationic lipid. Such cholesterol-based cationic lipids can be used, either alone or in combination with other lipids as described herein. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

(I)

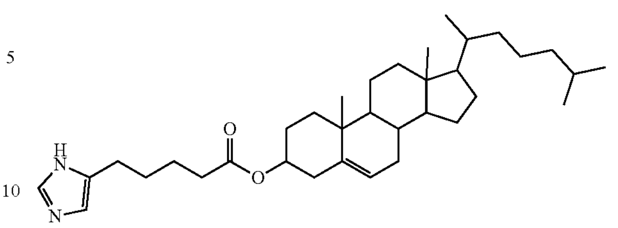

An exemplary hydrolysis reaction of structure (I) is provided in Scheme 1.

Scheme 1

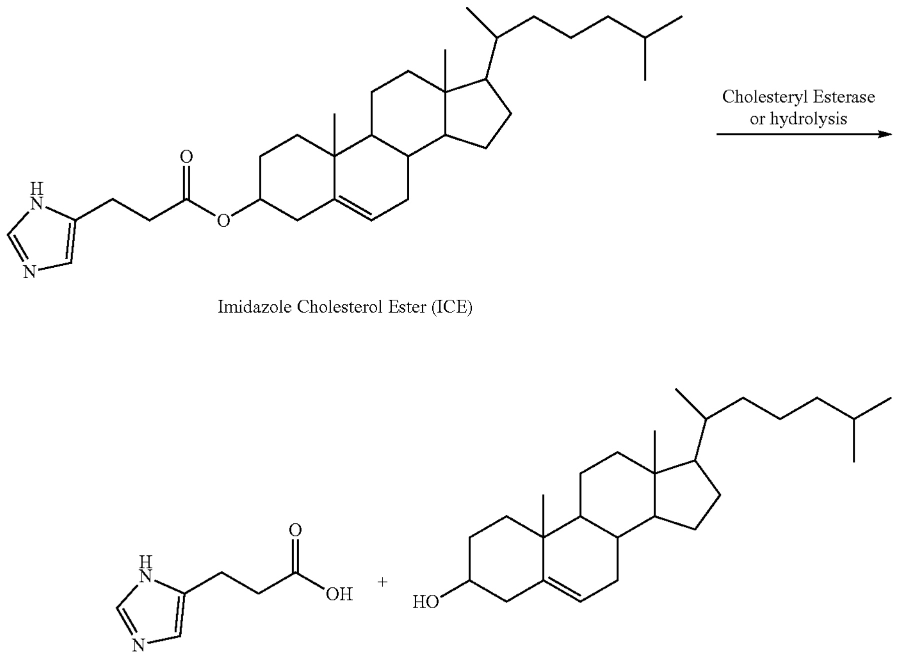

In embodiments, sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I).

Without wishing to be bound by a particular theory, it is believed that the fusogenicity of the imidazole-based cationic lipid ICE is related to the endosomal disruption which is facilitated by the imidazole group, which has a lower pKa relative to traditional cationic lipids. The endosomal disruption in turn promotes osmotic swelling and the disruption of the liposomal membrane, followed by the transfection or intracellular release of the polynucleotide contents loaded or encapsulated therein into the target cell.

The imidazole-based cationic lipids are also characterized by their reduced toxicity relative to other cationic lipids. In some embodiments, one or more of the lipid nanoparticles which comprises the blended pharmaceutical composition comprise an imidazole-based cationic lipid such as ICE, to reduce the relative concentration of other more toxic cationic lipids in such blended pharmaceutical composition. The imidazole-based cationic lipids (e.g., ICE) may be used as the sole cationic lipid in one or more of the lipid nanoparticles that comprise the blended formulations, or alternatively may be combined with traditional cationic lipids (e.g., DOPE, DC-Chol), non-cationic lipids, PEG-modified lipids and/or helper lipids. The cationic lipid may comprise a molar ratio of about 1% to about 90%, about 2% to about 90%, about 5% to about 90%, about 10% to about 90%, about 15% to about 90%, about 20% to about 90%, about 30% to about 90%, about 40% to about 90%, about 50% to about 90%, about 60% to about 90%, about 70% to about 90%, about 80% to about 90%, about 1% to about 80%, about 1% to about 70%, about 1% to about 60%, about 1% to about 50%, about 1% to about 40%, about 1% to about 30%, about 1% to about 20%, about 1% to about 15%, about 1% to about 10%, about 2% to about 70%, about 5% to about 50%, about 10% to about 40% of the total lipid present in the lipid nanoparticle, or preferably about 20% to about 70% of the total lipid present in the lipid nanoparticle.

Ratio of Distinct Lipid Components

In embodiments where a lipid nanoparticle comprises three and no more than three distinct lipid components, the ratio of total lipid content (i.e., the ratio of lipid component (1):lipid component (2):lipid component (3)) can be represented as x:y:z, wherein $$(y+z)=100-x.$$

In some embodiments, each of "x," "y," and "z" represents molar percentages of the three distinct lipid components, and the ratio is a molar ratio.

In some embodiments, each of "x," "y," and "z" represents weight percentages of the three distinct lipid components, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z", is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In some embodiments, variable "x" is no more than about 65%, about 60%, about 55%, about 50%, or about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%.

In some embodiments, variable "z," representing the molar percentage of lipid component (3) (e.g., a PEG-modified lipid) is no more than about 1%, 2%, 3%, 4%, 5%, 6%, 7%, 8%, 9%, 10%, 15%, 20%, or 25%. In some embodiments, variable "z," representing the molar percentage of lipid component (3) (e.g., a PEG-modified lipid) is about 1%, 2%, 3%, 4%, 5%, 6%, 7%, 8%, 9%, 10%. In embodiments, variable "z," representing the molar percentage of lipid component (3) (e.g., a PEG-modified lipid) is about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7.5%, about 1% to about 7%, about 1% to about 6%, about 1% to about 5%, about 1% to about 4%, about 1% to about 3%, about 1% to about 2%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG-modified lipid) is no more than about 1%, 2%, 3%, 4%, 5%, 6%, 7%, 8%, 9%, 10%, 15%, 20%, or 25%. In some embodiments, variable "z," representing the weight percentage of lipid component (3) (e.g., a PEG lipid) is about 1%, 2%, 3%, 4%, 5%, 6%, 7%, 8%, 9%, 10%. In some embodiments, variable "z," representing the weight percentage of lipid component (3) (e.g., a PEG-modified lipid) is about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7.5%, about 1% to about 7%, about 1% to about 6%, about 1% to about 5%, about 1% to about 4%, about 1% to about 3%, about 1% to about 2%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Other Lipid Components

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18).

The PEG-modified phospholipid and derivitized lipids of the present invention may comprise a molar ratio from about 0% to about 20%, about 0.5% to about 20%, about 1% to about 20%, about 2% to about 20%, about 3% to about 20%, about 4% to about 20%, about 5% to about 20%, about 10% to about 20%, about 15% to about 20%, about 0% to about 15%, about 0% to about 10%, about 0% to about 5%, about 0% to about 4%, about 0% to about 3%, about 0% to about 220%, about 0% to about 1%, about 5% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids.

In some embodiments, cationic lipids that are not sterol-based cationic lipids can be used in liposomal compositions of the invention. Cationic lipids include, but are not limited to, N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-1-propanaminium (DOSPA), 1,2-Dioleoyl-3-Dimethylammonium-Propane (DODAP), 1,2-Dioleoyl-3-Trimethylammonium-Propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), or mixtures thereof.

Additional cationic lipids include 2-((2,3-Bis((9Z,12Z)-octadeca-9,12-dien-1-yloxy)propyl)disulfanyl)-N,N-dimethylethanamine (further described in U.S. Provisional Application No: PCT/US2012/041663, filed Jun. 8, 2012, the entire teachings of which are incorporated herein by reference in their entirety), cleavable lipids, such as, for example, one or more cationic lipids that comprise a cleavable disulfide (S—S) functional group, as further described in U.S. International Application No: PCT/US2012/041663. In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000 (Invitrogen), FUGENE, TRANSFECTAM (DOGS), and EFFECTENE.

Formation of Liposomes Encapsulating mRNA

The liposomal transfer vehicles for use in the present invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the therapeutic RNA (e.g., mRNA encoding CFTR) is associated on both the surface of the transfer vehicle (e.g., a liposome) and encapsulated within the same transfer vehicle. For example, during preparation of the compositions of the present invention, cationic liposomal transfer vehicles may associate with the nucleic acids (e.g., mRNA) through electrostatic interactions with such therapeutic mRNA.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of sterol-based cationic lipid, neutral lipid, and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Any desired lipids may be mixed at any ratios suitable for encapsulating mRNAs. In some embodiments, a suitable lipid solution contains a mixture of desired lipids including sterol-based cationic lipids, non-cationic lipids, and/or PEG-modified lipids. In some embodiments, a suitable lipid solution contain a mixture of desired lipids including one or more sterol-based cationic lipids, one or more helper lipids (e.g. non cationic lipids) and one or more PEG-modified lipids.

Exemplary combinations of sterol-based cationic lipids, non-cationic lipids, and PEG-modified lipids are described in the Examples section. For example, a suitable lipid solution may contain ICE, DOPE and DMG-PEG2K. The selection of sterol-based cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, a process for encapsulating mRNA in lipid nanoparticles comprises mixing an mRNA solution and a lipid solution, wherein the mRNA solution and/or the lipid solution are heated to a pre-determined temperature greater than ambient temperature prior to mixing to form lipid nanoparticles that encapsulate mRNA (see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety).

In some embodiments, a process for encapsulating mRNA in lipid nanoparticles comprises combining pre-formed lipid nanoparticles with mRNA (see U.S. Provisional Application Ser. No. 62/420,413, filed Nov. 10, 2016 and U.S. Provisional Application Ser. No. 62/580,155, filed Nov. 1, 2017, the disclosures of which are hereby incorporated by reference). In some embodiments, combining pre-formed lipid nanoparticles with mRNA results in lipid nanoparticles that show improved efficacy of intracellular delivery of the mRNA. In some embodiments, combining pre-formed lipid nanoparticles with mRNA results in very high encapsulation efficiencies of mRNA encapsulated in lipid nanoparticles (i.e., in the range of 90-95%). In some embodiments, combining pre-formed lipid nanoparticles with mRNA is achieved with pump systems which maintain the lipid/mRNA (N/P) ratio constant throughout the process and which also afford facile scale-up.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of lipo some is selected to facilitate systemic distribution of a protein or a peptide encoded by the mRNA. In some embodiments, it may be desirable to limit delivery of the mRNA to certain cells or tissues. For example, to target hepatocytes, a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm. In some embodiments, majority of nanoparticles in a composition, i.e., greater than about 50%, 55%, 60%, 65%, 70%, 75%, 80%, 85%, 90%, 95%, 96%, 97%, 98%, or 99% of the purified nanoparticles, have a size less than about 100 nm (e.g., less than about 95 nm, about 90 nm, about 85 nm, about 80 nm, about 75 nm, about 70 nm, about 65 nm, about 60 nm, about 55 nm, about 50 nm, about 45 nm, or about 40 nm). In some embodiments, substantially all of the purified nanoparticles have a size less than 100 nm (e.g., less than about 95 nm, about 90 nm, about 85 nm, about 80 nm, about 75 nm, about 70 nm, about 65 nm, about 60 nm, about 55 nm, about 50 nm, about 45 nm, or about 40 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Purification

Typically, subsequent to formulation the lipid nanoparticles containing mRNA are purified and/or concentrated. Various purification methods may be used. In some embodiments, lipid nanoparticles are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

Purified and/or concentrated lipid nanoparticles may be formulated in a desired buffer such as, for example, PBS.

Thus, the present invention provides a composition comprising purified nanoparticles described herein. In some embodiments, majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size less than about 100 nm (e.g., less than about 95 nm, about 90 nm, about 85 nm, about 80 nm, about 75 nm, about 70 nm, about 65 nm, about 60 nm, about 55 nm, about 50 nm, about 45 nm, or about 40 nm). In some embodiments, substantially all of the purified nanoparticles have a size less than 100 nm (e.g., less than about 95 nm, about 90 nm, about 85 nm, about 80 nm, about 75 nm, about 70 nm, about 65 nm, about 60 nm, about 55 nm, about 50 nm, about 45 nm, or about 40 nm).

In some embodiments, greater than about 70%, 75%, 80%, 85%, 90%, 95%, 96%, 97%, 98%, 99% of the purified nanoparticles in a composition provided by the present invention have a size ranging from about 40-90 nm (e.g., about 40-85 nm, about 40-80 nm, about 40-75 nm, about 40-70 nm, about 40-65 nm, or about 40-60 nm). In some embodiments, substantially all of the purified nanoparticles have a size ranging from about 40-90 nm (e.g., about 40-85 nm, about 40-80 nm, about 40-75 nm, about 40-70 nm, about 40-65 nm, or about 40-60 nm).

In some embodiments, the dispersity, or measure of heterogeneity in size of molecules (PDI), of nanoparticles in a composition provided by the present invention is less than about 0.16 (e.g., less than about 0.15, 0.14, 0.13, 0.12, 0.11, 0.10, 0.09, or 0.08).

In some embodiments, greater than about 75%, 80%, 85%, 90%, 95%, 96%, 97%, 98%, or 99% of the purified lipid nanoparticles in a composition provided by the present invention encapsulate an mRNA within each individual particle. In some embodiments, substantially all of the purified lipid nanoparticles in a composition encapsulate an mRNA within each individual particle.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

Nucleic Acids and mRNA

The present invention can be used to deliver any type of nucleic acid. A nucleic acid may be selected from the group comprising (but not limited to) DNA, messenger RNA (mRNA), small nuclear RNA (snRNA), guide RNA (gRNA), CRISPR RNA (crRNA), long noncoding RNA (lncRNA), micro RNA (miRNA), small interfering RNA (siRNA), and short hairpin RNA (shRNA).

The present invention can be used to deliver any mRNA. mRNA is typically thought of as the type of RNA that carries information from DNA to the ribosome. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein or a peptide.

Any mRNA capable of being translated into one or more peptides (e.g., antigens) or peptide fragments is contemplated as within the scope of the present invention. In some embodiments, an mRNA encodes one or more naturally occurring peptides. In some embodiments, an mRNA encodes one or more modified or non-natural peptides.

In some embodiments an mRNA encodes an intracellular protein or peptide. In some embodiments, an mRNA encodes a cytosolic protein or peptide. In some embodiments, an mRNA encodes a protein or peptide associated with the actin cytoskeleton. In some embodiments, an mRNA encodes a protein or peptide associated with the plasma membrane. In some specific embodiments, an mRNA encodes a transmembrane protein or peptide. In some specific embodiments an mRNA encodes an ion channel protein or peptide. In some embodiments, an mRNA encodes a perinuclear protein or peptide. In some embodiments, an mRNA encodes a nuclear protein or peptide. In some specific embodiments, an mRNA encodes a transcription factor. In some embodiments, an mRNA encodes a chaperone protein or peptide. In some embodiments, an mRNA encodes an intracellular enzyme (e.g., mRNA encoding an enzyme associated with urea cycle or lysosomal storage metabolic disorders). In some embodiments, an mRNA encodes a protein or peptide involved in cellular metabolism, DNA repair, transcription and/or translation. In some embodiments, an mRNA encodes an extracellular protein or peptide. In some embodiments, an mRNA encodes a protein or peptide associated with the extracellular matrix. In some embodiments an mRNA encodes a secreted protein or peptide. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

In some embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof) along with other components set out herein, and methods of the invention may comprise preparing and/or administering a composition comprising an mRNA encoding a protein listed in Table 1 (or a homolog thereof) along with other components set out herein.

TABLE 1

Secreted Proteins

| Uniprot ID | Protein Name | Gene Name |
|---|---|---|
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |

TABLE 1-continued

| Uniprot ID | Protein Name | Gene Name |
|---|---|---|
| | Secreted Proteins | |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (*S. cerevisiae*), isoform CRA_a | SEC11L3 |
| B4DJF9 | Protein Wnt | WNT4 |
| B4DUL4 | SEC11-like 1 (*S. cerevisiae*), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |

TABLE 1-continued

| Secreted Proteins | | |
|---|---|---|
| Uniprot ID | Protein Name | Gene Name |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |

TABLE 1-continued

| Secreted Proteins | | |
|---|---|---|
| Uniprot ID | Protein Name | Gene Name |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |

TABLE 1-continued

| Secreted Proteins | | |
|---|---|---|
| Uniprot ID | Protein Name | Gene Name |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |

TABLE 1-continued

| Secreted Proteins | | |
|---|---|---|
| Uniprot ID | Protein Name | Gene Name |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |

TABLE 1-continued

| Secreted Proteins | | |
|---|---|---|
| Uniprot ID | Protein Name | Gene Name |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |

TABLE 1-continued

| Secreted Proteins | | |
|---|---|---|
| Uniprot ID | Protein Name | Gene Name |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |

TABLE 1-continued

| Secreted Proteins | | |
|---|---|---|
| Uniprot ID | Protein Name | Gene Name |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |

TABLE 1-continued

| Secreted Proteins | | |
|---|---|---|
| Uniprot ID | Protein Name | Gene Name |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |

TABLE 1-continued

| Secreted Proteins | | |
|---|---|---|
| Uniprot ID | Protein Name | Gene Name |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |

TABLE 1-continued

| Secreted Proteins | | |
|---|---|---|
| Uniprot ID | Protein Name | Gene Name |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |

TABLE 1-continued

| Secreted Proteins | | |
|---|---|---|
| Uniprot ID | Protein Name | Gene Name |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |

TABLE 1-continued

| Secreted Proteins | | |
|---|---|---|
| Uniprot ID | Protein Name | Gene Name |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1(XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |

TABLE 1-continued

| Secreted Proteins | | |
|---|---|---|
| Uniprot ID | Protein Name | Gene Name |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |

TABLE 1-continued

| Secreted Proteins | | |
|---|---|---|
| Uniprot ID | Protein Name | Gene Name |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |

TABLE 1-continued

| Secreted Proteins | | |
|---|---|---|
| Uniprot ID | Protein Name | Gene Name |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroadherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |

TABLE 1-continued

| Secreted Proteins | | |
|---|---|---|
| Uniprot ID | Protein Name | Gene Name |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q765I0 | Urotensin-2B | UTS2D |
| Q76B58 | Protein FAM5C | FAM5C |
| Q76LX8 | A disintegrin and metalloproteinase with | ADAMTS13 |

TABLE 1-continued

| Secreted Proteins | | |
|---|---|---|
| Uniprot ID | Protein Name | Gene Name |
| | thrombospondin motifs 13 | |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |

TABLE 1-continued

| Secreted Proteins | | |
|---|---|---|
| Uniprot ID | Protein Name | Gene Name |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |

TABLE 1-continued

| Secreted Proteins | | |
|---|---|---|
| Uniprot ID | Protein Name | Gene Name |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |

TABLE 1-continued

| Secreted Proteins | | |
|---|---|---|
| Uniprot ID | Protein Name | Gene Name |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |

TABLE 1-continued

| Secreted Proteins | | |
|---|---|---|
| Uniprot ID | Protein Name | Gene Name |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orf39 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |

TABLE 1-continued

| Secreted Proteins | | |
|---|---|---|
| Uniprot ID | Protein Name | Gene Name |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |

TABLE 1-continued

| Secreted Proteins | | |
|---|---|---|
| Uniprot ID | Protein Name | Gene Name |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |

TABLE 1-continued

| Uniprot ID | Protein Name | Gene Name |
|---|---|---|
| | Secreted Proteins | |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |

TABLE 1-continued

| Secreted Proteins | | |
|---|---|---|
| Uniprot ID | Protein Name | Gene Name |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof) along with other components set out herein, and methods of the invention may comprise preparing and/or administering a composition comprising an mRNA encoding a protein chosen from the proteins listed in Table 2 (or a homolog thereof) along with other components set out herein.

TABLE 2

| Additional Exemplary Proteins | | |
|---|---|---|
| Uniprot ID | Protein Name | Gene Name |
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC11B | SEC11B |

TABLE 2-continued

| Additional Exemplary Proteins | | |
|---|---|---|
| Uniprot ID | Protein Name | Gene Name |
| P0C854 | Putative cat eye syndrome critical region protein 9 | CECR9 |
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 1 and Table 2 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1 or Table 2; thus, compositions of the invention may comprise an mRNA encoding a protein chosen from mammalian homologs or homologs from an animal of veterinary or industrial interest of a protein listed in Table 1 or Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 1 or Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a lysosomal protein chosen from Table 3. In some embodiments, the compositions and methods of the invention provide for the delivery of one or more mRNAs encoding one or more lysosomal and/or related proteins listed in Table 3; thus, compositions of the invention may comprise an mRNA encoding a protein listed in Table 3 (or a homolog thereof) along with other components set out herein, and methods of the invention may comprise preparing and/or administering a composition comprising an mRNA encoding a protein chosen from the proteins listed in Table 3 (or a homolog thereof) along with other components set out herein.

TABLE 3

| Lysosomal and Related Proteins |
|---|
| α-fucosidase |
| α-galactosidase |
| α-glucosidase |
| α-Iduronidase |
| α-mannosidase |
| α-N-acetylgalactosaminidase (α-galactosidase B) |
| β-galactosidase |
| β-glucuronidase |
| β-hexosaminidase |
| β-mannosidase |
| 3-hydroxy-3-methylglutaryl-CoA (HMG-CoA) lyase |
| 3-methylcrotonyl-CoA carboxylase |
| 3-O-sulfogalactosyl cerebroside sulfatase (arylsulfatase A) |
| acetyl-CoA transferase |
| acid alpha-glucosidase |
| acid ceramidase |
| acid lipase |
| acid phosphatase |
| acid sphingomyelinase |
| alpha-galactosidase A |
| arylsulfatase A |
| beta-galactosidase |
| beta-glucocerebrosidase |
| beta-hexosaminidase |
| biotinidase |
| cathepsin A |
| cathepsin K |
| CLN3 |
| CLN5 |
| CLN6 |
| CLN8 |
| CLN9 |
| cystine transporter (cystinosin) |

TABLE 3-continued

| Lysosomal and Related Proteins |
|---|
| cytosolic protein beta3A subunit of the adaptor protein-3 complex, AP3 |
| formyl-Glycine generating enzyme (FGE) |
| galactocerebrosidase |
| galactose-1-phosphate uridyltransferase (GALT) |
| galactose 6-sulfate sulfatase (also known as N-acetylgalactosamine-6-sulfatase) |
| glucocerebrosidase |
| glucuronate sulfatase |
| glucuronidase |
| glycoprotein cleaving enzymes |
| glycosaminoglycan cleaving enzymes |
| glycosylasparaginase (aspartylglucosaminidase) |
| GM2-AP |
| Heparan-alpha-glucosaminide N-acetyltransferase (HGSNAT, TMEM76) |
| Heparan sulfatase |
| hexosaminidase A lysosomal proteases methylmalonyl-CoA mutase |
| hyaluronidase |
| Iduronate sulfatase |
| LAMP-2 |
| lysosomal α-mannosidase |
| Lysosomal p40 (C2orf18) |
| Major facilitator superfamily domain containing 8 protein (MFSD8 or CLN7) |
| N-acetylgalactosamine 4-sulfatase |
| N-acetyl glucosamine 6-sulfatase |
| N-acetyl glucosaminidase |
| N-acetylglucosamine-1-phosphate transferase |
| NPC1 |
| NPC2 |
| palmitoyl-protein thioesterase |
| palmitoyl-protein thioesterase (CLN1) |
| Saposin A (Sphingolipid activator protein A) |
| Saposin B (Sphingolipid activator protein B) |
| Saposin C (Sphingolipid activator protein C) |
| Saposin D (Sphingolipid activator protein D) |
| sialic acid transporter (sialin) |
| sialidase |
| Sialin |
| sulfatase |
| Transmembrane protein 74 (TMEM74) |
| tripeptidyl-peptidase |
| tripeptidyl-peptidase I (CLN2) |
| UDP-N-acetylglucosamine-phosphotransferase |

Information regarding lysosomal proteins is available from Lubke et al., "Proteomics of the Lysosome," *Biochim Biophys Acta*. (2009) 1793: 625-635. In some embodiments, the protein listed in Table 3 and encoded by mRNA in the compositions and methods of the invention is a human protein. Sequences of the listed proteins are also available for various animals, including various mammals and animals of veterinary or industrial interest as described above.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

TABLE 4

| Exemplary Indications and Related Proteins | |
|---|---|
| Indication | Therapeutic Protein |
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |
| Acute intermittent porphyria | Porphobilinogen deaminase |
| Acute lymphocytic leukemia | |
| Acute myeloid leukemia | |
| Addison's disease | |
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |

TABLE 4-continued

| Exemplary Indications and Related Proteins | |
|---|---|
| Indication | Therapeutic Protein |
| Classic Rett Syndrome | |
| Classical galactosemia | Galactose-1-phosphate uridylyltransferase |
| *Clostridium difficile* associated diarrhea | |
| Clotting disorders | |
| COAD/COPD | |
| Cocaine addiction | |
| COL4A5-related disorders | |
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |

TABLE 4-continued

| Exemplary Indications and Related Proteins | |
|---|---|
| Indication | Therapeutic Protein |
| Glioblastoma multiforme | |
| Glomerulonephritis | |
| Glutaric acidemia, type I | Glutaryl-CoA dehydrogenase |
| GM2 gangliosidosis | HEXA, HEXB |
| Gout | Urate oxidase |
| Graft versus host disease | |
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |
| Hemophilia B | Factor IX |
| Hepatitis B, Hepatitis C | Interferon alpha |
| HER2+ breast cancer, gastric cancer | Anti-HER2 mAb |
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (*Clostridium difficile* prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |

TABLE 4-continued

| Exemplary Indications and Related Proteins | |
|---|---|
| Indication | Therapeutic Protein |
| Long-chain 3-OH acyl-CoA dehydrogenase deficiency | Long-chain-3-hydroxyacyl-CoA dehydrogenase |
| Lower respiratory infections | |
| Lysosomal acid lipase deficiency | Lysosomal acid lipase |
| Macular degeneration | |
| Major depressive disorder | |
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| *Pediculosis capitis* (head lice) | |
| Pelizaeus-Merzbacher disease | |
| Pemphigus vulgaris | |
| Peptic ulcer disease | |
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |

TABLE 4-continued

| Exemplary Indications and Related Proteins | |
|---|---|
| Indication | Therapeutic Protein |
| Pompe disease | Alpha glucosidase |
| Porphyria cutanea tarda | Uroporphyrinogen decarboxylase |
| Post herpetic neuralgia | |
| Post-organ transplant | |
| Pouchitis | |
| PPM-X Syndrome | |
| Prader-Willi syndrome | |
| Preeclampsia | |
| Premature ejaculation | |
| Prematurity and low birth weight | |
| Primary ciliary dyskinesia | |
| Primary glomerular diseases | |
| Primary humoral immune deficiencies (e.g., CVID) | Immunoglobulin |
| Proctitis | |
| Progressive multifocal leukoencephalopathy | |
| Progressive supranuclear palsy | |
| Propionic acidemia | Propionyl-CoA carboxylase |
| Prostate cancer | |
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |

TABLE 4-continued

| Exemplary Indications and Related Proteins | |
|---|---|
| Indication | Therapeutic Protein |
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, the present invention is used to prevent, treat and/or cure a subject affected with a disease or disorder listed or associated with the proteins listed in Tables 1, 2, 3 or 4. In some embodiments, an mRNA encodes one or more of Cystic Fibrosis Transmembrane Conductance Regulator (CFTR), argininosuccinate synthetase (ASS1), Factor IX, survival motor neuron 1 (SMN1), or phenylalanine hydroxylase (PAH).

In some embodiments, an mRNA encoding any one of the proteins listed in Tables 1, 2, 3 or 4 is codon-optimized. In one embodiment, an mRNA encoding CFTR is codon-optimized.

TABLE 5

| Human CFTR | |
|---|---|
| Codon-Optimized Human CFTR mRNA coding sequence | **AUG**CAACGCUCUCCUCUUGAAAAGGCCUCGGUGGUGUCCAAGCUCUU<br>CUUCUCGUGGACUAGACCCAUCCUGAGAAAGGGGUACAGACAGCGCU<br>UGGAGCUGUCCGAUAUCUAUCAAAUCCCUUCCGUGGACUCCGCGGAC<br>AACCUGUCCGAGAAGCUCGAGAGAGAAUGGGACAGAGAACUCGCCUC<br>AAAGAAGAACCCGAAGCUGAUUAAUGCGCUUAGGCGGUGCUUUUUC<br>UGGCGGUUCAUGUUCUACGGCAUCUUCCUCUACCUGGGAGAGGUCAC<br>CAAGGCCGUGCAGCCCCUGUUGCUGGGACGGAUUAUUGCCUCCUACG<br>ACCCCGACAACAAGGAAGAAAGAAGCAUCGCUAUCUACUUGGGCAUC<br>GGUCUGUGCCUGCUUUUCAUCGUCCGGACCCUCUUGUUGCAUCCUGC<br>UAUUUUCGGCCUGCAUCACAUUGGCAUGCAGAUGAGAAUUGCCAUG<br>UUUUCCCUGAUCUACAAGAAAACUCUGAAGCUCUCGAGCCGCGUGCU<br>UGACAAGAUUUCCAUCGGCCAGCUCGUGUCCCUGCUCUCCAACAAUC<br>UGAACAAGUUCGACGAGGGCCUCGCCCUGGCCCACUUCGUGUGGAUC<br>GCCCCUCUGCAAGUGGCGCUUCUGAUGGGCCUGAUCUGGGAGCUGCU<br>GCAAGCCUCGGCAUUCUGUGGGCUUGGAUUCCUGAUCGUGCUGGCAC<br>UGUUCCAGGCCGGACUGGGGCGGAUGAUGAUGAAGUACAGGGACCA<br>GAGAGCCGGAAAGAUUUCCGAACGGCUGGUGAUCACUUCGGAAAUG<br>AUCGAAAACAUCCAGUCAGUGAAGGCCUACUGCUGGGAAGAGGCCAU<br>GGAAAAGAUGAUUGAAAACCUCCGGCAAACCGAGCUGAAGCUGACCC<br>GCAAGGCCGCUUACGUGCGCUAUUUCAACUCGUCCGCUUUCUUCUUC<br>UCCGGGUUCUUCGUGGUGUUUCUCUCCGUGCUCCCCUACGCCCUGAU<br>UAAGGGAAUCAUCCUCAGGAAGAUCUUCACCACCAUUUCCUUCUGUA<br>UCGUGCUCCGCAUGGCCGUGACCCGGCAGUUCCCAUGGGCCGUGCAG<br>ACUUGGUACGACUCCCUGGGAGCCAUUAACAAGAUCCAGGACUUCCU<br>UCAAAAGCAGGAGUACAAGACCCUCGAGUACAACCUGACUACUACCG<br>AGGUCGUGAUGGAAAACGUCACCGCCUUUUGGGAGGAGGGAUUUGG<br>CGAACUGUUCGAGAAGGCCAAGCAGAACAACAACAACCGCAAGACCU<br>CGAACGGUGACGACUCCCUCUUCUUUUCAAACUUCAGCCUGCUCGGG<br>ACGCCCGUGCUGAAGGACAUUAACUUCAAGAUCGAAAGAGGACAGCU<br>CCUGGCGGUGGCCGGAUCGACCGGAGCCGGAAAGACUUCCCUGCUGA<br>UGGUGAUCAUGGGAGAGCUUGAACCUAGCGAGGGAAAGAUCAAGCA<br>CUCCGGCCGCAUCAGCUUCUGUAGCCAGUUUUCCUGGAUCAUGCCCG<br>GAACCAUUAAGGAAAACAUCAUCUUCGGCGUGUCCUACGAUGAAUAC<br>CGCUACCGGUCCGUGAUCAAAGCCUGCCAGCUGGAAGAGGAUAUUUC<br>AAAGUUCGCGGAGAAAGAUAACAUCGUGCUGGGCGAAGGGGGUAUU<br>ACCUUGUCGGGGGGCCAGCGGGCUAGAAUCUCGCUGGCCAGAGCCGU<br>GUAUAAGGACGCCGACCUGUAUCUCCUGGACUCCCCCUUCGGAUACC<br>UGGACGUCCUGACCGAAAAGGAGAUCUUCGAAUCGUGCGUGUGCAA<br>GCUGAUGGCUAACAAGACUCGCAUCCUCGUGACCUCCAAAAUGGAGC<br>ACCUGAAGAAGGCAGACAAGAUUCUGAUUCUGCAUGAGGGGUCCUCC<br>UACUUUUACGGCACCUUCUCGGAGUUGCAGAACUUGCAGCCCGACUU<br>CUCAUCGAAGCUGAUGGGUUGCGACAGCUUCGACCAGUUCUCCGCCG<br>AAAGAAGGAACUCGAUCCUGACGGAAACCUUGCACCGCUUCUCUUUG<br>GAAGGCGACGCCCCUGUGUCAUGGACCGAGACUAAGAAGCAGAGCUU<br>CAAGCAGACCGGGGAAUUCGGCGAAAAGAGGAAGAACAGCAUCUUG<br>AACCCCAUUAACUCCAUCCGCAAGUUCUCAAUCGUGCAAAAGACGCC<br>ACUGCAGAUGAACGGCAUUGAGGAGGACUCCGACGAACCCCUUGAGA<br>GGCGCCUGUCCCUGGUGCCGGACAGCGAGCAGGGAGAAGCCAUCCUG<br>CCUCGGAUUUCCGUGAUCUCCACUGGUCCGACGCUCCAAGCCCGGCG<br>GCGGCAGUCCGUGCUGAACCUGAUGACCCACAGCGUGAACCAGGGCC<br>AAAACAUUCACCGCAAGACUACCGCAUCCACCCGGAAAGUGUCCCUG<br>GCACCUCAAGCGAAUCUUACCGAGCUCGACAUCUACUCCCGGAGACU |

TABLE 5-continued

| | Human CFTR |
|---|---|
| | GUCGCAGGAAACCGGGCUCGAAAUUUCCGAAGAAAUCAACGAGGAG<br>GAUCUGAAAGAGUGCUUCUUCGACGAUAUGGAGUCGAUACCCGCCGU<br>GACGACUUGGAACACUUAUCUGCGGUACAUCACUGUGCACAAGUCAU<br>UGAUCUUCGUGCUGAUUUGGUGCCUGGUGAUUUUCCUGGCCGAGGU<br>CGCGGCCUCACUGGUGGUGCUCUGGCUGUUGGGAAACACGCCUCUGC<br>AAGACAAGGGAAACUCCACGCACUCGAGAAACAACAGCUAUGCCGUG<br>AUUAUCACUUCCACCUCCUCUUAUUACGUGUUCUACAUCUACGUCGG<br>AGUGGCGGAUACCCUGCUCGCGAUGGGUUUCUUCAGAGGACUGCCGC<br>UGGUCCACACCUUGAUCACCGUCAGCAAGAUUCUUCACCACAAGAUG<br>UUGCAUAGCGUGCUGCAGGCCCCCAUGUCCACCCUCAACACUCUGAA<br>GGCCGGAGGCAUUCUGAACAGAUUCUCCAAGGACAUCGCUAUCCUGG<br>ACGAUCUCCUGCCGCUUACCAUCUUUGACUUCAUCCAGCUGCUGCUG<br>AUCGUGAUUGGAGCAAUCGCAGUGGUGGCGGUGCUGCAGCCUUACA<br>UUUUCGUGGCCACUGUGCCGGUCAUUGUGGCGUUCAUCAUGCUGCGG<br>GCCUACUUCCUCCAAACCAGCCAGCAGCUGAAGCAACUGGAAUCCGA<br>GGGACGAUCCCCCAUCUUCACUCACCUUGUGACGUCGUUGAAGGGAC<br>UGUGGACCCUCCGGGCUUUCGGACGGCAGCCCUACUUCGAAACCCUC<br>UUCCACAAGGCCCUGAACCUCCACACCGCCAAUUGGUUCCUGUACCU<br>GUCCACCCUGCGGUGGUUCCAGAUGCGCAUCGAGAUGAUUUUCGUCA<br>UCUUCUUCAUCGCGGUCACAUUCAUCAGCAUCCUGACUACCGGAGAG<br>GGAGAGGGACGGGUCGGAAUAAUCCUGACCCUCGCCAUGAACAUUAU<br>GAGCACCCUGCAGUGGGCAGUGAACAGCUCGAUCGACGUGGACAGCC<br>UGAUGCGAAGCGUCAGCCGCGUGUUCAAGUUCAUCGACAUGCCUACU<br>GAGGGAAAACCCACUAAGUCCACUAAGCCCUACAAAAAUGGCCAGCU<br>GAGCAAGGUCAUGAUCAUCGAAAACUCCCACGUGAAGAAGGACGAU<br>AUUUGGCCCUCCGGAGGUCAAAUGACCGUGAAGGACCUGACCGCAAA<br>GUACACCGAGGGAGGAAACGCCAUUCUCGAAAACAUCAGCUUCUCCA<br>UUUCGCCGGGACAGCGGGUCGGCCUUCUCGGGCGGACCGGUUCCGGG<br>AAGUCAACUCUGCUGUCGGCUUUCCUCCGGCUGCUGAAUACCGAGGG<br>GGAAAUCCAAAUUGACGGCGUGUCUUGGGAUUCCAUUACUCUGCAGC<br>AGUGGCGGAAGGCCUUCGGCGUGAUCCCCCAGAAGGUGUUCAUCUUC<br>UCGGGUACCUUCCGGAAGAACCUGGAUCCUUACGAGCAGUGGAGCGA<br>CCAAGAAAUCUGGAAGGUCGCCGACGAGGUCGGCCUGCGCUCCGUGA<br>UUGAACAAUUUCCUGGAAAGCUGGACUUCGUGCUCGUCGACGGGGG<br>AUGUGUCCUGUCGCACGGACAUAAGCAGCUCAUGUGCCUCGCACGGU<br>CCGUGCUCUCCAAGGCCAAGAUUCUGCUGCUGGACGAACCUUCGGCC<br>CACCUGGAUCCGGUCACCUACCAGAUCAUCAGGAGGACCCUGAAGCA<br>GGCCUUUGCCGAUUGCACCGUGAUUCUCUGCGAGCACCGCAUCGAGG<br>CCAUGCUGGAGUGCCAGCAGUUCCUGGUCAUCGAGGAGAACAAGGUC<br>CGCCAAUACGACUCCAUUCAAAAGCUCCUCAACGAGCGGUCGCUGUU<br>CAGACAAGCUAUUUCACCGUCCGAUAGAGUGAAGCUCUUCCCGCAUC<br>GGAACAGCUCAAAGUGCAAAUCGAAGCCGCAGAUCGCAGCCUUGAAG<br>GAAGAGACUGAGGAAGAGGUGCAGGACACCCGGCUU**UAA**<br>(SEQ ID NO: 1) |
| Comparison Codon-Optimized Human CFTR mRNA coding sequence | **AUG**CAGCGGUCCCCGCUCGAAAAGGCCAGUGUCGUGUCCAAACUCUU<br>CUUCUCAUGGACUCGGCCUAUCCUUAGAAAGGGGUAUCGGCAGAGGC<br>UUGAGUUGUCUGACAUCUACCAGAUCCCCUCGGUAGAUUCGGCGGAU<br>AACCUCUCGGAGAAGCUCGAACGGGAAUGGGACCGCGAACUCGCGUC<br>UAAGAAAAACCCGAAGCUCAUCAACGCACUGAGAAGGUGCUUCUUCU<br>GGCGGUUCAUGUUCUACGGUAUCUUCUUGUAUCUCGGGGAGGUCAC<br>AAAAGCAGUCCAACCCCUGUUGUUGGGUCGCAUUAUCGCCUCGUACG<br>ACCCCGAUAACAAAGAAGAACGGAGCAUCGCGAUCUACCUCGGGAUC<br>GGACUGUGUUUGCUUUUCAUCGUCAGAACACUUUUGUUGCAUCCAGC<br>AAUCUUCGGCCUCCAUCACAUCGGUAUGCAGAUGCGAAUCGCUAUGU<br>UUAGCUUGAUCUACAAAAAGACACUGAAACUCUCGUCGCGGGUGUU<br>GGAUAAGAUUUCCAUCGGUCAGUUGGUGUCCCUGCUUAGUAAUAAC<br>CUCAACAAAUUCGAUGAGGGACUGGCGCUGGCACAUUUCGUGUGGA<br>UUGCCCCGUUGCAAGUCGCCCUUUUGAUGGGCCUUAUUUGGGAGCUG<br>UUGCAGGCAUCUGCCUUUUGUGGCCUGGGAUUUCUGAUUGUGUUGG<br>CAUUGUUUCAGGCUGGGCUUGGGCGGAUGAUGAUGAAGUAUCGCGA<br>CCAGAGAGCGGGUAAAAUCUCGGAAAGACUCGUCAUCACUUCGGAAA<br>UGAUCGAAAACAUCCAGUCGGUCAAAGCCUAUUGCUGGGAAGAAGC<br>UAUGGAGAAGAUGAUUGAAAACCUCCGCCAAACUGAGCUGAAACUG<br>ACCCGCAAGGCGGCGUAUGUCCGGUAUUUCAAUUCGUCAGCGUUCUU<br>CUUUUCCGGGUUCUUCGUUGUCUUUCUCUCGGUUUUGCCUUAUGCCU<br>UGAUUAAGGGGAUUAUCCUCCGCAAGAUUUUCACCACGAUUUCGUUC<br>UGCAUUGUAUUGCGCAUGGCAGUGACACGGCAAUUUCCGUGGGCCGU<br>GCAGACAUGGUAUGACUCGCUUGGAGCGAUCAACAAAAUCCAAGACU<br>UCUUGCAAAAGCAAGAGUACAAGACCCUGGAGUACAAUCUUACUACU<br>ACGGAGGUAGUAAUGGAGAAUGUGACGGCUUUUUGGGAAGAGGGUU<br>UUGGAGAACUGUUUGAGAAAGCAAAGCAGAAUAACAACAACCGCAA<br>GACCUCAAAUGGGGACGAUUCCCUGUUUUUCUCGAACUUCUCCCUGC<br>UCGGAACACCCGUGUUGAAGGACAUCAAUUUCAAGAUUGAGAGGGG<br>ACAGCUUCUCGCGGUAGCGGGAAGCACUGGUGCGGGAAAAACUAGCC<br>UCUUGAUGGUGAUUAUGGGGGAGCUUGAGCCCAGCGAGGGGAAGAU<br>UAAACACUCCGGGCGUAUCUCAUUCUGUAGCCAGUUUUCAUGGAUCA<br>UGCCCGGAACCAUUAAAGAGAACAUCAUUUUCGGAGUAUCCUAUGA |

TABLE 5-continued

| | Human CFTR |
|---|---|
| | UGAGUACCGAUACAGAUCGGUCAUUAAGGCGUGCCAGUUGGAAGAG<br>GACAUUUCUAAGUUCGCCGAGAAGGAUAACAUCGUCUUGGGAGAAG<br>GGGGUAUUACAUUGUCGGGAGGGCAGCGAGCGCGGAUCAGCCUCGCG<br>AGAGCGGUAUACAAAGAUGCAGAUUUGUAUCUGCUUGAUUCACCGU<br>UUGGAUACCUCGACGUAUUGACAGAAAAAGAAAUCUUCGAGUCGUG<br>CGUGUGUAAACUUAUGGCUAAUAAGACGAGAAUCCUGGUGACAUCA<br>AAAAUGGAACACCUUAAGAAGGCGGACAAGAUCCUGAUCCUCCACGA<br>AGGAUCGUCCUACUUUUACGGCACUUUCUCAGAGUUGCAAAACUUGC<br>AGCCGGACUUCUCAAGCAAACUCAUGGGGUGUGACUCAUUCGACCAG<br>UUCAGCGCGGAACGGCGGAACUCGAUCUUGACGGAAACGCUGCACCG<br>AUUCUCGCUUGAGGGUGAUGCCCCGGUAUCGUGGACCGAGACAAAGA<br>AGCAGUCGUUUAAGCAGACAGGAGAAUUUGGUGAGAAAAGAAAGAA<br>CAGUAUCUUGAAUCCUAUUAACUCAAUUCGCAAGUUCUCAAUCGUCC<br>AGAAAACUCCACUGCAGAUGAAUGGAAUUGAAGAGGAUUCGGACGA<br>ACCCCUGGAGCGCAGGCUUAGCCUCGUGCCGGAUUCAGAGCAAGGGG<br>AGGCCAUUCUUCCCCGGAUUUCGGUGAUUUCAACCGGACCUACACUU<br>CAGGCGAGGCGAAGGCAAUCCGUGCUCAACCUCAUGACGCAUUCGGU<br>AAACCAGGGGCAAAACAUUCACCGCAAAACGACGGCCUCAACGAGAA<br>AAGUGUCACUUGCACCCCAGGCGAAUUUGACUGAACUCGACAUCUAC<br>AGCCGUAGGCUUUCGCAAGAAACCGGACUUGAGAUCAGCGAAGAAA<br>UCAAUGAAGAAGAUUUGAAAGAGUGUUUCUUUGAUGACAUGGAAUC<br>AAUCCCAGCGGUGACAACGUGGAACACAUACUUGCGUUACAUCACGG<br>UGCACAAGUCCUUGAUUUUCGUCCUCAUCUGGUGUCUCGUGAUCUUU<br>CUCGCUGAGGUCGCAGCGUCACUUGUGGUCCUCUGGCUGCUUGGUAA<br>UACGCCCUUGCAAGACAAAGGCAAUUCUACACACUCAAGAAACAAUU<br>CCUAUGCCGUGAUUAUCACUUCUACAAGCUCGUAUUACGUGUUUUAC<br>AUCUACGUAGGAGUGGCCGACACUCUGCUCGCGAUGGGUUUCUUCCG<br>AGGACUCCCACUCGUUCACACGCUUAUCACUGUCUCCAAGAUUCUCC<br>ACCAUAAGAUGCUUCAUAGCGUACUGCAGGCUCCCAUGUCCACCUUG<br>AAUACGCUCAAGGCGGGAGGUAUUUUGAAUCGCUUCUCAAAAGAUA<br>UUGCAAUUUUGGAUGACCUUCUGCCCCUGACGAUCUUCGACUUCAUC<br>CAGUUGUUGCUGAUCGUGAUUGGGGCUAUUGCAGUAGUCGCUGUCC<br>UCCAGCCUUACAUUUUUGUCGCGACCGUUCCGGUGAUCGUGGCGUUU<br>AUCAUGCUGCGGGCCUAUUUCUUGCAGACGUCACAGCAGCUUAAGCA<br>ACUGGAGUCUGAAGGGAGGUCGCCUAUCUUUACGCAUCUUGUGACCA<br>GUUUGAAGGGAUUGUGGACGUUGCGCGCCUUUGGCAGGCAGCCCUAC<br>UUUGAAACACUGUUCCACAAAGCGCUGAAUCUCCAUACGGCAAAUUG<br>GUUUUUGUAUUUGAGUACCCUCCGAUGGUUUCAGAUGCGCAUUGAG<br>AUGAUUUUUGUGAUCUUCUUUAUCGCGGUGACUUUUAUCUCCAUCU<br>UGACCACGGGAGAGGGCGAGGGACGGGUCGGUAUUAUCCUGACACUC<br>GCCAUGAACAUUAUGAGCACUUUGCAGUGGGCAGUGAACAGCUCGA<br>UUGAUGUGGAUAGCCUGAUGAGGUCCGUUUCGAGGGUCUUUAAGUU<br>CAUCGACAUGCCGACGGAGGGAAAGCCCACAAAAAGUACGAAACCCU<br>AUAAGAAUGGGCAAUUGAGUAAGGUAAUGAUCAUCGAGAACAGUCA<br>CGUGAAGAAGGAUGACAUCUGGCCUAGCGGGGGUCAGAUGACCGUG<br>AAGGACCUGACGGCAAAAUACACCGAGGGAGGGAACGCAAUCCUUGA<br>AAACAUCUCGUUCAGCAUUAGCCCCGGUCAGCGUGUGGGGUUGCUCG<br>GGAGGACCGGGUCAGGAAAAUCGACGUUGCUGUCGGCCUUCUUGAG<br>ACUUCUGAAUACAGAGGGUGAGAUCCAGAUCGACGGCGUUUCGUGG<br>GAUAGCAUCACCUUGCAGCAGUGGCGGAAAGCGUUUGGAGUAAUCCC<br>CCAAAAGGUCUUUAUCUUUAGCGGAACCUUCCGAAAGAAUCUCGAUC<br>CUUAUGAACAGUGGUCAGAUCAAGAGAUUUGGAAAGUCGCGGACGA<br>GGUUGGCCUUCGGAGUGUAAUCGAGCAGUUUCCGGGAAAACUCGAC<br>UUUGUCCUUGUAGAUGGGGGAUGCGUCCUGUCGCAUGGGCACAAGC<br>AGCUCAUGUGCCUGGCGCGAUCCGUCCUCUCUAAAGCGAAAAUUCUU<br>CUCUUGGAUGAACCUUCGGCCCAUCUGGACCCGGUAACGUAUCAGAU<br>CAUCAGAAGGACACUUAAGCAGGCGUUUGCCGACUGCACGGUGAUUC<br>UCUGUGAGCAUCGUAUCGAGGCCAUGCUCGAAUGCCAGCAAUUUCUU<br>GUCAUCGAAGAGAAUAAGGUCCGCCAGUACGACUCCAUCCAGAAGCU<br>GCUUAAUGAGAGAUCAUUGUUCCGGCAGGCGAUUUCACCAUCCGAUA<br>GGGUGAAACUUUUUCCACACAGAAAUUCGUCGAAGUGCAAGUCCAA<br>ACCGCAGAUCGCGGCCUUGAAAGAAGAGACUGAAGAAGAAGUUCAA<br>GACACGCGUCUU**UAA** (SEQ ID NO: 2) |
| Codon-Optimized Human CFTR 'STOP' Coding Sequence | AUGCAGCGGUCCUAGCUCGAAAAGGCCAGUGUCGUGUCCAAACUCUU<br>CUUCUCAUGGACUCGGCCUAUCCUUAGAAAGGGGUAUCGGCAGAGGC<br>UUGAGUUGUCUGACAUCUACCAGUGACCCUCGGUAGAUUCGGCGGAU<br>AACCUCUCGGAGAAGCUCGAACGGGAAUGGGACCGCGAACUCGCGUC<br>UAAGAAAAACCCGAAGCUCAUCAACGCACUGAGAAGGUGCUUCUUCU<br>GGCGGUUCAUGUUCUACGGUAUCUUCUUGUAUCUCGGGGAGGUCAC<br>AAAAGCAGUCCAACCCCUGUUGUUGGGUCGCAUUAUCGCCUCGUACG<br>ACCCCGAUAACAAAGAAGAACGGAGCAUCGCGAUCUACCUCGGGAUC<br>GGACUGUGUUUGCUUUUCAUCGUCAGAACACUUUUGUUGCAUCCAGC<br>AAUCUUCGGCCUCCAUCACAUCGGUAUGCAGAUGCGAAUCGCUAUGU<br>UUAGCUUGAUCUACAAAAAGACACUGAAACUCUCGUCGCGGGUGUU<br>GGAUAAGAUUUCCAUCGGUCAGUUGGUGUCCCUGCUUAGUAAUAAC<br>CUCAACAAAUUCGAUGAGGGACUGGCGCUGGCACAUUUCGUGUGGA<br>UUGCCCCGUUGCAAGUCGCCCUUUUGAUGGGCCUUAUUUGGGAGCUG |

TABLE 5-continued

| Human CFTR |
|---|
| UUGCAGGCAUCUGCCUUUUGUGGCCUGGGAUUUCUGAUUGUGUUGG<br>CAUUGUUUCAGGCUGGGCUUGGGCGGAUGAUGAUGAAGUAUCGCGA<br>CCAGAGAGCGGGUAAAAUCUCGGAAAGACUCGUCAUCACUUCGGAAA<br>UGAUCGAAAACAUCCAGUCGGUCAAAGCCUAUUGCUGGGAAGAAGC<br>UAUGGAGAAGAUGAUUGAAAACCUCCGCCAAACUGAGCUGAAACUG<br>ACCCGCAAGGCGGCGUAUGUCCGGUAUUUCAAUUCGUCAGCGUUCUU<br>CUUUUCCGGGUUCUUCGUUGUCUUUCUCUCGGUUUUGCCUUAUGCCU<br>UGAUUAAGGGGAUUAUCCUCCGCAAGAUUUUCACCACGAUUUCGUUC<br>UGCAUUGUAUUGCGCAUGGCAGUGACACGGCAAUUUCCGUGGGCCGU<br>GCAGACAUGGUAUGACUCGCUUGGAGCGAUCAACAAAAUCCAAGACU<br>UCUUGCAAAAGCAAGAGUACAAGACCCUGGAGUACAAUCUUACUACU<br>ACGGAGGUAGUAAUGGAGAAUGUGACGGCUUUUUGGGAAGAGGGUU<br>UUGGAGAACUGUUUGAGAAAGCAAAGCAGAAUAACAACAACCGCAA<br>GACCUCAAAUGGGGACGAUUCCCUGUUUUUCUCGAACUUCUCCCUGC<br>UCGGAACACCCGUGUUGAAGGACAUCAAUUUCAAGAUUGAGAGGGG<br>ACAGCUUCUCGCGGUAGCGGGAAGCACUGGUGCGGGAAAAACUAGCC<br>UCUUGAUGGUGAUUAUGGGGGAGCUUGAGCCCAGCGAGGGGAAGAU<br>UAAACACUCCGGGCGUAUCUCAUUCUGUAGCCAGUUUUCAUGGAUCA<br>UGCCCGGAACCAUUAAAGAGAACAUCAUUUUCGGAGUAUCCUAUGA<br>UGAGUACCGAUACAGAUCGGUCAUUAAGGCGUGCCAGUUGGAAGAG<br>GACAUUUCUAAGUUCGCCGAGAAGGAUAACAUCGUCUUGGGAGAAG<br>GGGGUAUUACAUUGUCGGGAGGGCAGCGAGCGCGGAUCAGCCUCGCG<br>AGAGCGGUAUACAAAGAUGCAGAUUUGUAUCUGCUUGAUUCACCGU<br>UUGGAUACCUCGACGUAUUGACAGAAAAAGAAAUCUUCGAGUCGUG<br>CGUGUGUAAACUUAUGGCUAAUAAGACGAGAAUCCUGGUGACAUCA<br>AAAAUGGAACACCUUAAGAAGGCGGACAAGAUCCUGAUCCUCCACGA<br>AGGAUCGUCCUACUUUUACGGCACUUUCUCAGAGUUGCAAAACUUGC<br>AGCCGGACUUCUCAAGCAAACUCAUGGGGUGUGACUCAUUCGACCAG<br>UUCAGCGCGGAACGGCGGAACUCGAUCUUGACGGAAACGCUGCACCG<br>AUUCUCGCUUGAGGGUGAUGCCCCGGUAUCGUGGACCGAGACAAAGA<br>AGCAGUCGUUUAAGCAGACAGGAGAAUUUGGUGAGAAAAGAAAGAA<br>CAGUAUCUUGAAUCCUAUUAACUCAAUUCGCAAGUUCUCAAUCGUCC<br>AGAAAACUCCACUGCAGAUGAAUGGAAUUGAAGAGGAUUCGGACGA<br>ACCCCUGGAGCGCAGGCUUAGCCUCGUGCCGGAUUCAGAGCAAGGGG<br>AGGCCAUUCUUCCCCGGAUUUCGGUGAUUUCAACCGGACCUACACUU<br>CAGGCGAGGCGAAGGCAAUCCGUGCUCAACCUCAUGACGCAUUCGGU<br>AAACCAGGGGCAAAACAUUCACCGCAAAACGACGGCCUCAACGAGAA<br>AAGUGUCACUUGCACCCCAGGCGAAUUUGACUGAACUCGACAUCUAC<br>AGCCGUAGGCUUUCGCAAGAAACCGGACUUGAGAUCAGCGAAGAAA<br>UCAAUGAAGAAGAUUUGAAAGAGUGUUUCUUUGAUGACAUGGAAUC<br>AAUCCCAGCGGUGACAACGUGGAACACAUACUUGCGUUACAUCACGG<br>UGCACAAGUCCUUGAUUUUCGUCCUCAUCUGGUGUCUCGUGAUCUUU<br>CUCGCUGAGGUCGCAGCGUCACUUGUGGUCCUCUGGCUGCUUGGUAA<br>UACGCCCUUGCAAGACAAAGGCAAUUCUACACACUCAAGAAACAAUU<br>CCUAUGCCGUGAUUAUCACUUCUACAAGCUCGUAUUACGUGUUUUAC<br>AUCUACGUAGGAGUGGCCGACACUCUGCUCGCGAUGGGUUUCUUCCG<br>AGGACUCCCACUCGUUCACACGCUUAUCACUGUCUCCAAGAUUCUCC<br>ACCAUAAGAUGCUUCAUAGCGUACUGCAGGCUCCCAUGUCCACCUUG<br>AAUACGCUCAAGGCGGGAGGUAUUUUGAAUCGCUUCUCAAAAGAUA<br>UUGCAAUUUUGGAUGACCUUCUGCCCCUGACGAUCUUCGACUUCAUC<br>CAGUUGUUGCUGAUCGUGAUUGGGGCUAUUGCAGUAGUCGCUGUCC<br>UCCAGCCUUACAUUUUUGUCGCGACCGUUCCGGUGAUCGUGGCGUUU<br>AUCAUGCUGCGGGCCUAUUUCUUGCAGACGUCACAGCAGCUUAAGCA<br>ACUGGAGUCUGAAGGGAGGUCGCCUAUCUUUACGCAUCUUGUGACCA<br>GUUUGAAGGGAUUGUGGACGUUGCGCGCCUUUGGCAGGCAGCCCUAC<br>UUUGAAACACUGUUCCACAAAGCGCUGAAUCUCCAUACGGCAAAUUG<br>GUUUUUGUAUUUGAGUACCCUCCGAUGGUUUCAGAUGCGCAUUGAG<br>AUGAUUUUUGUGAUCUUCUUUAUCGCGGUGACUUUUAUCUCCAUCU<br>UGACCACGGGAGAGGGCGAGGGACGGGUCGGUAUUAUCCUGACACUC<br>GCCAUGAACAUUAUGAGCACUUUGCAGUGGGCAGUGAACAGCUCGA<br>UUGAUGUGGAUAGCCUGAUGAGGUCCGUUUCGAGGGUCUUUAAGUU<br>CAUCGACAUGCCGACGGAGGGAAAGCCCACAAAAAGUACGAAACCCU<br>AUAAGAAUGGGCAAUUGAGUAAGGUAAUGAUCAUCGAGAACAGUCA<br>CGUGAAGAAGGAUGACAUCUGGCCUAGCGGGGGUCAGAUGACCGUG<br>AAGGACCUGACGGCAAAAUACACCGAGGGAGGGAACGCAAUCCUUGA<br>AAACAUCUCGUUCAGCAUUAGCCCCGGUCAGCGUGUGGGGUUGCUCG<br>GGAGGACCGGGUCAGGAAAAUCGACGUUGCUGUCGGCCUUCUUGAG<br>ACUUCUGAAUACAGAGGGUGAGAUCCAGAUCGACGGCGUUUCGUGG<br>GAUAGCAUCACCUUGCAGCAGUGGCGGAAAGCGUUUGGAGUAAUCCC<br>CCAAAAGGUCUUUAUCUUUAGCGGAACCUUCCGAAAGAAUCUCGAUC<br>CUUAUGAACAGUGGUCAGAUCAAGAGAUUUGGAAAGUCGCGGACGA<br>GGUUGGCCUUCGGAGUGUAAUCGAGCAGUUUCCGGGAAAACUCGAC<br>UUUGUCCUUGUAGAUGGGGGAUGCGUCCUGUCGCAUGGGCACAAGC<br>AGCUCAUGUGCCUGGCGCGAUCCGUCCUCUCUAAAGCGAAAAUUCUU<br>CUCUUGGAUGAACCUUCGGCCCAUCUGGACCCGGUAACGUAUCAGAU<br>CAUCAGAAGGACACUUAAGCAGGCGUUUGCCGACUGCACGGUGAUUC<br>UCUGUGAGCAUCGUAUCGAGGCCAUGCUCGAAUGCCAGCAAUUUCUU<br>GUCAUCGAAGAGAAUAAGGUCCGCCAGUACGACUCCAUCCAGAAGCU |

TABLE 5-continued

| | Human CFTR |
|---|---|
| | GCUUAAUGAGAGAUCAUUGUUCCGGCAGGCGAUUUCACCAUCCGAUA<br>GGGUGAAACUUUUUCCACACAGAAAUUCGUCGAAGUGCAAGUCCAA<br>ACCGCAGAUCGCGGCCUUGAAAGAAGAGACUGAAGAAGAAGUUCAA<br>GACACGCGUCUUUAA (SEQ ID NO: 3) |
| Human CFTR Protein Sequence | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 4) |

Exemplary Codon-Optimized Human Cystic Fibrosis Transmembrane Conductance Regulator (CFTR) mRNAs Construct Design:

X-Coding Sequence-Y

5' and 3' UTR Sequences:

X (5' UTR Sequence) =

(SEQ ID NO: 5)

GGACAGAUCGCCUGGAGACGCCAUCCACGCUGUUUUGACCUCCAUAGAAGA

CACCGGGACCGAUCCAGCCUCCGCGGCCGGGAACGGUGCAUUGGAACGCGG

AUUCCCCGUGCCAAGAGUGACUCACCGUCCUUGACACG

Y (3' UTR Sequence) =

(SEQ ID NO: 6)

CGGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCAA

GCU

OR (SEQ ID NO: 7)

GGGUGGCAUCCCUGUGACCCCUCCCCAGUGCCUCUCCUGGCCCUGGAAGUU

GCCACUCCAGUGCCCACCAGCCUUGUCCUAAUAAAAUUAAGUUGCAUCAAA

GCU

In one embodiment, a codon-optimized human CFTR mRNA sequence includes SEQ ID NO: 1.

In one embodiment, a full-length codon-optimized human CFTR mRNA sequence is:

(SEQ ID NO: 8)

GGACAGAUCGCCUGGAGACGCCAUCCACGCUGUUUUGACCUCCAUAGAAGA

CACCGGGACCGAUCCAGCCUCCGCGGCCGGGAACGGUGCAUUGGAACGCGG

AUUCCCCGUGCCAAGAGUGACUCACCGUCCUUGACACGAUGCAACGCUCUC

CUCUUGAAAAGGCCUCGGUGGUGUCCAAGCUCUUCUUCUCGUGGACUAGAC

CCAUCCUGAGAAAGGGGUACAGACAGCGCUUGGAGCUGUCCGAUAUCUAUC

AAAUCCCUUCCGUGGACUCCGCGGACAACCUGUCCGAGAAGCUCGAGAGAG

AAUGGGACAGAGAACUCGCCUCAAAGAAGAACCCGAAGCUGAUUAAUGCGC

UUAGGCGGUGCUUUUUCUGGCGGUUCAUGUUCUACGGCAUCUUCCUCUACC

UGGGAGAGGUCACCAAGGCCGUGCAGCCCCUGUUGCUGGGACGGAUUAUUG

CCUCCUACGACCCCGACAACAAGGAAGAAAGAAGCAUCGCUAUCUACUUGG

GCAUCGGUCUGUGCCUGCUUUUCAUCGUCCGGACCCUCUUGUUGCAUCCUG

CUAUUUUCGGCCUGCAUCACAUUGGCAUGCAGAUGAGAAUUGCCAUGUUUU

CCCUGAUCUACAAGAAAACUCUGAAGCUCUCGAGCCGCGUGCUUGACAAGA

UUUCCAUCGGCCAGCUCGUGUCCCUGCUCUCCAACAAUCUGAACAAGUUCG

ACGAGGGCCUCGCCCUGGCCCACUUCGUGUGGAUCGCCCCUCUGCAAGUGG

CGCUUCUGAUGGGCCUGAUCUGGGAGCUGCUGCAAGCCUCGGCAUUCUGUG

GGCUUGGAUUCCUGAUCGUGCUGGCACUGUUCCAGGCCGGACUGGGGCGGA

UGAUGAUGAAGUACAGGGACCAGAGAGCCGGAAAGAUUUCCGAACGGCUGG

-continued

UGAUCACUUCGGAAAUGAUCGAAAACAUCCAGUCAGUGAAGGCCUACUGCU
GGGAAGAGGCCAUGGAAAAGAUGAUUGAAAACCUCCGGCAAACCGAGCUGA
AGCUGACCCGCAAGGCCGCUUACGUGCGCUAUUUCAACUCGUCCGCUUUCU
UCUUCUCCGGGUUCUUCGUGGUGUUUCUCUCCGUGCUCCCCUACGCCCUGA
UUAAGGGAAUCAUCCUCAGGAAGAUCUUCACCACCAUUUCCUUCUGUAUCG
UGCUCCGCAUGGCCGUGACCCGGCAGUUCCCAUGGGCCGUGCAGACUUGGU
ACGACUCCCUGGGAGCCAUUAACAAGAUCCAGGACUUCCUUCAAAAGCAGG
AGUACAAGACCCUCGAGUACAACCUGACUACUACCGAGGUCGUGAUGGAAA
ACGUCACCGCCUUUUGGGAGGAGGGAUUUGGCGAACUGUUCGAGAAGGCCA
AGCAGAACAACAACAACCGCAAGACCUCGAACGGUGACGACUCCCUCUUCU
UUUCAAACUUCAGCCUGCUCGGGACGCCCGUGCUGAAGGACAUUAACUUCA
AGAUCGAAAGAGGACAGCUCCUGGCGGUGGCCGGAUCGACCGGAGCCGGAA
AGACUUCCCUGCUGAUGGUGAUCAUGGGAGAGCUUGAACCUAGCGAGGGAA
AGAUCAAGCACUCCGGCCGCAUCAGCUUCUGUAGCCAGUUUUCCUGGAUCA
UGCCCGGAACCAUUAAGGAAAACAUCAUCUUCGGCGUGUCCUACGAUGAAU
ACCGCUACCGGUCCGUGAUCAAAGCCUGCCAGCUGGAAGAGGAUAUUUCAA
AGUUCGCGGAGAAAGAUAACAUCGUGCUGGGCGAAGGGGGUAUUACCUUGU
CGGGGGGCCAGCGGGCUAGAAUCUCGCUGGCCAGAGCCGUGUAUAAGGACG
CCGACCUGUAUCUCCUGGACUCCCCCUUCGGAUACCUGGACGUCCUGACCG
AAAAGGAGAUCUUCGAAUCGUGCGUGUGCAAGCUGAUGGCUAACAAGACUC
GCAUCCUCGUGACCUCCAAAAUGGAGCACCUGAAGAAGGCAGACAAGAUUC
UGAUUCUGCAUGAGGGGUCCUCCUACUUUUACGGCACCUUCUCGGAGUUGC
AGAACUUGCAGCCCGACUUCUCAUCGAAGCUGAUGGGUUGCGACAGCUUCG
ACCAGUUCUCCGCCGAAAGAAGGAACUCGAUCCUGACGGAAACCUUGCACC
GCUUCUCUUUGGAAGGCGACGCCCCUGUGUCAUGGACCGAGACUAAGAAGC
AGAGCUUCAAGCAGACCGGGGAAUUCGGCGAAAAGAGGAAGAACAGCAUCU
UGAACCCCAUUAACUCCAUCCGCAAGUUCUCAAUCGUGCAAAAGACGCCAC
UGCAGAUGAACGGCAUUGAGGAGGACUCCGACGAACCCCUUGAGAGGCGCC
UGUCCCUGGUGCCGGACAGCGAGCAGGGAGAAGCCAUCCUGCCUCGGAUUU
CCGUGAUCUCCACUGGUCCGACGCUCCAAGCCCGGCGGCGGCAGUCCGUGC
UGAACCUGAUGACCCACAGCGUGAACCAGGGCCAAAACAUUCACCGCAAGA
CUACCGCAUCCACCCGGAAAGUGUCCCUGGCACCUCAAGCGAAUCUUACCG
AGCUCGACAUCUACUCCCGGAGACUGUCGCAGGAAACCGGGCUCGAAAUUU
CCGAAGAAAUCAACGAGGAGGAUCUGAAAGAGUGCUUCUUCGACGAUAUGG
AGUCGAUACCCGCCGUGACGACUUGGAACACUUAUCUGCGGUACAUCACUG
UGCACAAGUCAUUGAUCUUCGUGCUGAUUUGGUGCCUGGUGAUUUUCCUGG
CCGAGGUCGCGGCCUCACUGGUGGUGCUCUGGCUGUUGGGAAACACGCCUC
UGCAAGACAAGGGAAACUCCACGCACUCGAGAAACAACAGCUAUGCCGUGA
UUAUCACUUCCACCUCCUCUUAUUACGUGUUCUACAUCUACGUCGGAGUGG
CGGAUACCCUGCUCGCGAUGGGUUUCUUCAGAGGACUGCCGCUGGUCCACA
CCUUGAUCACCGUCAGCAAGAUUCUUCACCACAAGAUGUUGCAUAGCGUGC
UGCAGGCCCCCAUGUCCACCCUCAACACUCUGAAGGCCGGAGGCAUUCUGA
ACAGAUUCUCCAAGGACAUCGCUAUCCUGGACGAUCUCCUGCCGCUUACCA
UCUUUGACUUCAUCCAGCUGCUGCUGAUCGUGAUUGGAGCAAUCGCAGUGG
UGGCGGUGCUGCAGCCUUACAUUUUCGUGGCCACUGUGCCGGUCAUUGUGG
CGUUCAUCAUGCUGCGGGCCUACUUCCUCCAAACCAGCCAGCAGCUGAAGC
AACUGGAAUCCGAGGGACGAUCCCCCAUCUUCACUCACCUUGUGACGUCGU
UGAAGGGACUGUGGACCCUCCGGGCUUUCGGACGGCAGCCCUACUUCGAAA
CCCUCUUCCACAAGGCCCUGAACCUCCACACCGCCAAUUGGUUCCUGUACC
UGUCCACCCUGCGGUGGUUCCAGAUGCGCAUCGAGAUGAUUUUCGUCAUCU
UCUUCAUCGCGGUCACAUUCAUCAGCAUCCUGACUACCGGAGAGGGAGAGG
GACGGGUCGGAAUAAUCCUGACCCUCGCCAUGAACAUUAUGAGCACCCUGC
AGUGGGCAGUGAACAGCUCGAUCGACGUGGACAGCCUGAUGCGAAGCGUCA
GCCGCGUGUUCAAGUUCAUCGACAUGCCUACUGAGGGAAAACCCACUAAGU
CCACUAAGCCCUACAAAAAUGGCCAGCUGAGCAAGGUCAUGAUCAUCGAAA
ACUCCCACGUGAAGAAGGACGAUAUUUGGCCCUCCGGAGGUCAAAUGACCG
UGAAGGACCUGACCGCAAAGUACACCGAGGGAGGAAACGCCAUUCUCGAAA
ACAUCAGCUUCUCCAUUUCGCCGGGACAGCGGGUCGGCCUUCUCGGGCGGA
CCGGUUCCGGGAAGUCAACUCUGCUGUCGGCUUUCCUCCGGCUGCUGAAUA
CCGAGGGGGAAAUCCAAAUUGACGGCGUGUCUUGGGAUUCCAUUACUCUGC
AGCAGUGGCGGAAGGCCUUCGGCGUGAUCCCCCAGAAGGUGUUCAUCUUCU
CGGGUACCUUCCGGAAGAACCUGGAUCCUUACGAGCAGUGGAGCGACCAAG
AAAUCUGGAAGGUCGCCGACGAGGUCGGCCUGCGCUCCGUGAUUGAACAAU
UUCCUGGAAAGCUGGACUUCGUGCUCGUCGACGGGGGAUGUGUCCUGUCGC
ACGGACAUAAGCAGCUCAUGUGCCUCGCACGGUCCGUGCUCUCCAAGGCCA
AGAUUCUGCUGCUGGACGAACCUUCGGCCCACCUGGAUCCGGUCACCUACC
AGAUCAUCAGGAGGACCCUGAAGCAGGCCUUUGCCGAUUGCACCGUGAUUC
UCUGCGAGCACCGCAUCGAGGCCAUGCUGGAGUGCCAGCAGUUCCUGGUCA
UCGAGGAGAACAAGGUCCGCCAAUACGACUCCAUUCAAAAGCUCCUCAACG
AGCGGUCGCUGUUCAGACAAGCUAUUUCACCGUCCGAUAGAGUGAAGCUCU
UCCCGCAUCGGAACAGCUCAAAGUGCAAAUCGAAGCCGCAGAUCGCAGCCU
UGAAGGAAGAGACUGAGGAAGAGGUGCAGGACACCCGGCUUUAACGGGUGG
CAUCCCUGUGACCCCUCCCCAGUGCCUCUCCUGGCCCUGGAAGUUGCCACU
CCAGUGCCCACCAGCCUUGUCCUAAUAAAAUUAAGUUGCAUCAAGCU

In one embodiment, another full-length codon-optimized human CFTR mRNA sequence is:

(SEQ ID NO: 9)

GGACAGAUCGCCUGGAGACGCCAUCCACGCUGUUUUGACCUCCAUAGAAGA
CACCGGGACCGAUCCAGCCUCCGCGGCCGGGAACGGUGCAUUGGAACGCGG
AUUCCCCGUGCCAAGAGUGACUCACCGUCCUUGACACGAUGCAACGCUCUC
CUCUUGAAAAGGCCUCGGUGGUGUCCAAGCUCUUCUUCUCGUGGACUAGAC

-continued

CCAUCCUGAGAAAGGGGUACAGACAGCGCUUGGAGCUGUCCGAUAUCUAUC
AAAUCCCUUCCGUGGACUCCGCGGACAACCUGUCCGAGAAGCUCGAGAGAG
AAUGGGACAGAGAACUCGCCUCAAAGAAGAACCCGAAGCUGAUUAAUGCGC
UUAGGCGGUGCUUUUUCUGGCGGUUCAUGUUCUACGGCAUCUUCCUCUACC
UGGGAGAGGUCACCAAGGCCGUGCAGCCCCUGUUGCUGGGACGGAUUAUUG
CCUCCUACGACCCCGACAACAAGGAAGAAAGAAGCAUCGCUAUCUACUUGG
GCAUCGGUCUGUGCCUGCUUUUCAUCGUCCGGACCCUCUUGUUGCAUCCUG
CUAUUUUCGGCCUGCAUCACAUUGGCAUGCAGAUGAGAAUUGCCAUGUUUU
CCCUGAUCUACAAGAAAACUCUGAAGCUCUCGAGCCGCGUGCUUGACAAGA
UUUCCAUCGGCCAGCUCGUGUCCCUGCUCUCCAACAAUCUGAACAAGUUCG
ACGAGGGCCUCGCCCUGGCCCACUUCGUGUGGAUCGCCCCUCUGCAAGUGG
CGCUUCUGAUGGGCCUGAUCUGGGAGCUGCUGCAAGCCUCGGCAUUCUGUG
GGCUUGGAUUCCUGAUCGUGCUGGCACUGUUCCAGGCCGGACUGGGGCGGA
UGAUGAUGAAGUACAGGGACCAGAGAGCCGGAAAGAUUUCCGAACGGCUGG
UGAUCACUUCGGAAAUGAUCGAAAACAUCCAGUCAGUGAAGGCCUACUGCU
GGGAAGAGGCCAUGGAAAAGAUGAUUGAAAACCUCCGGCAAACCGAGCUGA
AGCUGACCCGCAAGGCCGCUUACGUGCGCUAUUUCAACUCGUCCGCUUUCU
UCUUCUCCGGGUUCUUCGUGGUGUUUCUCUCCGUGCUCCCCUACGCCCUGA
UUAAGGGAAUCAUCCUCAGGAAGAUCUUCACCACCAUUUCCUUCUGUAUCG
UGCUCCGCAUGGCCGUGACCCGGCAGUUCCCAUGGGCCGUGCAGACUUGGU
ACGACUCCCUGGGAGCCAUUAACAAGAUCCAGGACUUCCUUCAAAAGCAGG
AGUACAAGACCCUCGAGUACAACCUGACUACUACCGAGGUCGUGAUGGAAA
ACGUCACCGCCUUUUGGGAGGAGGGAUUUGGCGAACUGUUCGAGAAGGCCA
AGCAGAACAACAACAACCGCAAGACCUCGAACGGUGACGACUCCCUCUUCU
UUUCAAACUUCAGCCUGCUCGGGACGCCCGUGCUGAAGGACAUUAACUUCA
AGAUCGAAAGAGGACAGCUCCUGGCGGUGGCCGGAUCGACCGGAGCCGGAA
AGACUUCCCUGCUGAUGGUGAUCAUGGGAGAGCUUGAACCUAGCGAGGGAA
AGAUCAAGCACUCCGGCCGCAUCAGCUUCUGUAGCCAGUUUUCCUGGAUCA
UGCCCGGAACCAUUAAGGAAAACAUCAUCUUCGGCGUGUCCUACGAUGAAU
ACCGCUACCGGUCCGUGAUCAAAGCCUGCCAGCUGGAAGAGGAUAUUUCAA
AGUUCGCGGAGAAAGAUAACAUCGUGCUGGGCGAAGGGGGUAUUACCUUGU
CGGGGGGCCAGCGGGCUAGAAUCUCGCUGGCCAGAGCCGUGUAUAAGGACG
CCGACCUGUAUCUCCUGGACUCCCCCUUCGGAUACCUGGACGUCCUGACCG
AAAAGGAGAUCUUCGAAUCGUGCGUGUGCAAGCUGAUGGCUAACAAGACUC
GCAUCCUCGUGACCUCCAAAAUGGAGCACCUGAAGAAGGCAGACAAGAUUC
UGAUUCUGCAUGAGGGGUCCUCCUACUUUUACGGCACCUUCUCGGAGUUGC
AGAACUUGCAGCCCGACUUCUCAUCGAAGCUGAUGGGUUGCGACAGCUUCG
ACCAGUUCUCCGCCGAAAGAAGGAACUCGAUCCUGACGGAAACCUUGCACC
GCUUCUCUUUGGAAGGCGACGCCCCUGUGUCAUGGACCGAGACUAAGAAGC
AGAGCUUCAAGCAGACCGGGGAAUUCGGCGAAAAGAGGAAGAACAGCAUCU
UGAACCCCAUUAACUCCAUCCGCAAGUUCUCAAUCGUGCAAAAGACGCCAC
UGCAGAUGAACGGCAUUGAGGAGGACUCCGACGAACCCCUUGAGAGGCGCC
UGUCCCUGGUGCCGGACAGCGAGCAGGGAGAAGCCAUCCUGCCUCGGAUUU
CCGUGAUCUCCACUGGUCCGACGCUCCAAGCCCGGCGGCGGCAGUCCGUGC
UGAACCUGAUGACCCACAGCGUGAACCAGGGCCAAAACAUUCACCGCAAGA
CUACCGCAUCCACCCGGAAAGUGUCCCUGGCACCUCAAGCGAAUCUUACCG
AGCUCGACAUCUACUCCCGGAGACUGUCGCAGGAAACCGGGCUCGAAAUUU
CCGAAGAAAUCAACGAGGAGGAUCUGAAAGAGUGCUUCUUCGACGAUAUGG
AGUCGAUACCCGCCGUGACGACUUGGAACACUUAUCUGCGGUACAUCACUG
UGCACAAGUCAUUGAUCUUCGUGCUGAUUUGGUGCCUGGUGAUUUUCCUGG
CCGAGGUCGCGGCCUCACUGGUGGUGCUCUGGCUGUUGGGAAACACGCCUC
UGCAAGACAAGGGAAACUCCACGCACUCGAGAAACAACAGCUAUGCCGUGA
UUAUCACUUCCACCUCCUCUUAUUACGUGUUCUACAUCUACGUCGGAGUGG
CGGAUACCCUGCUCGCGAUGGGUUUCUUCAGAGGACUGCCGCUGGUCCACA
CCUUGAUCACCGUCAGCAAGAUUCUUCACCACAAGAUGUUGCAUAGCGUGC
UGCAGGCCCCCAUGUCCACCCUCAACACUCUGAAGGCCGGAGGCAUUCUGA
ACAGAUUCUCCAAGGACAUCGCUAUCCUGGACGAUCUCCUGCCGCUUACCA
UCUUUGACUUCAUCCAGCUGCUGCUGAUCGUGAUUGGAGCAAUCGCAGUGG
UGGCGGUGCUGCAGCCUUACAUUUUCGUGGCCACUGUGCCGGUCAUUGUGG
CGUUCAUCAUGCUGCGGGCCUACUUCCUCCAAACCAGCCAGCAGCUGAAGC
AACUGGAAUCCGAGGGACGAUCCCCCAUCUUCACUCACCUUGUGACGUCGU
UGAAGGGACUGUGGACCCUCCGGGCUUUCGGACGGCAGCCCUACUUCGAAA
CCCUCUUCCACAAGGCCCUGAACCUCCACACCGCCAAUUGGUUCCUGUACC
UGUCCACCCUGCGGUGGUUCCAGAUGCGCAUCGAGAUGAUUUUCGUCAUCU
UCUUCAUCGCGGUCACAUUCAUCAGCAUCCUGACUACCGGAGAGGGAGAGG
GACGGGUCGGAAUAAUCCUGACCCUCGCCAUGAACAUUAUGAGCACCCUGC
AGUGGGCAGUGAACAGCUCGAUCGACGUGGACAGCCUGAUGCGAAGCGUCA
GCCGCGUGUUCAAGUUCAUCGACAUGCCUACUGAGGGAAAACCCACUAAGU
CCACUAAGCCCUACAAAAAUGGCCAGCUGAGCAAGGUCAUGAUCAUCGAAA
ACUCCCACGUGAAGAAGGACGAUAUUUGGCCCUCCGGAGGUCAAAUGACCG
UGAAGGACCUGACCGCAAAGUACACCGAGGGAGGAAACGCCAUUCUCGAAA
ACAUCAGCUUCUCCAUUUCGCCGGGACAGCGGGUCGGCCUUCUCGGGCGGA
CCGGUUCCGGGAAGUCAACUCUGCUGUCGGCUUUCCUCCGGCUGCUGAAUA
CCGAGGGGGAAAUCCAAAUUGACGGCGUGUCUUGGGAUUCCAUUACUCUGC
AGCAGUGGCGGAAGGCCUUCGGCGUGAUCCCCCAGAAGGUGUUCAUCUUCU
CGGGUACCUUCCGGAAGAACCUGGAUCCUUACGAGCAGUGGAGCGACCAAG
AAAUCUGGAAGGUCGCCGACGAGGUCGGCCUGCGCUCCGUGAUUGAACAAU
UUCCUGGAAAGCUGGACUUCGUGCUCGUCGACGGGGGAUGUGUCCUGUCGC
ACGGACAUAAGCAGCUCAUGUGCCUCGCACGGUCCGUGCUCUCCAAGGCCA
AGAUUCUGCUGCUGGACGAACCUUCGGCCCACCUGGAUCCGGUCACCUACC
AGAUCAUCAGGAGGACCCUGAAGCAGGCCUUUGCCGAUUGCACCGUGAUUC

-continued

UCUGCGAGCACCGCAUCGAGGCCAUGCUGGAGUGCCAGCAGUUCCUGGUCA

UCGAGGAGAACAAGGUCCGCCAAUACGACUCCAUUCAAAAGCUCCUCAACG

AGCGGUCGCUGUUCAGACAAGCUAUUUCACCGUCCGAUAGAGUGAAGCUCU

UCCCGCAUCGGAACAGCUCAAAGUGCAAAUCGAAGCCGCAGAUCGCAGCCU

UGAAGGAAGAGACUGAGGAAGAGGUGCAGGACACCCGGCUUUAAGGGUGGC

AUCCCUGUGACCCCUCCCCAGUGCCUCUCCUGGCCCUGGAAGUUGCCACUC

CAGUGCCCACCAGCCUUGUCCUAAUAAAAUUAAGUUGCAUCAAAGCU

In one embodiment, a codon-optimized human CFTR mRNA sequence includes SEQ ID NO: 2.

In one embodiment, a full-length codon-optimized human CFTR mRNA sequence is:

(SEQ ID NO: 10)

GGACAGAUCGCCUGGAGACGCCAUCCACGCUGUUUUGACCUCCAUAGAAGA

CACCGGGACCGAUCCAGCCUCCGCGGCCGGGAACGGUGCAUUGGAACGCGG

AUUCCCCGUGCCAAGAGUGACUCACCGUCCUUGACACGAUGCAGCGGUCCC

CGCUCGAAAAGGCCAGUGUCGUGUCCAAACUCUUCUUCUCAUGGACUCGGC

CUAUCCUUAGAAAGGGGUAUCGGCAGAGGCUUGAGUUGUCUGACAUCUACC

AGAUCCCCUCGGUAGAUUCGGCGGAUAACCUCUCGGAGAAGCUCGAACGGG

AAUGGGACCGCGAACUCGCGUCUAAGAAAAACCCGAAGCUCAUCAACGCAC

UGAGAAGGUGCUUCUUCUGGCGGUUCAUGUUCUACGGUAUCUUCUUGUAUC

UCGGGGAGGUCACAAAAGCAGUCCAACCCCUGUUGUUGGGUCGCAUUAUCG

CCUCGUACGACCCCGAUAACAAAGAAGAACGGAGCAUCGCGAUCUACCUCG

GGAUCGGACUGUGUUUGCUUUUCAUCGUCAGAACACUUUUGUUGCAUCCAG

CAAUCUUCGGCCUCCAUCACAUCGGUAUGCAGAUGCGAAUCGCUAUGUUUA

GCUUGAUCUACAAAAAGACACUGAAACUCUCGUCGCGGGUGUUGGAUAAGA

UUUCCAUCGGUCAGUUGGUGUCCCUGCUUAGUAAUAACCUCAACAAAUUCG

AUGAGGGACUGGCGCUGGCACAUUUCGUGUGGAUUGCCCCGUUGCAAGUCG

CCCUUUUGAUGGGCCUUAUUUGGGAGCUGUUGCAGGCAUCUGCCUUUUGUG

GCCUGGGAUUUCUGAUUGUGUUGGCAUUGUUUCAGGCUGGGCUUGGGCGGA

UGAUGAUGAAGUAUCGCGACCAGAGAGCGGGUAAAAUCUCGGAAAGACUCG

UCAUCACUUCGGAAAUGAUCGAAAACAUCCAGUCGGUCAAAGCCUAUUGCU

GGGAAGAAGCUAUGGAGAAGAUGAUUGAAAACCUCCGCCAAACUGAGCUGA

AACUGACCCGCAAGGCGGCGUAUGUCCGGUAUUUCAAUUCGUCAGCGUUCU

UCUUUUCCGGGUUCUUCGUUGUCUUUCUCUCGGUUUUGCCUUAUGCCUUGA

UUAAGGGGAUUAUCCUCCGCAAGAUUUUCACCACGAUUUCGUUCUGCAUUG

UAUUGCGCAUGGCAGUGACACGGCAAUUUCCGUGGGCCGUGCAGACAUGGU

AUGACUCGCUUGGAGCGAUCAACAAAAUCCAAGACUUCUUGCAAAAGCAAG

AGUACAAGACCCUGGAGUACAAUCUUACUACUACGGAGGUAGUAAUGGAGA

AUGUGACGGCUUUUUGGGAAGAGGGUUUUGGAGAACUGUUUGAGAAAGCAA

AGCAGAAUAACAACAACCGCAAGACCUCAAAUGGGGACGAUUCCCUGUUUU

UCUCGAACUUCUCCCUGCUCGGAACACCCGUGUUGAAGGACAUCAAUUUCA

-continued

AGAUUGAGAGGGGACAGCUUCUCGCGGUAGCGGGAAGCACUGGUGCGGGAA

AAACUAGCCUCUUGAUGGUGAUUAUGGGGGAGCUUGAGCCCAGCGAGGGGA

AGAUUAAACACUCCGGGCGUAUCUCAUUCUGUAGCCAGUUUUCAUGGAUCA

UGCCCGGAACCAUUAAAGAGAACAUCAUUUUCGGAGUAUCCUAUGAUGAGU

ACCGAUACAGAUCGGUCAUUAAGGCGUGCCAGUUGGAAGAGGACAUUUCUA

AGUUCGCCGAGAAGGAUAACAUCGUCUUGGGAGAAGGGGGUAUUACAUUGU

CGGGAGGGCAGCGAGCGCGGAUCAGCCUCGCGAGAGCGGUAUACAAAGAUG

CAGAUUUGUAUCUGCUUGAUUCACCGUUUGGAUACCUCGACGUAUUGACAG

AAAAAGAAAUCUUCGAGUCGUGCGUGUGUAAACUUAUGGCUAAUAAGACGA

GAAUCCUGGUGACAUCAAAAAUGGAACACCUUAAGAAGGCGGACAAGAUCC

UGAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUCG

ACCAGUUCAGCGCGGAACGGCGGAACUCGAUCUUGACGGAAACGCUGCACC

GAUUCUCGCUUGAGGGUGAUGCCCCGGUAUCGUGGACCGAGACAAAGAAGC

AGUCGUUUAAGCAGACAGGAGAAUUUGGUGAGAAAAGAAAGAACAGUAUCU

UGAAUCCUAUUAACUCAAUUCGCAAGUUCUCAAUCGUCCAGAAAACUCCAC

UGCAGAUGAAUGGAAUUGAAGAGGAUUCGGACGAACCCCUGGAGCGCAGGC

UUAGCCUCGUGCCGGAUUCAGAGCAAGGGGAGGCCAUUCUUCCCCGGAUUU

CGGUGAUUUCAACCGGACCUACACUUCAGGCGAGGCGAAGGCAAUCCGUGC

UCAACCUCAUGACGCAUUCGGUAAACCAGGGGCAAAACAUUCACCGCAAAA

CGACGGCCUCAACGAGAAAAGUGUCACUUGCACCCCAGGCGAAUUUGACUG

AACUCGACAUCUACAGCCGUAGGCUUUCGCAAGAAACCGGACUUGAGAUCA

GCGAAGAAAUCAAUGAAGAAGAUUUGAAAGAGUGUUUCUUUGAUGACAUGG

AAUCAAUCCCAGCGGUGACAACGUGGAACACAUACUUGCGUUACAUCACGG

UGCACAAGUCCUUGAUUUUCGUCCUCAUCUGGUGUCUCGUGAUCUUUCUCG

CUGAGGUCGCAGCGUCACUUGUGGUCCUCUGGCUGCUUGGUAAUACGCCCU

UGCAAGACAAAGGCAAUUCUACACACUCAAGAAACAAUUCCUAUGCCGUGA

UUAUCACUUCUACAAGCUCGUAUUACGUGUUUUACAUCUACGUAGGAGUGG

CCGACACUCUGCUCGCGAUGGGUUUCUUCCGAGGACUCCCACUCGUUCACA

CGCUUAUCACUGUCUCCAAGAUUCUCCACCAUAAGAUGCUUCAUAGCGUAC

UGCAGGCUCCCAUGUCCACCUUGAAUACGCUCAAGGCGGGAGGUAUUUUGA

AUCGCUUCUCAAAAGAUAUUGCAAUUUUGGAUGACCUUCUGCCCCUGACGA

UCUUCGACUUCAUCCAGUUGUUGCUGAUCGUGAUUGGGGCUAUUGCAGUAG

UCGCUGUCCUCCAGCCUUACAUUUUUGUCGCGACCGUUCCGGUGAUCGUGG

CGUUUAUCAUGCUGCGGGCCUAUUUCUUGCAGACGUCACAGCAGCUUAAGC

AACUGGAGUCUGAAGGGAGGUCGCCUAUCUUUACGCAUCUUGUGACCAGUU

UGAAGGGAUUGUGGACGUUGCGCGCCUUUGGCAGGCAGCCCUACUUUGAAA

CACUGUUCCACAAAGCGCUGAAUCUCCAUACGGCAAAUUGGUUUUUGUAUU

UGAGUACCCUCCGAUGGUUUCAGAUGCGCAUUGAGAUGAUUUUUGUGAUCU

UCUUUAUCGCGGUGACUUUUAUCUCCAUCUUGACCACGGGAGAGGGCGAGG

GACGGGUCGGUAUUAUCCUGACACUCGCCAUGAACAUUAUGAGCACUUUGC

-continued

AGUGGGCAGUGAACAGCUCGAUUGAUGUGGAUAGCCUGAUGAGGUCCGUUU

CGAGGGUCUUUAAGUUCAUCGACAUGCCGACGGAGGGAAAGCCCACAAAAA

GUACGAAACCCUAUAAGAAUGGGCAAUUGAGUAAGGUAAUGAUCAUCGAGA

ACAGUCACGUGAAGAAGGAUGACAUCUGGCCUAGCGGGGGUCAGAUGACCG

UGAAGGACCUGACGGCAAAAUACACCGAGGGAGGGAACGCAAUCCUUGAAA

ACAUCUCGUUCAGCAUUAGCCCCGGUCAGCGUGUGGGGUUGCUCGGGAGGA

CCGGGUCAGGAAAAUCGACGUUGCUGUCGGCCUUCUUGAGACUUCUGAAUA

CAGAGGGUGAGAUCCAGAUCGACGGCGUUUCGUGGGAUAGCAUCACCUUGC

AGCAGUGGCGGAAAGCGUUUGGAGUAAUCCCCCAAAAGGUCUUUAUCUUUA

GCGGAACCUUCCGAAAGAAUCUCGAUCCUUAUGAACAGUGGUCAGAUCAAG

AGAUUUGGAAAGUCGCGGACGAGGUUGGCCUUCGGAGUGUAAUCGAGCAGU

UUCCGGGAAAACUCGACUUUGUCCUUGUAGAUGGGGGAUGCGUCCUGUCGC

AUGGGCACAAGCAGCUCAUGUGCCUGGCGCGAUCCGUCCUCUCUAAAGCGA

AAAUUCUUCUCUUGGAUGAACCUUCGGCCCAUCUGGACCCGGUAACGUAUC

AGAUCAUCAGAAGGACACUUAAGCAGGCGUUUGCCGACUGCACGGUGAUUC

UCUGUGAGCAUCGUAUCGAGGCCAUGCUCGAAUGCCAGCAAUUUCUUGUCA

UCGAAGAGAAUAAGGUCCGCCAGUACGACUCCAUCCAGAAGCUGCUUAAUG

AGAGAUCAUUGUUCCGGCAGGCGAUUUCACCAUCCGAUAGGGUGAAACUUU

UUCCACACAGAAAUUCGUCGAAGUGCAAGUCCAAACCGCAGAUCGCGGCCU

UGAAAGAAGAGACUGAAGAAGAAGUUCAAGACACGCGUCUUUAACGGGUGG

CAUCCCUGUGACCCCUCCCCAGUGCCUCUCCUGGCCCUGGAAGUUGCCACU

CCAGUGCCCACCAGCCUUGUCCUAAUAAAAUUAAGUUGCAUCAAGCU

In one embodiment, another full-length codon-optimized human CFTR mRNA sequence is:

(SEQ ID NO: 11)

GGACAGAUCGCCUGGAGACGCCAUCCACGCUGUUUUGACCUCCAUAGAAGA

CACCGGGACCGAUCCAGCCUCCGCGGCCGGGAACGGUGCAUUGGAACGCGG

AUUCCCCGUGCCAAGAGUGACUCACCGUCCUUGACACGAUGCAGCGGUCCC

CGCUCGAAAAGGCCAGUGUCGUGUCCAAACUCUUCUUCUCAUGGACUCGGC

CUAUCCUUAGAAAGGGGUAUCGGCAGAGGCUUGAGUUGUCUGACAUCUACC

AGAUCCCCUCGGUAGAUUCGGCGGAUAACCUCUCGGAGAAGCUCGAACGGG

AAUGGGACCGCGAACUCGCGUCUAAGAAAAACCCGAAGCUCAUCAACGCAC

UGAGAAGGUGCUUCUUCUGGCGGUUCAUGUUCUACGGUAUCUUCUUGUAUC

UCGGGGAGGUCACAAAAGCAGUCCAACCCCUGUUGUUGGGUCGCAUUAUCG

CCUCGUACGACCCCGAUAACAAAGAAGAACGGAGCAUCGCGAUCUACCUCG

GGAUCGGACUGUGUUUGCUUUUCAUCGUCAGAACACUUUUGUUGCAUCCAG

CAAUCUUCGGCCUCCAUCACAUCGGUAUGCAGAUGCGAAUCGCUAUGUUUA

GCUUGAUCUACAAAAAGACACUGAAACUCUCGUCGCGGGUGUUGGAUAAGA

UUUCCAUCGGUCAGUUGGUGUCCCUGCUUAGUAAUAACCUCAACAAAUUCG

AUGAGGGACUGGCGCUGGCACAUUUCGUGUGGAUUGCCCCGUUGCAAGUCG

-continued

CCCUUUUGAUGGGCCUUAUUUGGGAGCUGUUGCAGGCAUCUGCCUUUUGUG

GCCUGGGAUUUCUGAUUGUGUUGGCAUUGUUUCAGGCUGGGCUUGGGCGGA

UGAUGAUGAAGUAUCGCGACCAGAGAGCGGGUAAAAUCUCGGAAAGACUCG

UCAUCACUUCGGAAAUGAUCGAAAACAUCCAGUCGGUCAAAGCCUAUUGCU

GGGAAGAAGCUAUGGAGAAGAUGAUUGAAAACCUCCGCCAAACUGAGCUGA

AACUGACCCGCAAGGCGGCGUAUGUCCGGUAUUUCAAUUCGUCAGCGUUCU

UCUUUUCCGGGUUCUUCGUUGUCUUUCUCUCGGUUUUGCCUUAUGCCUUGA

UUAAGGGGAUUAUCCUCCGCAAGAUUUUCACCACGAUUUCGUUCUGCAUUG

UAUUGCGCAUGGCAGUGACACGGCAAUUUCCGUGGGCCGUGCAGACAUGGU

AUGACUCGCUUGGAGCGAUCAACAAAAUCCAAGACUUCUUGCAAAAGCAAG

AGUACAAGACCCUGGAGUACAAUCUUACUACUACGGAGGUAGUAAUGGAGA

AUGUGACGGCUUUUUGGGAAGAGGGUUUUGGAGAACUGUUUGAGAAAGCAA

AGCAGAAUAACAACAACCGCAAGACCUCAAAUGGGGACGAUUCCCUGUUUU

UCUCGAACUUCUCCCUGCUCGGAACACCCGUGUUGAAGGACAUCAAUUUCA

AGAUUGAGAGGGGACAGCUUCUCGCGGUAGCGGGAAGCACUGGUGCGGGAA

AAACUAGCCUCUUGAUGGUGAUUAUGGGGGAGCUUGAGCCCAGCGAGGGGA

AGAUUAAACACUCCGGGCGUAUCUCAUUCUGUAGCCAGUUUUCAUGGAUCA

UGCCCGGAACCAUUAAAGAGAACAUCAUUUUCGGAGUAUCCUAUGAUGAGU

ACCGAUACAGAUCGGUCAUUAAGGCGUGCCAGUUGGAAGAGGACAUUUCUA

AGUUCGCCGAGAAGGAUAACAUCGUCUUGGGAGAAGGGGGUAUUACAUUGU

CGGGAGGGCAGCGAGCGCGGAUCAGCCUCGCGAGAGCGGUAUACAAAGAUG

CAGAUUUGUAUCUGCUUGAUUCACCGUUUGGAUACCUCGACGUAUUGACAG

AAAAAGAAAUCUUCGAGUCGUGCGUGUGUAAACUUAUGGCUAAUAAGACGA

GAAUCCUGGUGACAUCAAAAAUGGAACACCUUAAGAAGGCGGACAAGAUCC

UGAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUCG

ACCAGUUCAGCGCGGAACGGCGGAACUCGAUCUUGACGGAAACGCUGCACC

GAUUCUCGCUUGAGGGUGAUGCCCCGGUAUCGUGGACCGAGACAAAGAAGC

AGUCGUUUAAGCAGACAGGAGAAUUUGGUGAGAAAAGAAAGAACAGUAUCU

UGAAUCCUAUUAACUCAAUUCGCAAGUUCUCAAUCGUCCAGAAAACUCCAC

UGCAGAUGAAUGGAAUUGAAGAGGAUUCGGACGAACCCCUGGAGCGCAGGC

UUAGCCUCGUGCCGGAUUCAGAGCAAGGGGAGGCCAUUCUUCCCCGGAUUU

CGGUGAUUUCAACCGGACCUACACUUCAGGCGAGGCGAAGGCAAUCCGUGC

UCAACCUCAUGACGCAUUCGGUAAACCAGGGGCAAAACAUUCACCGCAAAA

CGACGGCCUCAACGAGAAAAGUGUCACUUGCACCCCAGGCGAAUUUGACUG

AACUCGACAUCUACAGCCGUAGGCUUUCGCAAGAAACCGGACUUGAGAUCA

GCGAAGAAAUCAAUGAAGAAGAUUUGAAAGAGUGUUUCUUUGAUGACAUGG

AAUCAAUCCCAGCGGUGACAACGUGGAACACAUACUUGCGUUACAUCACGG

UGCACAAGUCCUUGAUUUUCGUCCUCAUCUGGUGUCUCGUGAUCUUUCUCG

CUGAGGUCGCAGCGUCACUUGUGGUCCUCUGGCUGCUUGGUAAUACGCCCU

UGCAAGACAAAGGCAAUUCUACACACUCAAGAAACAAUUCCUAUGCCGUGA

-continued

UUAUCACUUCUACAAGCUCGUAUUACGUGUUUUACAUCUACGUAGGAGUGG

CCGACACUCUGCUCGCGAUGGGUUUCUUCCGAGGACUCCCACUCGUUCACA

CGCUUAUCACUGUCUCCAAGAUUCUCCACCAUAAGAUGCUUCAUAGCGUAC

UGCAGGCUCCCAUGUCCACCUUGAAUACGCUCAAGGCGGGAGGUAUUUUGA

AUCGCUUCUCAAAAGAUAUUGCAAUUUUGGAUGACCUUCUGCCCCUGACGA

UCUUCGACUUCAUCCAGUUGUUGCUGAUCGUGAUUGGGGCUAUUGCAGUAG

UCGCUGUCCUCCAGCCUUACAUUUUUGUCGCGACCGUUCCGGUGAUCGUGG

CGUUUAUCAUGCUGCGGGCCUAUUUCUUGCAGACGUCACAGCAGCUUAAGC

AACUGGAGUCUGAAGGGAGGUCGCCUAUCUUUACGCAUCUUGUGACCAGUU

UGAAGGGAUUGUGGACGUUGCGCGCCUUUGGCAGGCAGCCCUACUUUGAAA

CACUGUUCCACAAAGCGCUGAAUCUCCAUACGGCAAAUUGGUUUUUGUAUU

UGAGUACCCUCCGAUGGUUUCAGAUGCGCAUUGAGAUGAUUUUUGUGAUCU

UCUUUAUCGCGGUGACUUUUAUCUCCAUCUUGACCACGGGAGAGGGCGAGG

GACGGGUCGGUAUUAUCCUGACACUCGCCAUGAACAUUAUGAGCACUUUGC

AGUGGGCAGUGAACAGCUCGAUUGAUGUGGAUAGCCUGAUGAGGUCCGUUU

CGAGGGUCUUUAAGUUCAUCGACAUGCCGACGGAGGGAAAGCCCACAAAAA

GUACGAAACCCUAUAAGAAUGGGCAAUUGAGUAAGGUAAUGAUCAUCGAGA

ACAGUCACGUGAAGAAGGAUGACAUCUGGCCUAGCGGGGGUCAGAUGACCG

UGAAGGACCUGACGGCAAAAUACACCGAGGGAGGGAACGCAAUCCUUGAAA

ACAUCUCGUUCAGCAUUAGCCCCGGUCAGCGUGUGGGGUUGCUCGGGAGGA

CCGGGUCAGGAAAAUCGACGUUGCUGUCGGCCUUCUUGAGACUUCUGAAUA

CAGAGGGUGAGAUCCAGAUCGACGGCGUUUCGUGGGAUAGCAUCACCUUGC

AGCAGUGGCGGAAAGCGUUUGGAGUAAUCCCCCAAAAGGUCUUUAUCUUUA

GCGGAACCUUCCGAAAGAAUCUCGAUCCUUAUGAACAGUGGUCAGAUCAAG

AGAUUUGGAAAGUCGCGGACGAGGUUGGCCUUCGGAGUGUAAUCGAGCAGU

UUCCGGGAAAACUCGACUUUGUCCUUGUAGAUGGGGGAUGCGUCCUGUCGC

AUGGGCACAAGCAGCUCAUGUGCCUGGCGCGAUCCGUCCUCUCUAAAGCGA

AAAUUCUUCUCUUGGAUGAACCUUCGGCCCAUCUGGACCCGGUAACGUAUC

AGAUCAUCAGAAGGACACUUAAGCAGGCGUUUGCCGACUGCACGGUGAUUC

UCUGUGAGCAUCGUAUCGAGGCCAUGCUCGAAUGCCAGCAAUUUCUUGUCA

UCGAAGAGAAUAAGGUCCGCCAGUACGACUCCAUCCAGAAGCUGCUUAAUG

AGAGAUCAUUGUUCCGGCAGGCGAUUUCACCAUCCGAUAGGGUGAAACUUU

UUCCACACAGAAAUUCGUCGAAGUGCAAGUCCAAACCGCAGAUCGCGGCCU

UGAAAGAAGAGACUGAAGAAGAAGUUCAAGACACGCGUCUUUAAGGGUGGC

AUCCCUGUGACCCCUCCCCAGUGCCUCUCCUGGCCCUGGAAGUUGCCACUC

CAGUGCCCACCAGCCUUGUCCUAAUAAAAUUAAGUUGCAUCAAAGCU

SEQ ID NO: 8, SEQ ID NO: 9, SEQ ID NO: 10, and SEQ ID NO: 11 include 5' and 3' untranslated regions framing a codon-optimized hCFTR-encoding mRNA.

In some embodiments, a suitable mRNA sequence may be an mRNA sequence a homolog or an analog of human CFTR (hCFTR) protein. For example, a homolog or an analog of hCFTR protein may be a modified hCFTR protein containing one or more amino acid substitutions, deletions, and/or insertions as compared to a wild-type or naturally-occurring hCFTR protein while retaining substantial hCFTR protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 4. In some embodiments, an mRNA suitable for the present invention encodes a protein substantially identical to hCFTR protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 4. In some embodiments, an mRNA suitable for the present invention encodes a fragment or a portion of hCFTR protein. In some embodiments, an mRNA suitable for the present invention encodes a fragment or a portion of hCFTR protein, wherein the fragment or portion of the protein still maintains CFTR activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 8 or SEQ ID NO: 9. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 2, SEQ ID NO: 10 or SEQ ID NO: 11. In some embodiments, an mRNA suitable for the present invention comprises a nucleotide sequence identical to SEQ ID NO: 1. In some embodiments, an mRNA suitable for the present invention comprises a nucleotide sequence identical to SEQ ID NO: 8. In some embodiments, an mRNA suitable for the present invention comprises a nucleotide sequence identical to SEQ ID NO: 9. In some embodiments, a suitable mRNA encodes a fusion protein comprising a full length, fragment or portion of an hCFTR protein fused to another protein (e.g., an N or C terminal fusion). In some embodiments, the protein fused to the mRNA encoding a full length, fragment or portion of an hCFTR protein encodes a signal or a cellular targeting sequence.

mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

Non-Coding Regions

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

According to various embodiments, any size mRNA may be encapsulated by provided liposomes. In some embodiments, the provided liposomes may encapsulate mRNA of greater than about 0.5 kb, 1 kb, 1.5 kb, 2 kb, 2.5 kb, 3 kb, 3.5 kb, 4 kb, 4.5 kb, or 5 kb in length.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., mRNAs encoding CFTR) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

In some embodiments, mRNAs (e.g., mRNAs encoding CFTR) include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., mRNAs encoding CFTR) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., mRNAs encoding CFTR) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), azidotriphosphates (2'-azido-2'-deoxycytidine 5'-triphosphate, 2'-azido-2'-deoxyuridine 5'-triphosphate) or 4'-thio-substituted ribonucleotides.

In some embodiments, mRNAs (e.g., mRNAs encoding CFTR) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

Alternately or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously, intravitreally) to either deliver or release mRNA over extended periods of time. Preferably, the extended-release means employed are combined with modifications made to the mRNA to enhance stability.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the lungs, liver, kidney, heart, spleen, serum, brain, skeletal muscle, lymph nodes, skin, and/or cerebrospinal fluid.

In some embodiments, a target tissue is lung. In some embodiments, a target tissue is the upper (i.e., superior) lobe of the right or left lung. In some embodiments, a target tissue is the lower (i.e., inferior) lobe of the right or left lung. In some embodiments, a target tissue is the middle lobe of the right lung.

In some embodiments, a target tissue is the apical segment of the right lung or the apicoposterior segment of the left lung. In some embodiments, a target tissue is the posterior segment of the right lung. In some embodiments, a target tissue is the anterior segment of the right or left lung. In some embodiments, a target tissue is the superior segment of the right or left lung. In some embodiments, a target tissue is the lateral basal segment of the right or left lung. In some embodiments, a target tissue is the anterior basal segment of the right lung. In some embodiments, a target tissue is the anteromedial basal segment of the left lung. In some embodiments, a target tissue is the lateral segment of the right lung. In some embodiments, a target tissue is the medial segment of the right lung. In some embodiments, a target tissue is the superior lingular segment of the left lung. In some embodiments, a target tissue is the inferior lingular segment of the left lung. In some embodiments, a target tissue is the posterior basal segment of the right or left lung. In some embodiments, a target tissue is the medial basal segment of the right lung.

In particular embodiments, a target tissue is epithelial cells in the lung. In some embodiments, a target tissue is smooth muscle cells in the lung. In some embodiment, a target tissue is pancreatic duct epithelial cells. In some embodiment, a target tissue is bile-duct epithelial cells. In some embodiment, a target tissue is epithelial cells of the salivary glands. In some embodiment, a target tissue is renal epithelial cells. In some embodiment, a target tissue is beta-S cells in sweat gland secretory coils of sweat glands. In some embodiment, a target tissue is epithelial cells of the reproductive tract.

According to various embodiments, the timing of expression of delivered mRNAs can be tuned to suit a particular medical need. In some embodiments, the expression of the protein encoded by delivered mRNA is detectable 1, 2, 3, 6, 12, 18, 24, 30, 36, 42, 48, 54, 60, 66, and/or 72 hours in serum or target tissues after a single administration of provided liposomes or compositions. In some embodiments, the expression of the protein encoded by the mRNA is detectable 1 day, 2 days, 3 days, 4 days, 5 days, 6 days, and/or 7 days in serum or target tissues after a single administration of provided liposomes or compositions. In some embodiments, the expression of the protein encoded by the mRNA is detectable 1 week, 2 weeks, 3 weeks, and/or 4 weeks in serum or target tissues after a single administration of provided liposomes or compositions. In some embodiments, the expression of the protein encoded by the mRNA is detectable after a month or longer after a single administration of provided liposomes or compositions.

In some embodiments, mRNA (e.g., encoding CFTR protein) in a formulation as provided herein (e.g. encapsulated in a lipid nanoparticle consisting of 3 distinct lipid components, one of which is a sterol-based cationic lipid) delivered to the lung (e.g., by nebulization) is expressed in lung tissue for at least 7 days, at least 14 days, at least 21 days, or at least 28 days. In some embodiments, mRNA (e.g., encoding CFTR protein) in a formulation as provided herein (e.g. encapsulated in a lipid nanoparticle consisting of 3 distinct lipid components, one of which is a sterol-based cationic lipid) delivered to the lung (e.g., by nebulization) is expressed in lung tissue for up to 7 days, up to 14 days, up to 21 days, or up to 28 days. In some embodiments, a protein (e.g., CFTR) encoded by an mRNA (e.g., encoding CFTR protein) in a formulation as provided herein (e.g. encapsulated in a lipid nanoparticle consisting of 3 distinct lipid components, one of which is a sterol-based cationic lipid) delivered to the lung (e.g., by nebulization) is expressed in lung tissue for at least 7 days, at least 14 days, at least 21 days, or at least 28 days. In some embodiments, a protein (e.g., CFTR) encoded by an mRNA (e.g., encoding CFTR protein) in a formulation as provided herein (e.g. encapsulated in a lipid nanoparticle consisting of 3 distinct lipid components, one of which is a sterol-based cationic lipid) delivered to the lung (e.g., by nebulization) is expressed in lung tissue for up to 7 days, up to 14 days, up to 21 days, or up to 28 days.

The present invention can be used to deliver mRNA at various doses. In some embodiments, an mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, an mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

EXAMPLES

While certain compounds, compositions and methods of the present invention have been described with specificity in accordance with certain embodiments, the following examples serve only to illustrate the invention and are not intended to limit the same.

Lipid Materials

The formulations described herein included a multi-component lipid mixture of varying ratios employing cationic lipids, helper lipids and PEGy-modified lipids designed to encapsulate various nucleic acid-based materials. Cationic lipids can include (but not exclusively) sterol-based cationic lipids, ICE (imidazole cholesterol ester), 1,2-dioleoyl-3- dimethylammonium-propane (DODAP), 1,2-dioleoyl-3-trimethylammonium-propane (DOTAP), 1,2-Dioleyloxy-3-dimethylaminopropane (DODMA), 1,2-di-O-octadecenyl-3-trimethylammonium propane (DOTMA), C12-200, DLinSSDMA, Target 24, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), cholesterol, etc. The PEG-modified lipids can include (but not exclusively) a poly (ethylene) glycol chain of up to 5 kDa in length covalently attached to a lipid with alkyl chain(s) of $C_6$-$C_{20}$ length.

N/P ratio is the molar ratios of the nitrogen (amine) groups of cationic carriers to those of the phosphate ones of mRNA.

Messenger RNA Material

The formulations described herein included messenger RNA (mRNA). mRNA can (but not exclusively) encode human Cystic Fibrosis Transmembrane Conductance Regulator (CFTR) and Firefly Luciferase (FFL). Exemplary mRNA coding sequences as disclosed herein include SEQ ID NO: 1, SEQ ID NO: 2, and SEQ ID NO: 3. An exemplary 5' UTR mRNA sequence as disclosed herein is SEQ ID NO: 5. Exemplary 3' UTR mRNA sequences as disclosed herein are SEQ ID NO: 6 and SEQ ID NO: 7. Exemplary full length mRNA sequences (i.e., a coding sequence plus a 5' UTR and a 3' UTR) as disclosed herein include SEQ ID NO: 8, SEQ ID NO: 9, SEQ ID NO: 10, and SEQ ID NO: 11.

Exemplary LNP Formulations Comprising Different Cationic Lipids

In some embodiments, one particular application of the novel lipid composition comprising a sterol-based cationic lipid, a helper lipid, and a PEG or PEG-modified lipid is pulmonary delivery of mRNA, such as CFTR mRNA. Lipid nanoparticle formulations composed of ICE lipid, DOPE lipid and DMG-PEG lipid (molar ratio of 60:35:5) exhibit high percent encapsulation values for mRNA, such as CFTR mRNA (>80%), as determined by fluorescence-based detection of mRNA. As shown in Table 5, this particular formulation composition is superior because conventional pH titrable cationic lipids with DOPE and DMG-PEG 2K do not show such high percent encapsulation.

TABLE 5

The encapsulation percentage of mRNA for a sterol-based cationic lipid nanoparticle formulation and other cationic lipid-based nanoparticle formulations. All lipid formulations were prepared with the composition of cationic lipid:DOPE:DMG-PEG 2K (molar ratio 60:35:5).

| pH titratable Cationic Lipid | % mRNA encapsulation |
|---|---|
| ICE | 90 |
| DODMA | 51 |
| DODAP | 49 |
| C12-200 | 39 |
| DLinSSDMA | 57 |
| Target 24 | 59 |

All of these exemplary formulations were prepared as 5 mg mRNA LNP preparations.

Formulation Example #1 (ICE Lipid)

Aliquots of 10 mg/mL ethanolic solutions of ICE, DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 90%. Size: 60 nm. PDI: 0.14.

Formulation Example #2 (DODMA Lipid)

Aliquots of 10 mg/mL ethanolic solutions of DODMA, DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL. In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 51%. Size: 62 nm. PDI: 0.18.

Formulation Example #3 (DODAP Lipid)

Aliquots of 10 mg/mL ethanolic solutions of DODAP, DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 49%. Size: 78 nm. PDI: 0.19.

Formulation Example #4 (C12-200 Lipid)

Aliquots of 10 mg/mL ethanolic solutions of C12-200, DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 39%. Size: 98 nm. PDI: 0.22.

Formulation Example #5 (DLin-SS-DMA Lipid)

Aliquots of 10 mg/mL ethanolic solutions of DLin-SS-DMA, DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 57%.

Formulation Example #6 (Target 24 Lipid)

Aliquots of 10 mg/mL ethanolic solutions of Target 24 (3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione), DOPE and DMG-PEG2K (molar ratio of 60:35:5) were mixed and diluted with ethanol to 15 mL final volume. Separately, an aqueous buffered solution (10 mM citrate/150 mM NaCl, pH 4.5) of CFTR mRNA was prepared from a 1 mg/mL stock solution so as to have a final volume of 60 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der wall forces. The resultant formulation mixture was in citrate buffer containing 20% ethanol. The formulation was subjected to a buffer exchange and the resultant formulation was adjusted to the desired mRNA concentration and stored frozen until further use. Final concentration: 0.5 mg/mL CFTR mRNA (encapsulated). % mRNA Encapsulation: 59%. Size: 92 nm. PDI: 0.24.

Exemplary ICE Formulation Protocols

A. Formulation Example—1 mg Scale, N/P=4

Aliquots of 10 mg/mL ethanolic solutions of ICE, DOPE, cholesterol and DMG-PEG2K (molar ratio of 60:35:5) were mixed and diluted with ethanol to 3 mL final volume. Separately, an aqueous buffered solution (10 mM citrate/150 mM NaCl, pH 4.5) of CFTR mRNA was prepared from a 1 mg/mL stock solution. The lipid solution was injected rapidly into the aqueous mRNA solution and shaken to yield a final suspension in 20% ethanol. The resulting nanoparticle suspension was filtered, diafiltrated, concentrated and stored frozen until further use. Final concentration of the formulation was determined at 0.5 mg/mL CFTR mRNA (encapsulated). The formulation had about 89% mRNA encapsulation (89% of the lipid nanoparticles contained mRNA) and the lipid nanoparticles had an average size of around 67 nm with polydispersibility index (PDI) of 0.19.

B. Formulation Example—15 mg Scale, N/P=2

Aliquots of 10 mg/mL ethanolic solutions of ICE, DOPE and DMG-PEG2K (molar ratio of 60:35:5) were mixed and diluted with ethanol to 45 mL final volume. Separately, an aqueous buffered solution (10 mM citrate/150 mM NaCl, pH 4.5) of CFTR mRNA was prepared from a 1 mg/mL stock solution so as to have a final volume of 180 mL.

In this process, the lipids dissolved in ethanol and the mRNA dissolved in citrate buffer were mixed using a pump system. The instantaneous mixing of the two streams resulted in formation of lipid nanoparticles, which was a self-assembly process driven by electrostatic attraction and van der Waals forces. The resultant formulation mixture was in citrate buffer containing 20% ethanol. The formulation was subjected to a buffer exchange and the resultant formulation was adjusted to the desired mRNA concentration and stored frozen until further use. Final concentration of the formulation was determined at 0.5 mg/mL CFTR mRNA (encapsulated). The lipid nanoparticles had an average size of around 70 nm with PDI of 0.17.

C. Formulation Example—15 mg Scale, N/P=4

Aliquots of 10 mg/mL ethanolic solutions of ICE, DOPE and DMG-PEG2K (molar ratio of 60:35:5) were mixed and diluted with ethanol to 45 mL final volume. Separately, an aqueous buffered solution (10 mM citrate/150 mM NaCl, pH 4.5) of CFTR mRNA was prepared from a 1 mg/mL stock solution so as to have a final volume of 180 mL.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange and the resultant formulation was adjusted to the desired mRNA concentration and stored frozen until further use. Final concentration of the formulation was determined at 0.5 mg/mL CFTR mRNA (encapsulated). The formulation had about 85% mRNA encapsulation and the lipid nanoparticles had an average size of around 65 nm with PDI of 0.13.

D. Formulation Example—30 mg Scale, N/P=4

Aliquots of 10 mg/mL ethanolic solutions of ICE, DOPE and DMG-PEG2K (molar ratio of 60:35:5) were mixed and diluted with ethanol to 90 mL final volume. Separately, an aqueous buffered solution (10 mM citrate/150 mM NaCl, pH 4.5) of CFTR mRNA was prepared from a 1 mg/mL stock solution so as to have a final volume of 360 mL.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange using TFF system and the resultant formulation was adjusted to the desired mRNA concentration and stored frozen until further use. Final concentration of the formulation was determined at 0.5 mg/mL CFTR mRNA (encapsulated). The formulation had about 86% of mRNA encapsulation and the lipid nanoparticles had an average size of around 89 nm with PDI of 0.12.

E. Formulation Example—30 mg Scale, 3% PEG, N/P=4

Aliquots of 10 mg/mL ethanolic solutions of ICE, DOPE and DMG-PEG2K (molar ratio of 60:37:3) were mixed and diluted with ethanol to 90 mL final volume. Separately, an aqueous buffered solution (10 mM citrate/150 mM NaCl, pH 4.5) of CFTR mRNA was prepared from a 1 mg/mL stock solution so as to have a final volume of 360 mL.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange using TFF system and the resultant formulation was adjusted to the desired mRNA concentration and stored frozen until further use. Final concentration of the formulation was determined at 0.5 mg/mL CFTR mRNA (encapsulated). The lipid nanoparticles had an average size of around 94 nm with PDI of 0.15.

F. Formulation Example—60 mg Scale, N/P=4

Aliquots of 10 mg/mL ethanolic solutions of ICE, DOPE and DMG-PEG2K (molar ratio of 60:35:5) were mixed and diluted with ethanol to 180 mL final volume. Separately, an aqueous buffered solution (10 mM citrate/150 mM NaCl, pH 4.5) of CFTR mRNA was prepared from a 1 mg/mL stock solution so as to have a final volume of 720 mL.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange using TFF system and the resultant formulation was adjusted to the desired mRNA concentration and stored frozen until further use. Final concentration of the formulation was determined at 0.5 mg/mL CFTR STOP mRNA (encapsulated). The formulation had about 97% mRNA encapsulation and the lipid nanoparticles had an average size of around 67 nm with PDI of 0.12.

G. Formulation Example—3.5 Gram Scale, N/P=4

Aliquots of 10 mg/mL ethanolic solutions of ICE, DOPE and DMG-PEG2K (molar ratio of 60:35:5) were mixed and diluted with ethanol to 42 L final volume. Separately, an aqueous buffered solution (10 mM citrate/150 mM NaCl, pH 4.5) of CFTR mRNA was prepared from a 1 mg/mL stock solution so as to have a final volume of 42 L.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange using TFF system and the resultant formulation is adjusted to the desired mRNA concentration and stored frozen until further use. Final concentration of the formulation was determined at 0.5 mg/mL CFTR mRNA (encapsulated). The formulation had about 91% mRNA encapsulation and the lipid nanoparticles had an average size of around 50 nm with PDI of 0.17.

H. Formulation Example—200 mg Scale, N/P=4

Aliquots of 10 mg/mL ethanolic solutions of ICE, DOPE and DMG-PEG2K (molar ratio of 60:35:5) were mixed and diluted with ethanol to 600 mL final volume. Separately, an aqueous buffered solution (10 mM citrate/150 mM NaCl, pH 4.5) of FFL mRNA was prepared from a 1 mg/mL stock solution so as to have a final volume of 2.4 L.

In this process, the lipids dissolved in ethanol and the mRNA dissolved in citrate buffer were mixed using a pump system. The instantaneous mixing of the two streams results in formation of lipid nanoparticles. The resultant formulation mixture is in citrate buffer containing 20% ethanol. The formulation is subjected to a buffer exchange using TFF system and the resultant formulation was adjusted to the desired mRNA concentration and stored frozen until further use. Final concentration of the formulation was determined at 0.5 mg/mL CFTR mRNA (encapsulated). The formulation had about 95% mRNA encapsulation and the lipid nanoparticles had an average size of around 59 nm with PDI of 0.15.

I. Formulation Example—200 mg Scale, N/P=4

Aliquots of 10 mg/mL ethanolic solutions of ICE, DOPE and DMG-PEG2K (molar ratio of 60:35:5) were mixed and diluted with ethanol to 600 mL final volume. Separately, an aqueous buffered solution (10 mM citrate/150 mM NaCl, pH 4.5) of hCFTR-STOP mRNA was prepared from a 1 mg/mL stock solution so as to have a final volume of 2.4 L.

In this process, the lipids dissolved in ethanol and the mRNA dissolved in citrate buffer were mixed using a pump system. The instantaneous mixing of the two streams resulted in formation of lipid nanoparticles. The resultant formulation mixture was in citrate buffer containing 20% ethanol. The formulation was subjected to a buffer exchange using TFF system and the resultant formulation is adjusted to the desired mRNA concentration and stored frozen until further use. Final concentration of the formulation was determined at 0.5 mg/mL CFTR STOP mRNA (encapsulated). The formulation had about 88% mRNA encapsulation and the lipid nanoparticles had an average size of around 57 nm with PDI of 0.18.

Pulmonary Delivery of ICE LNPs

Several exemplary studies were performed to demonstrate successful mRNA delivery and subsequent human CFTR protein production from ICE-based LNPs encapsulating codon-optimized hCFTR mRNA. Immunohistochemical analysis was performed on all lung sections using an anti-human CFTR antibody to specifically detect human CFTR protein within the lungs of treated animals.

Example 1. In Vivo Expression of hCFTR in Rat Lungs after Intratracheal Administration FIG. 1 shows exemplary immunohistochemical detection of hCFTR protein in mice lungs 24 hours after pulmonary delivery of hCFTR mRNA lipid nanoparticles prepared by the process described above (Formulation Example #1).

Mice were administered LNP formulations containing hCFTR mRNA via microsprayer (intratracheal aerosol). The LNP formulations were made using ICE lipid as the cationic lipid. The fixed lung tissues from these mice were analyzed for the presence of hCFTR protein by immunohistochemical staining.

Protein was detected throughout the entire lung including both the bronchial epithelial cells and the alveolar regions. Positive (brown) staining was observed in all mRNA lipid nanoparticle test article groups, as compared to the lack of brown staining in the lungs of untreated control mice. Panel A depicts untreated mouse lung at 10× magnification. Panel B depicts untreated mouse lung at 20× magnification. Panel C depicts codon-optimized hCFTR (CO-hCFTR) mRNA ICE LNP-treated mouse lung at 10× magnification. Panel D depicts CO-hCFTR mRNA ICE LNP-treated mouse lung at 20× magnification.

Figure 2:
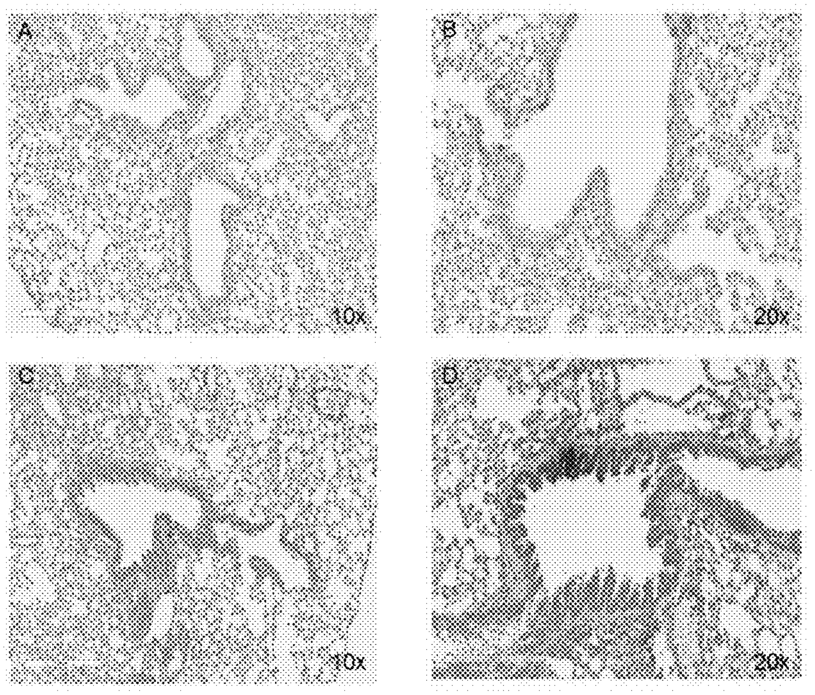
FIG. 2 depicts exemplary immunohistochemical detection of human CFTR protein in mouse lung 24 hours after treatment with ICE-based LNPs encapsulating codon-optimized hCFTR. A, B=Untreated mouse lung at 10× & 20× magnification, respectively. C, D=CO-hCFTR mRNA ICE LNP-treated mouse lung at 10× & 20× magnification, respectively.

Example 2. In Vivo Expression of hCFTR in Rat Lungs after Nebulization Administration FIG. 2 shows exemplary immunohistochemical detection of hCFTR protein in mice lungs 24 hours after pulmonary delivery of hCFTR mRNA lipid nanoparticles prepared by the process described above (Formulation Example #1).

Mice were administered, via nebulization, LNP formulations containing hCFTR mRNA. The LNP formulations were made using ICE lipid as the cationic lipid. The fixed lung tissues from these mice were analyzed for the presence of hCFTR protein by immunohistochemical staining.

Protein was detected throughout the entire lung including both the bronchial epithelial cells and the alveolar regions. Positive (brown) staining was observed in all mRNA lipid nanoparticle test article groups, as compared to the lack of brown staining in the lungs of untreated control mice. Panel A depicts untreated mouse lung at 10× magnification. Panel B depicts untreated mouse lung at 20× magnification. Panel C depicts codon-optimized hCFTR (CO-hCFTR) mRNA ICE LNP-treated mouse lung at 10× magnification. Panel D depicts CO-hCFTR mRNA ICE LNP-treated mouse lung at 20× magnification.

Example 3. In Vivo Expression of hCFTR in Rat Lungs (10 mg, 5% PEG)

Figure 3:
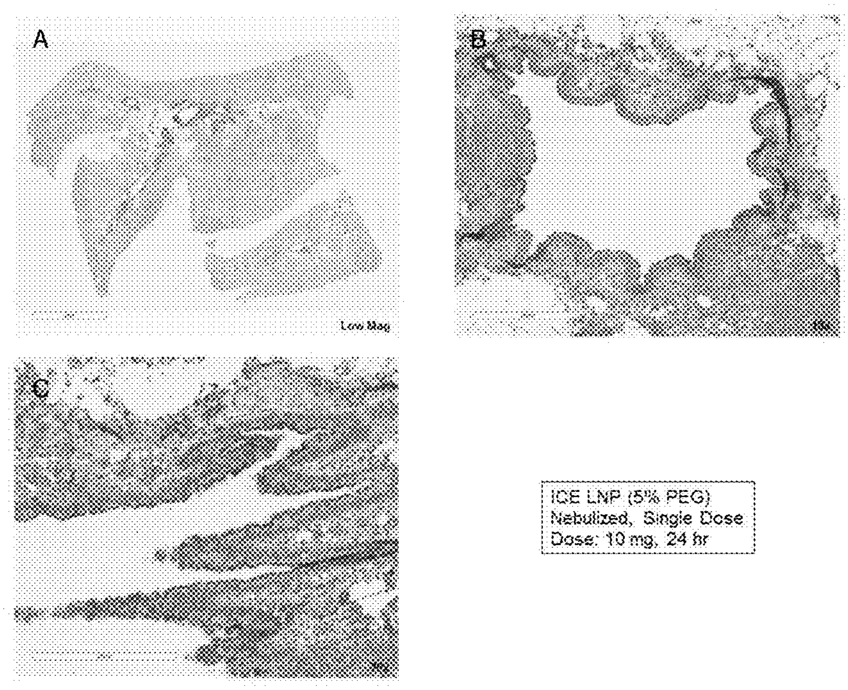
FIG. 3 depicts exemplary immunohistochemical detection of human Cystic Fibrosis Transmembrane Conductance Regulator (hCFTR) protein in the lungs of rats 24 hours after treatment with nebulized ICE-based lipid nanoparticles (LNPs) (5% PEG) encapsulating codon-optimized hCFTR mRNA.

FIG. 3 shows exemplary immunohistochemical analysis of hCFTR protein in rat lungs 24 hours after pulmonary delivery of codon-optimized hCFTR (CO-hCFTR) mRNA lipid nanoparticles prepared by the process described above using ICE-based lipid nanoparticles.

In some representative studies, rats were placed in an aerosol chamber which allowed for full motion of the rats. An aerosol was produced via nebulization of 10 mg (as measured by encapsulated mRNA)CO-hCFTR mRNA encapsulated in ICE LNPs (containing 5% [mol] of PEG-modified lipid) which filled the chamber containing the rats. The rats were exposed for a given period of time with during which the aerosol was freely taken into the lungs via normal breathing. After the exposure, the rats were removed and placed back into their cages. The rats were then sacrificed 24 hours after exposure and the lungs were harvested (a portion was snap frozen and a separate portion was fixed in 10% NBF and embedded in paraffin) for analysis. The fixed lung tissues from these rats were analyzed for the presence of hCFTR protein by immunohistochemical staining.

Protein was detected throughout the entire lung, including the bronchial epithelial cells and the alveolar regions, as shown in FIG. 3. Positive (brown) staining was observed in the mRNA lipid nanoparticle test article group. Panel A depicts the CO-hCFTR mRNA ICE LNP-treated rat lung at a low magnification. Panel B depicts CO-hCFTR mRNA ICE LNP-treated rat lung at 10× magnification. Panel C depicts CO-hCFTR mRNA ICE LNP-treated rat lung at 20× magnification.

Example 4. In Vivo Expression of hCFTR in Rat Lungs (50 μg mRNA, 5% PEG)

Figure 4:
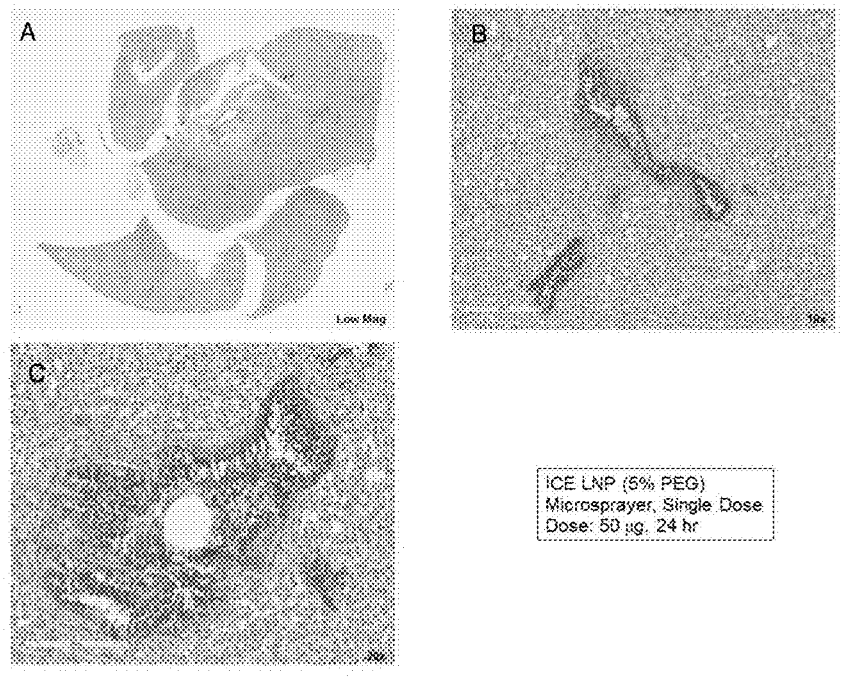
FIG. 4 depicts exemplary immunohistochemical detection of hCFTR protein in the lungs of rats 24 hours after treatment with ICE-based LNPs (5% PEG) encapsulating codon-optimized hCFTR mRNA via intratracheal administration.

FIG. 4 shows exemplary immunohistochemical analysis of hCFTR protein in rat lungs 24 hours after pulmonary delivery of CO-hCFTR mRNA lipid nanoparticles prepared by the process described above using ICE-based lipid nanoparticles.

In some representative studies, rats were exposed to CO-hCFTR mRNA ICE LNPs using direct instillation via a MicroSprayer apparatus. An aerosol was produced via a MicroSprayer apparatus during intratracheal administration of 50 μg CO-hCFTR mRNA encapsulated ICE LNPs (containing 5% [mol] of PEG-modified lipid) in rats. The rats were then sacrificed 24 hours after exposure and the lungs were harvested (a portion was snap frozen and a separate portion was fixed in 10% NBF and embedded in paraffin) for analysis. The fixed lung tissues from these rats were analyzed for the presence of hCFTR protein by immunohistochemical staining.

Protein was detected throughout the entire lung, including the bronchial epithelial cells and the alveolar regions, as shown in FIG. 4. Positive (brown) staining was observed in the mRNA lipid nanoparticle test article group. Panel A depicts the CO-hCFTR mRNA ICE LNP-treated rat lung at a low magnification. Panel B depicts CO-hCFTR mRNA ICE LNP-treated rat lung at 10× magnification. Panel C depicts CO-hCFTR mRNA ICE LNP-treated rat lung at 20× magnification.

Example 5. In Vivo Expression of hCFTR in Rat Lungs (10 mg, 3% PEG)

Figure 5:
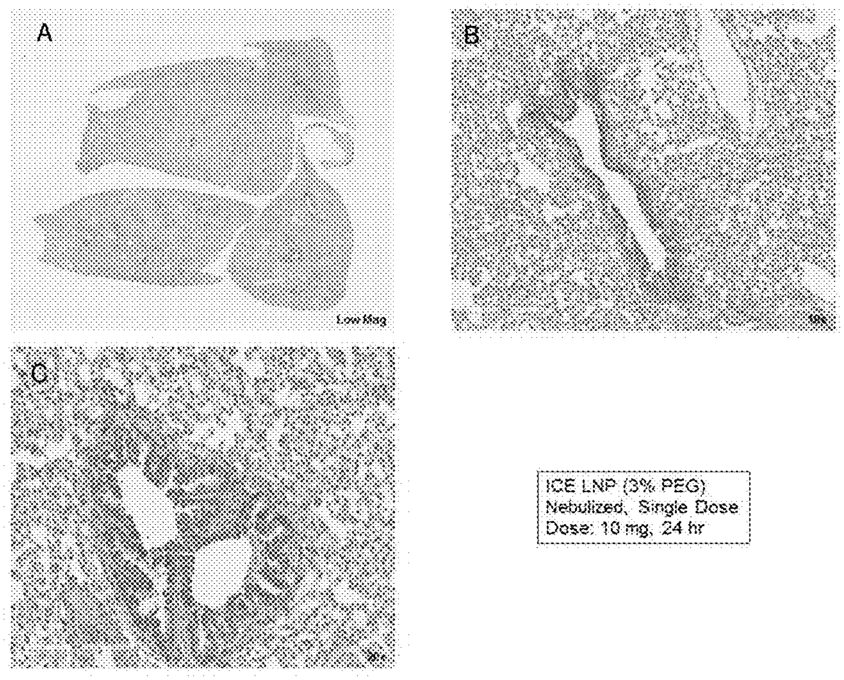
FIG. 5 depicts exemplary immunohistochemical detection of human CFTR protein in the lungs of rats 24 hours after treatment with nebulized ICE-based LNPs (3% PEG) encapsulating codon-optimized (CO) hCFTR mRNA.

FIG. 5 shows exemplary immunohistochemical analysis of hCFTR protein in rat lungs 24 hours after pulmonary delivery of CO-hCFTR mRNA lipid nanoparticles prepared by the process described above using ICE-based lipid nanoparticles.

In some representative studies, rats were placed in an aerosol chamber which allowed for full motion of the rats. An aerosol was produced via nebulization of 10 mg CO-hCFTR mRNA encapsulated in ICE LNPs (containing 3% [mol] of PEG-modified lipid) which filled the chamber containing the rats. The rats were exposed for a given period of time during which the aerosol was freely taken into the lungs via normal breathing. After the exposure, the rats were removed and placed back into their cages. The rats were then sacrificed 24 hours after exposure and the lungs were harvested (a portion was snap frozen and a separate portion was fixed in 10% NBF and embedded in paraffin) for analysis. The fixed lung tissues from these rats were analyzed for the presence of hCFTR protein by immunohistochemical staining.

Protein was detected throughout the entire lung, including the bronchial epithelial cells and the alveolar regions, as shown in FIG. 5. Positive (brown) staining was observed in the mRNA lipid nanoparticle test article group. Panel A depicts the CO-hCFTR mRNA ICE LNP-treated rat lung at a low magnification. Panel B depicts CO-hCFTR mRNA ICE LNP-treated rat lung at 10× magnification. Panel C depicts CO-hCFTR mRNA ICE LNP-treated rat lung at 20× magnification.

Example 6. In Vivo Expression of hCFTR in Rat Lungs (50 μg mRNA, 3% PEG)

Figure 6:
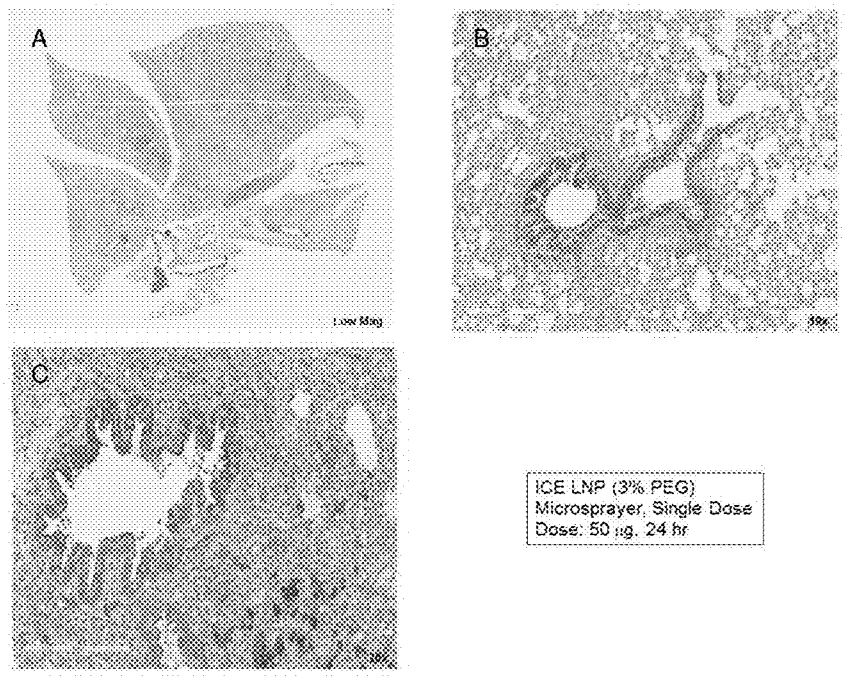
FIG. 6 depicts exemplary immunohistochemical detection of human CFTR protein in the lungs of rats 24 hours after treatment with ICE-based LNPs (3% PEG) encapsulating CO-hCFTR mRNA via intratracheal (Microsprayer) administration.

FIG. 6 shows exemplary immunohistochemical analysis of hCFTR protein in rat lungs 24 hours after pulmonary delivery of CO-hCFTR mRNA lipid nanoparticles prepared by the process described above using ICE-based lipid nanoparticles.

In some representative studies, rats were exposed to CO-hCFTR mRNA ICE LNPs using direct instillation via a MicroSprayer apparatus. An aerosol was produced via a MicroSprayer apparatus during intratracheal administration of 50 μg CO-hCFTR mRNA encapsulated ICE LNPs (containing 3% [mol] of PEG-modified lipid) in rats. The rats were then sacrificed 24 hours after exposure and the lungs were harvested (a portion was snap frozen and a separate portion was fixed in 10% NBF and embedded in paraffin) for analysis. The fixed lung tissues from these rats were analyzed for the presence of hCFTR protein by immunohistochemical staining.

Protein was detected throughout the entire lung, including the bronchial epithelial cells and the alveolar regions, as shown in FIG. 6. Positive (brown) staining was observed in the mRNA lipid nanoparticle test article group. Panel A depicts the CO-hCFTR mRNA ICE LNP-treated rat lung at a low magnification. Panel B depicts CO-hCFTR mRNA ICE LNP-treated rat lung at 10× magnification. Panel C depicts CO-hCFTR mRNA ICE LNP-treated rat lung at 20× magnification.

Example 7. In Vivo Expression of hCFTR in Mouse Lungs (10 mg, N/P=2)

Figure 7:
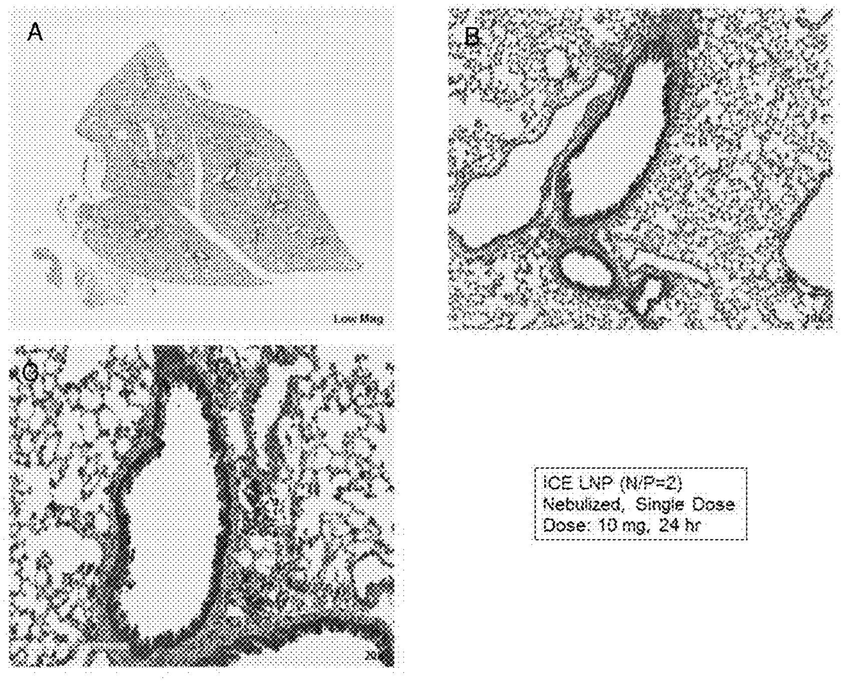
FIG. 7 depicts exemplary immunohistochemical detection of human CFTR protein in the lungs of CFTR KO (knockout) mice 24 hours after treatment with nebulized ICE-based LNPs (N/P=2) encapsulating CO-hCFTR mRNA.

FIG. 7 shows exemplary immunohistochemical analysis of hCFTR protein in CFTR KO mouse lungs 24 hours after pulmonary delivery of CO-hCFTR mRNA lipid nanoparticles prepared by the process described above using ICE based lipid nanoparticles.

In some representative studies, mice were placed in an aerosol chamber which allowed for full motion of the mice. An aerosol was produced via nebulization of 10 mg CO-hCFTR mRNA encapsulated in ICE LNPs (N/P=2) which filled the chamber containing the mice. The mice were exposed for a given period of time with which the aerosol was freely taken into the lungs via normal breathing. After the exposure, the mice were removed and placed back into their cages. The mice were then sacrificed 24 hours after exposure and the lungs were harvested (a portion was snap frozen and a separate portion was fixed in 10% NBF and embedded in paraffin) for analysis. The fixed lung tissues from these mice were analyzed for the presence of hCFTR protein by immunohistochemical staining.

Protein was detected throughout the entire lung, including the bronchial epithelial cells and the alveolar regions, as shown in FIG. 7. Positive (brown) staining was observed in the mRNA lipid nanoparticle test article group. Panel A depicts the CO-hCFTR mRNA ICE LNP-treated mouse lung at a low magnification. Panel B depicts CO-hCFTR mRNA ICE LNP-treated mouse lung at 10× magnification. Panel C depicts CO-hCFTR mRNA ICE LNP-treated mouse lung at 20× magnification.

Example 8. In Vivo Expression of hCFTR in Mouse Lungs (10 mg, N/P=4)

Figure 8:
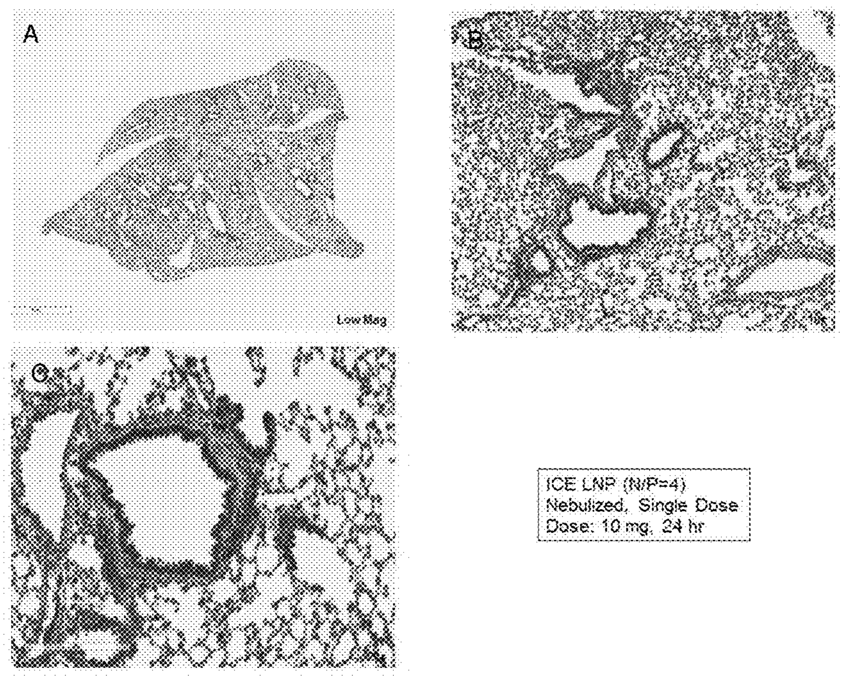
FIG. 8 depicts exemplary immunohistochemical detection of human CFTR protein in the lungs of CFTR KO mice 24 hours after treatment with nebulized ICE-based LNPs (N/P=4) encapsulating CO-hCFTR mRNA.

FIG. 8 shows exemplary immunohistochemical analysis of hCFTR protein in CFTR KO mouse lungs 24 hours after pulmonary delivery of CO-hCFTR mRNA lipid nanoparticles prepared by the process described above using ICE-based lipid nanoparticles.

In some representative studies, mice were placed in an aerosol chamber which allowed for full motion of the mice. An aerosol was produced via nebulization of 10 mg CO-hCFTR mRNA encapsulated in ICE LNPs (N/P=4) which filled the chamber containing the mice. The mice were exposed for a given period of time with which the aerosol was freely taken into the lungs via normal breathing. After the exposure, the mice were removed and placed back into their cages. The mice were then sacrificed 24 hours after exposure and the lungs were harvested (a portion was snap frozen and a separate portion was fixed in 10% NBF and embedded in paraffin) for analysis. The fixed lung tissues from these mice were analyzed for the presence of hCFTR protein by immunohistochemical staining.

Protein was detected throughout the entire lung, including the bronchial epithelial cells and the alveolar regions, as shown in FIG. 8. Positive (brown) staining was observed in the mRNA lipid nanoparticle test article group. Panel A depicts the CO-hCFTR mRNA ICE LNP-treated mouse lung at a low magnification. Panel B depicts CO-hCFTR mRNA ICE LNP-treated mouse lung at 10× magnification. Panel C depicts CO-hCFTR mRNA ICE LNP-treated mouse lung at 20× magnification. Widespread distribution of hCFTR protein is observed in both example 5 (N/P=2) and example 6 (N/P=4).

Example 9. In Vivo Expression of hCFTR in Mouse Lungs with Different Formulations FIG. 9 shows exemplary immunohistochemical analysis of hCFTR protein in wild-type mouse lungs 24 hours after pulmonary delivery of CO-hCFTR mRNA lipid nanoparticles prepared by the process described above using ICE-based lipid nanoparticles.

In some representative studies, several groups of wild-type mice were separated and placed in individual aerosol chambers. Each group was treated with a different formulation. The formulations consisted of ICE-based LNPs (N/P=4) encapsulating the following mRNA constructs: 1)CO-hCFTR mRNA ICE LNP; 2)CO-hCFTR "STOP" mRNA (nonsense mutated CO-hCFTR mRNA unable to translate protein) ICE LNP; 3) FFL (Firefly Luciferase) mRNA ICE LNP; and 4) Buffer (Vehicle).

In some embodiments, mice were placed in an aerosol chamber which allowed for full motion of the mice. An aerosol was produced via nebulizer of CO-hCFTR mRNA encapsulated in ICE LNPs (N/P=4) which filled the chamber containing the mice. The mice were exposed for a total of 50 mg (shown in FIG. 7) aerosolized CO-hCFTR mRNA (as measured by encapsulated mRNA) for a given period of time with which the aerosol was freely taken into the lungs via normal breathing. After the exposure, the mice were removed and placed back into their cages. The mice were then sacrificed 24 hours after exposure and the lungs were harvested (a portion was snap frozen and a separate portion was fixed in 10% NBF and embedded in paraffin) for analysis. The fixed lung tissues from these mice were analyzed for the presence of hCFTR protein by immunohistochemical staining.

Figure 9:
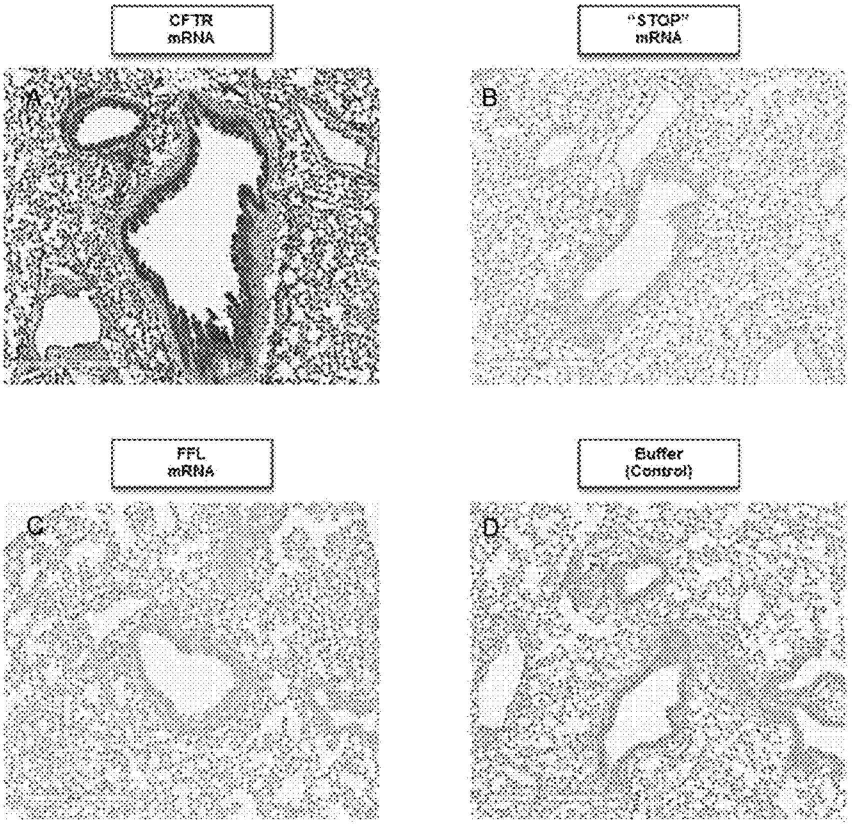
FIG. 9 depicts exemplary immunohistochemical detection of human CFTR protein in the lungs of wild-type mice 24 hours after treatment with nebulized ICE-based LNPs encapsulating various mRNA constructs including CFTR (CO-hCFTR mRNA), STOP (nonsense mutated CO-hCFTR mRNA unable to be translated into protein), and FFL (Firefly Luciferase mRNA).

In FIG. 9, positive (brown) staining was observed only in the CO-hCFTR mRNA LNP test article group. The first panel depicts the CO-hCFTR mRNA ICE LNP-treated mouse lung showing widespread distribution of human CFTR protein observed throughout the entire lung, including both bronchial epithelial and alveolar regions. The second panel depicts CO-hCFTR "STOP" mRNA ICE LNP-treated mouse lung with no positive (brown) staining observed. The third panel depicts FFL mRNA ICE LNP-treated mouse lung with no positive (brown) staining observed. The fourth panel depicts buffer treated mouse lung with no positive (brown) staining observed.

Example 10. In Vivo Expression of hCFTR in Mouse Lungs at Different Time Points FIG. 10 shows exemplary immunohistochemical analysis of hCFTR protein in wild-type mouse lungs at predetermined time points after pulmonary delivery of CO-hCFTR mRNA lipid nanoparticles prepared by the process described above using ICE-based lipid nanoparticles.

In some representative studies, the pharmacokinetic behavior of hCFTR protein after treatment of CO-hCFTR mRNA encapsulated ICE LNPs was performed in CFTR KO mice. In some embodiments, mice were placed in an aerosol chamber which allowed for full motion of the mice. An aerosol was produced via nebulization of CO-hCFTR mRNA encapsulated in ICE LNPs (N/P=4) which filled the chamber containing the mice. The mice were exposed to 10 mg aerosolized CO-hCFTR mRNA for a given period of time during which the aerosol was freely taken into the lungs via normal breathing. After the exposure, the mice were removed and placed back into their cages. Selected cohorts of treated mice were sacrificed at pre-determined time points after aerosol exposure. The time range for sacrificing the mice post-administration ranged from 30 minutes to one week, specifically, 30 minutes, 2 hours, 4 hours, 6 hours, 24 hours, 48 hours, 72 hours and 1 week as shown in FIG. 10. The mouse lungs were harvested (a portion was snap frozen and a separate portion was fixed in 10% NBF and embedded in paraffin) for analysis. The fixed lung tissues from these mice were analyzed for the presence of hCFTR protein by immunohistochemical staining.

Figure 10:
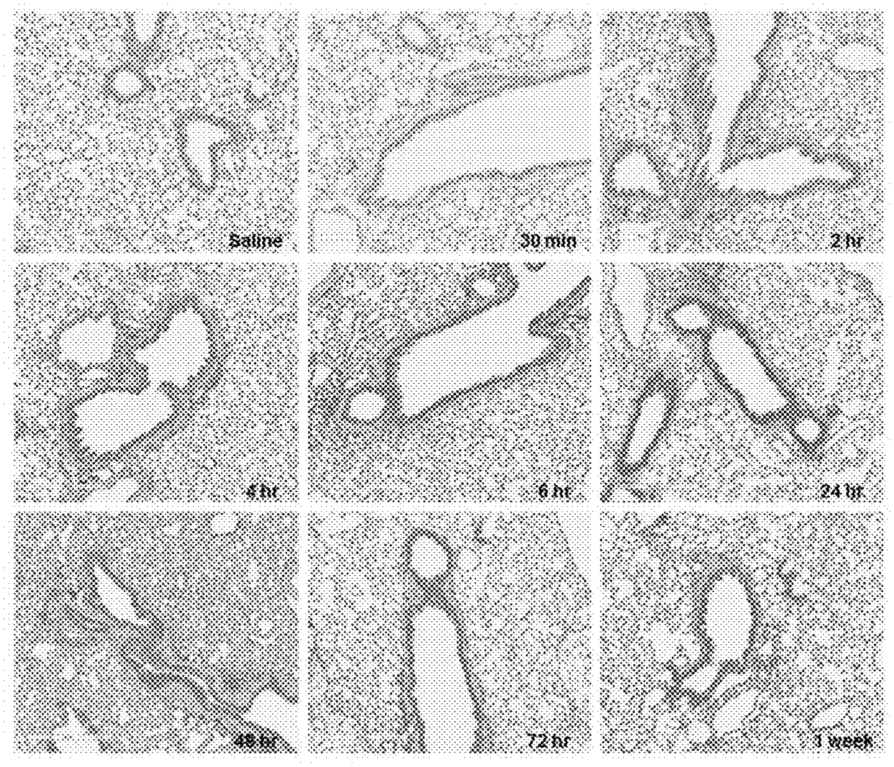
FIG. 10 depicts exemplary immunohistochemical detection of human CFTR protein in the lungs of wild-type mice at various time points after a single exposure to nebulized ICE-based LNPs encapsulating CO-hCFTR mRNA.

As shown in FIG. 10, protein or positive (brown) staining was detected throughout the entire lung, including both the bronchial epithelial cells and the alveolar regions, in the hCFTR mRNA treated mouse groups sacrificed more than 30 minutes after administration. The most positive or brown staining was observed at 24 hours, 48 hours and 72 hours after hCFTR mRNA delivery. No positive (brown) staining was observed in the saline treated control group.

Example 11. In Vivo Expression of hCFTR in Rat Lungs at Different Dose Levels In some representative studies, rats were placed in an aerosol chamber which allowed for full motion of the rats. An aerosol was produced via nebulization of CO-hCFTR mRNA encapsulated in ICE LNPs which filled the chamber containing the rats. The rats were exposed for a given period of time with which the aerosol was freely taken into the lungs via normal breathing. Several groups were dosed at different dose levels as following: 1) Buffer; 2) Empty ICE LNP (~8.0 mg/kg equivalent); 3) ICE LNP (0.5 mg/kg); 4) ICE LNP (2.1 mg/kg); 5) ICE LNP (4.1 mg/kg); and 6) ICE LNP (6.2 mg/kg).

After administration, the rats were removed and placed back into their cages. Furthermore, each group of rats was split into selected cohorts that were sacrificed at different predetermined time points post-administration. The time range for sacrificing the rats post-administration was 24 hours to 28 days, specifically 24 hours, 7 days, 14 days and 28 days.

Figure 11:
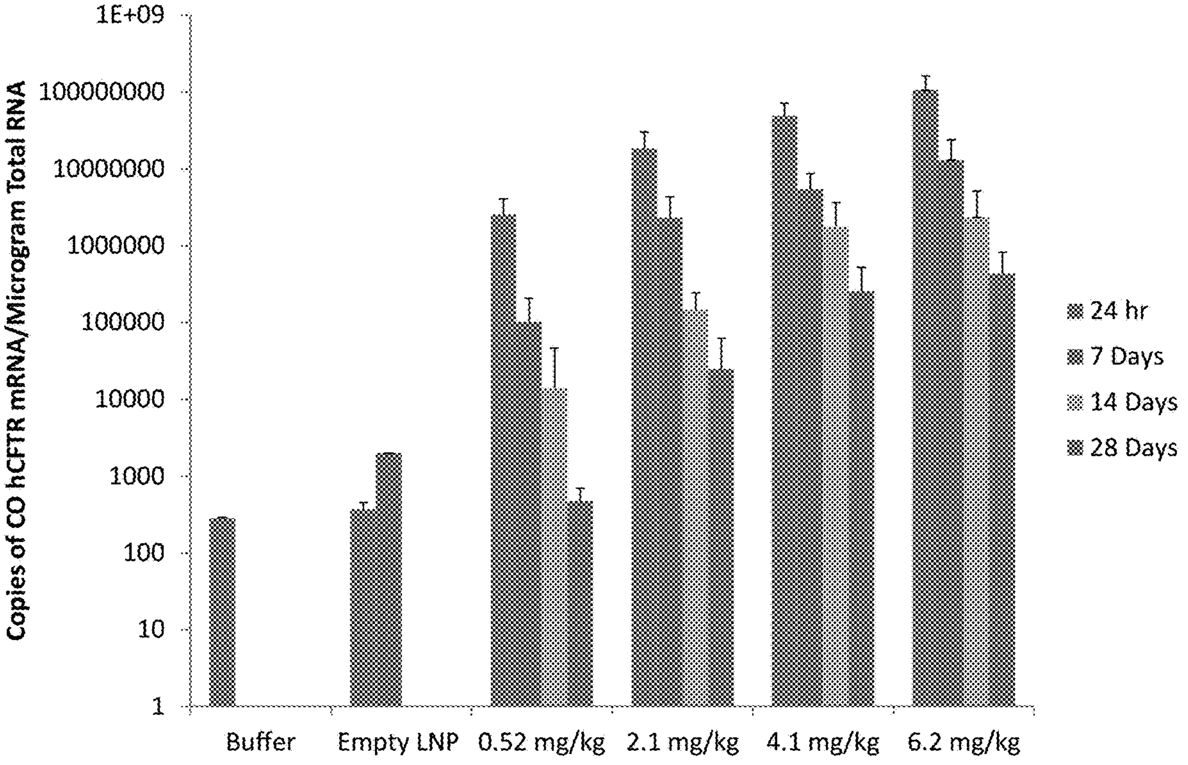
FIG. 11 depicts an exemplary graph of the ratio of copies of CO-hCFTR mRNA per micrograms of total RNA in frozen lung sections from rats treated with either controls (buffer, Empty ICE LNP) or CO-hCFTR mRNA loaded ICE LNPs.

Quantitative PCR, which measures copies of CO-hCFTR mRNA per total RNA, was performed on snap frozen lungs of all treated rats in each group. The results are represented in FIG. 11, showing the ratio of copies of CO-hCFTR mRNA per micrograms of total RNA. Results were analyzed across the different doses administered and at the selected sacrifice time points for each dose level. Background levels of CO-hCFTR mRNA are indicated by the control groups' (Buffer and Empty LNP) values. Copies of CO-hCFTR mRNA per total RNA in frozen lung sections of rats increased as the dose level increased. At the same dose level, copies of CO-hCFTR mRNA per total RNA in frozen lung sections of rats decreased as the sacrifice time post-administration increased.

Figure 12:
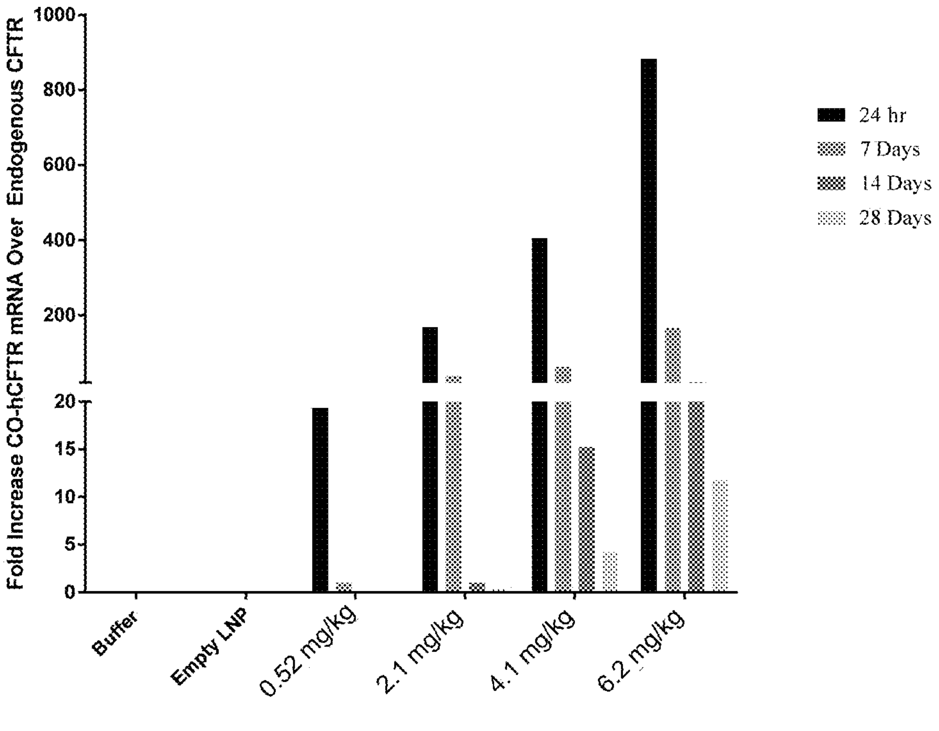
FIG. 12 depicts an exemplary graph of fold-increase of copies of CO-hCFTR over endogenous levels of CFTR mRNA in frozen lung sections of rats treated with either controls (buffer, Empty ICE LNP) or CO-hCFTR mRNA loaded ICE LNPs.

FIG. 12 shows a comparison of the levels of copies of exogenous CO-hCFTR mRNA per copy of endogenous CFTR mRNA. The fold-increase or ratio of copies of CO-hCFTR mRNA per copy of endogenous CFTR mRNA in frozen lung sections of rats was assessed and plotted as a function of dose and sacrifice time. The data was also obtained using Quantitative PCR. Fold-increase of copies of CO-hCFTR mRNA over endogenous levels of CFTR mRNA increased as the dose level increased. At the same mRNA dosage, fold-increase of copies of CO-hCFTR mRNA over endogenous levels of CFTR mRNA decreased as the sacrifice time post-administration increased.

Figure 13:
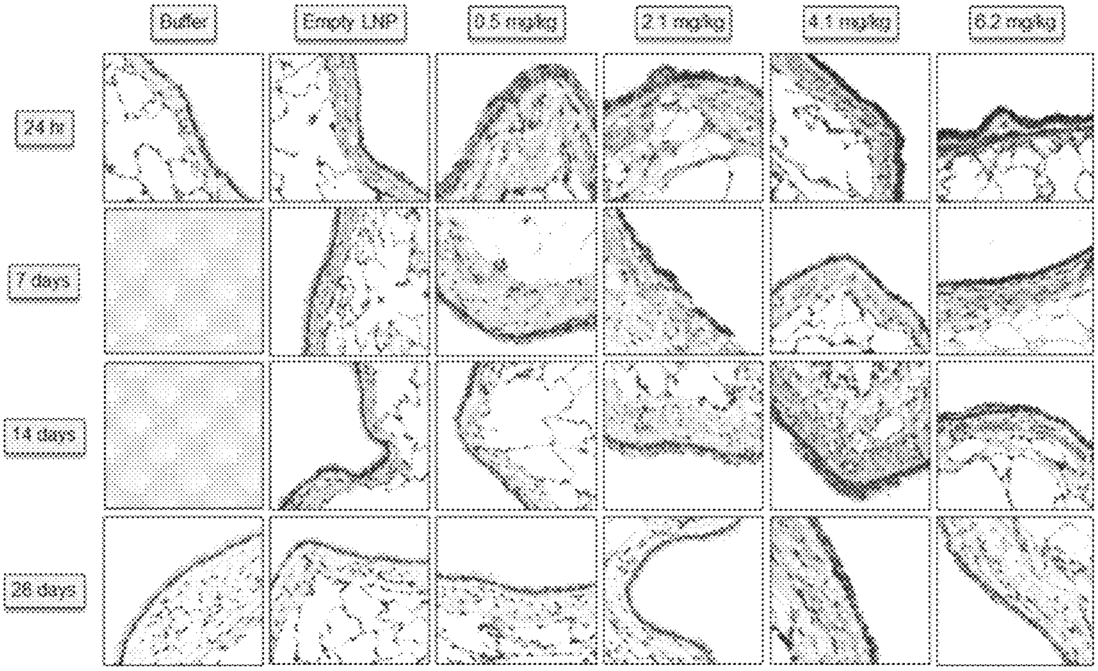
FIG. 13 depicts exemplary immunohistochemical detection of human CFTR protein in the lungs of rats after a single exposure to various doses of nebulized ICE-based LNPs encapsulating CO-hCFTR mRNA.

Immunohistochemical analysis of the rat lungs was also performed and is shown in FIG. 13. The fixed lung tissues from these rats were analyzed for the presence of hCFTR protein by immunohistochemical staining. A dose-dependent increase in hCFTR protein was observed as determined by positive (brown) staining throughout the entire lung, including both bronchial epithelial and alveolar regions. A decrease in hCFTR protein was observed as determined by positive (brown) staining as the time after the single dose of administration increased beyond 24 hours. However, detectable levels of hCFTR protein were observed 28 days after a single exposure of hCFTR mRNA ICE LNPs. No positive (brown) staining was observed in the saline treated control group or in the empty LNP group.

Example 12. In Vivo Effect of hCFTR Formulations on Respiration

Figure 14A:
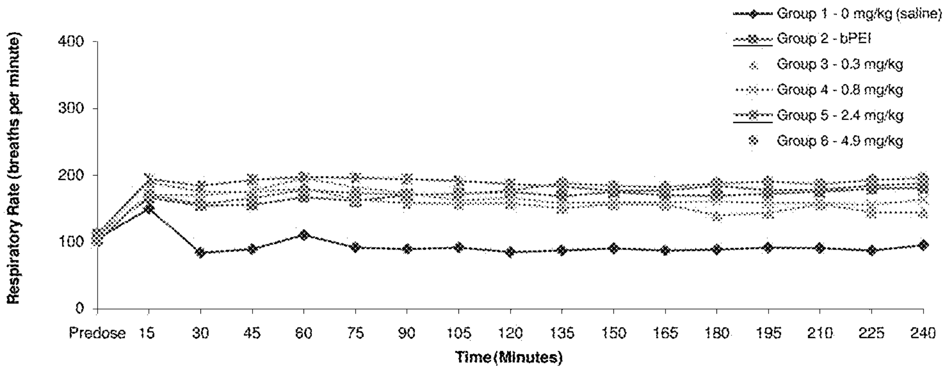
FIGS. 14A and 14B depict exemplary graphs of the effects of various dosages of hCFTR mRNA formulated with either branched PEI (FIG. 14A) or ICE (FIG. 14B) on the respiratory rate of rats relative to a control.
Figure 14B:
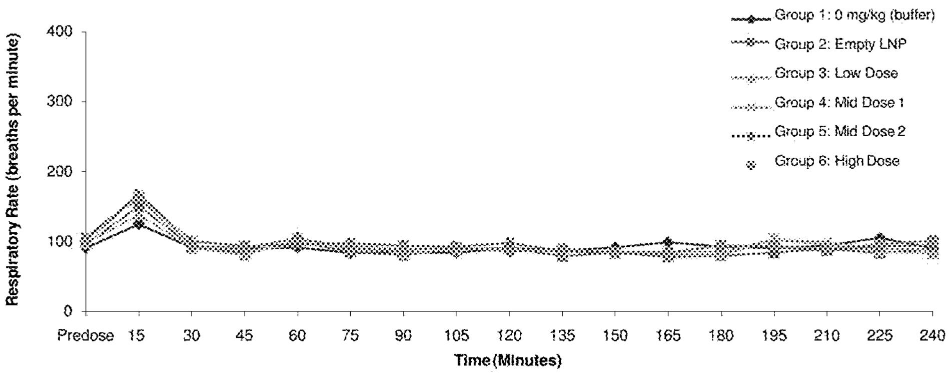

In some representative studies, rats were exposed to a single dose of hCFTR mRNA via inhalation. The hCFTR mRNA was formulated with either ICE as described above or with branched PEI (bPEI). As shown in FIG. 14A, the various dosages of hCFTR mRNA formulated with bPEI caused an adverse respiratory rate increase relative to a saline control in the rats studied. When the rats were sacrificed, it was also found that the weight of the lungs was also increased. By comparison, as shown in FIG. 14B, the various dosages of hCFTR mRNA formulated with ICE did not cause an increase in respiratory rate relative to a buffer control in the rats studied. There was also no increase in the weight of the rat lungs observed when the rats were sacrificed.

Example 13. In Vitro Expression and Activity of hCFTR at Different Dose Levels

Figure 15:
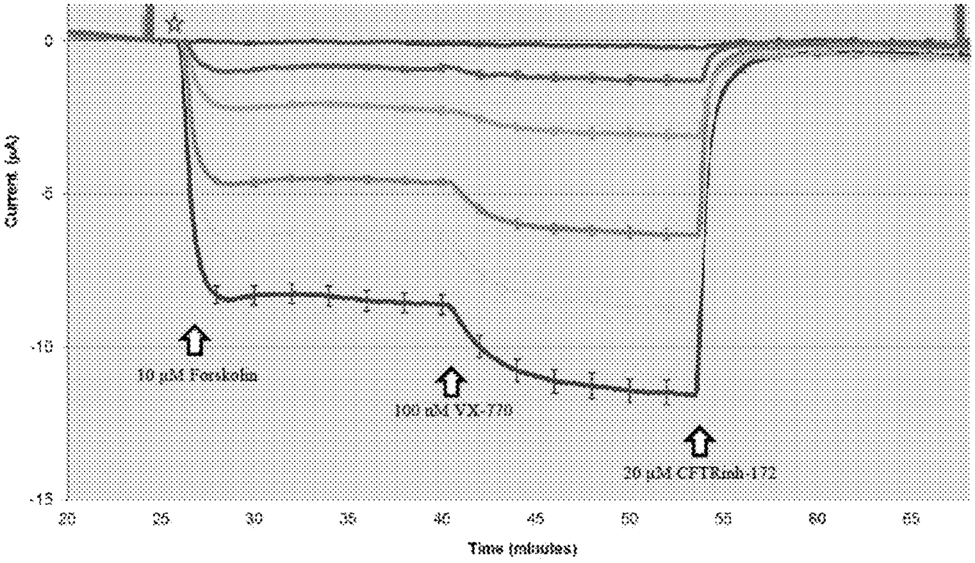
FIG. 15 depicts an exemplary graph showing a dose response of chloride-ion channel activity induced by hCFTR mRNA.

In some representative experiments, hCFTR mRNA was transfected into cultured Fischer rat thyroid cells using Lipofectamine according to standard procedures. As is shown in FIG. 15, there was a dose response of chloride-ion channel activity induced by hCFTR mRNA. This indicates that the hCFTR mRNA produced active CFTR protein in the transfected cells.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising nucleic acids and lipid nanoparticles encapsulating the nucleic acids, wherein the lipid nanoparticles comprise no more than three distinct lipids, wherein the lipids comprise a cationic lipid, a non-cationic lipid, and a PEG lipid at a molar ratio of 60:35:5, respectively, wherein one distinct component being a sterol-based cationic lipid comprising imidazole cholesterol ester (ICE), and wherein the lipid nanoparticles have an encapsulation percentage for mRNA of at least 85% and have an average size of less than about 80 nm.

2. The composition of claim 1, wherein the nucleic acids are mRNA encoding a protein or a peptide.

3. The composition of claim 2, wherein the mRNA encoding a protein or a peptide is codon-optimized.

4. The composition of claim 2, wherein the mRNA comprises one or more modified nucleotides.

5. The composition of claim 4, wherein the mRNA comprises a 5' cap structure.

6. The composition of claim 4, wherein the mRNA comprises a 5' untranslated region.

7. The composition of claim 6, wherein the mRNA comprise a 3' untranslated region.

8. The composition of claim 7, wherein the mRNA comprises a 3' tail structure comprising a poly(A) tail.

9. The composition of claim 1, wherein the lipid nanoparticles comprise helper lipids.

10. The composition of claim 1, wherein the lipid nanoparticles have a size less than about 75 nm and a PDI of less than about 0.2.

11. The composition of claim 2, wherein the mRNA encodes a Cystic Fribrosis Transmembrane Conductance Regulator (CFTR) protein.

12. The composition of claim 1, wherein the nucleic acids are present in the lipid nanoparticles at a concentration of about 0.5 mg/ml.

13. The composition of claim 1, wherein the lipid nanoparticles comprising the nucleic acids have a N/P ratio of about 2.

14. The composition of claim 1, wherein the lipid nanoparticles comprising the nucleic acids have a N/P ratio of about 4.

15. The composition of claim 1, wherein the nucleic acids are selected from DNA, siRNA, microRNA, and mRNA.

16. The composition of claim 9, wherein the helper lipid is distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, or 1-stearoyl-2-oleoyl-phosphatidyethanolamine (SOPE).

* * * * *

SEQUENCE LISTING

```
<160> NUMBER OF SEQ ID NOS: 11

<210> SEQ ID NO 1
<211> LENGTH: 4443
<212> TYPE: RNA
<213> ORGANISM: Artificial Sequence
<220> FEATURE:
<223> OTHER INFORMATION: chemically synthesized oligonucleotide

<400> SEQUENCE: 1

augcaacgcu cuccucuuga aaaggccucg guggugucca agcucuucuu cucguggacu     60

agacccaucc ugagaaaggg guacagacag cgcuuggagc uguccgauau cuaucaaauc    120

ccuuccgugg acuccgcgga caaccugucc gagaagcucg agagagaaug ggacagagaa    180

cucgccucaa agaagaaccc gaagcugauu aaugcgcuua ggcggugcuu uuucuggcgg    240

uucauguucu acggcaucuu ccucuaccug ggagagguca ccaaggccgu gcagccccug    300

uugcugggac ggauuauugc cuccuacgac cccgacaaca aggaagaaag aagcaucgcu    360

aucuacuugg gcaucggucu gugccugcuu uucaucgucc ggacccucuu guugcauccu    420

gcuauuuucg gccugcauca cauuggcaug cagaugagaa uugccauguu uucccugauc    480

uacaagaaaa cucugaagcu cucgagccgc gugcuugaca agauuuccau cggccagcuc    540

gugucccugc ucuccaacaa ucugaacaag uucgacgagg gccucgcccu ggcccacuuc    600

guguggaucg ccccucugca aguggcgcuu cugaugggcc ugaucuggga gcugcugcaa    660

gccucggcau ucugugggcu uggauuccug aucgugcugg cacuguucca ggccggacug    720

gggcggauga ugaugaagua cagggaccag agagccggaa agauuuccga acggcuggug    780

aucacuucgg aaaugaucga aaacauccag ucagugaagg ccuacugcug ggaagaggcc    840

auggaaaaga ugauugaaaa ccuccggcaa accgagcuga agcugacccg caaggccgcu    900

uacgugcgcu auuucaacuc guccgcuuuc uucuucuccg gguucuucgu gguguuucuc    960

uccgugcucc ccuacgcccu gauuaaggga aucauccuca ggaagaucuu caccaccauu   1020

uccuucugua ucgugcuccg cauggccgug acccggcagu ucccaugggc cgugcagacu   1080

ugguacgacu cccugggagc cauuaacaag auccaggacu uccuucaaaa gcaggaguac   1140

aagacccucg aguacaaccu gacuacuacc gaggucguga uggaaaacgu caccgccuuu   1200

ugggaggagg gauuuggcga acuguucgag aaggccaagc agaacaacaa caaccgcaag   1260

accucgaacg gugacgacuc ccucuucuuu ucaaacuuca gccugcucgg gacgcccgug   1320

cugaaggaca uuaacuucaa gaucgaaaga ggacagcucc uggcgguggc cggaucgacc   1380

ggagccggaa agacuucccu gcugauggug aucaugggag agcuugaacc uagcgaggga   1440

aagaucaagc acuccggccg caucagcuuc uguagccagu uuuccuggau caugcccgga   1500

accauuaagg aaaacaucau cuucggcgug uccuacgaug aauaccgcua ccgguccgug   1560

aucaaagccu gccagcugga agaggauauu ucaaaguucg cggagaaaga uaacaucgug   1620
```

-continued cugggcgaag gggguauuac cuugucgggg ggccagcggg cuagaaucuc gcuggccaga 1680
gccguguaua aggacgccga ccuguaucuc cuggacuccc ccuucggaua ccuggacguc 1740
cugaccgaaa aggagaucuu cgaaucgugc gugugcaagc ugauggcuaa caagacucgc 1800
auccucguga ccuccaaaau ggagcaccug aagaaggcag acaagauucu gauucugcau 1860
gaggggnccu ccuacuuuua cggcaccuuc ucggaguugc agaacuugca gcccgacuuc 1920
ucaucgaagc ugaugggguug cgacagcuuc gaccaguucu ccgccgaaag aaggaacucg 1980
auccugacgg aaaccuugca ccgcuucucu uuggaaggcg acgccccugu gucauggacc 2040
gagacuaaga agcagagcuu caagcagacc ggggaauucg gcgaaaagag gaagaacagc 2100
aucuugaacc ccauuaacuc cauccgcaag uucucaaucg ugcaaaagac gccacugcag 2160
augaacggca uugaggagga cuccgacgaa ccccuugaga ggcgccuguc ccuggugccg 2220
gacagcgagc agggagaagc cauccugccu cggauuuccg ugaucuccac ugguccgacg 2280
cuccaagccc ggcggcggca guccgugcug aaccugauga cccacagcgu gaaccagggc 2340
caaaacauuc accgcaagac uaccgcaucc acccggaaag ugucccuggc accucaagcg 2400
aaucuuaccg agcucgacau cuacucccgg agacugucgc aggaaaccgg gcucgaaauu 2460
uccgaagaaa ucaacgagga ggaucugaaa gagugcuucu ucgacgauau ggagucgaua 2520
cccgccguga cgacuuggaa cacuuaucug cgguacauca cugugcacaa gucauugauc 2580
uucgugcuga uuuggugccu ggugauuuuc cuggccgagg ucgcggccuc acuggguggug 2640
cucuggcugu ugggaaacac gccucugcaa gacaagggaa acuccacgca cucgagaaac 2700
aacagcuaug ccgugauuau cacuuccacc uccucuuauu acguguucua caucuacguc 2760
ggaguggcgg auacccugcu cgcgaugggu uucuucagag gacugccgcu gguccacacc 2820
uugaucaccg ucagcaagau ucuucaccac aagauguugc auagcgugcu gcaggccccc 2880
auguccaccc ucaacacucu gaaggccgga ggcauucuga acagauucuc caaggacauc 2940
gcuauccugg acgaucuccu gccgcuuacc aucuuugacu ucauccagcu gcugcugauc 3000
gugauuggag caaucgcagu gguggcggug cugcagccuu acauuuucgu ggccacugug 3060
ccggucauug uggcguucau caugcugcgg gccuacuucc uccaaaccag ccagcagcug 3120
aagcaacugg aauccgaggg acgaucccc aucuucacuc accuugugac gucguugaag 3180
ggacugugga cccuccgggc uuucggacgg cagcccuacu ucgaaacccu cuuccacaag 3240
gcccugaacc uccacaccgc caauugguuc cuguaccugu ccacccugcg gugguuccag 3300
augcgcaucg agaugauuuu cgucaucuuc uucaucgcgg ucacauucau cagcauccug 3360
acuaccggag agggagaggg acgggucgga auaauccuga cccucgccau gaacauuaug 3420
agcacccugc agugggcagu gaacagcucg aucgacgugg acagccugau gcgaagcguc 3480
agccgcgugu ucaaguucau cgacaugccu acugagggaa aacccacuaa guccacuaag 3540
cccuacaaaa auggccagcu gagcaagguc augaucaucg aaaacuccca cgugaagaag 3600
gacgauauuu ggcccuccgg aggucaaaug accgugaagg accugaccgc aaaguacacc 3660
gagggaggaa acgccauucu cgaaaacauc agcuucucca uuucgccggg acagcggguc 3720
ggccuucucg ggcggaccgg uuccgggaag ucaacucugc ugucggcuuu ccuccggcug 3780
cugaauaccg agggggaaau ccaaauugac ggcgugucuu gggauuccau uacucugcag 3840
caguggcgga aggccuucgg cgugaucccc cagaaggugu ucaucuucuc ggguaccuuc 3900
cggaagaacc uggauccuua cgagcagugg agcgaccaag aaaucuggaa ggucgccgac 3960

-continued

```
gaggucggcc ugcgcuccgu gauugaacaa uuuccuggaa agcuggacuu cgugcucguc   4020

gacgggggau guguccuguc gcacggacau aagcagcuca ugugccucgc acgguccgug   4080

cucuccaagg ccaagauucu gcugcuggac gaaccuucgg cccaccugga uccggucacc   4140

uaccagauca ucaggaggac ccugaagcag gccuuugccg auugcaccgu gauucucugc   4200

gagcaccgca ucgaggccau gcuggagugc cagcaguucc uggucaucga ggagaacaag   4260

guccgccaau acgacuccau ucaaaagcuc cucaacgagc ggucgcuguu cagacaagcu   4320

auuucaccgu ccgauagagu gaagcucuuc ccgcaucgga acagcucaaa gugcaaaucg   4380

aagccgcaga ucgcagccuu gaaggaagag acugaggaag aggugcagga cacccggcuu   4440

uaa                                                                 4443


<210> SEQ ID NO 2
<211> LENGTH: 4443
<212> TYPE: RNA
<213> ORGANISM: Artificial Sequence
<220> FEATURE:
<223> OTHER INFORMATION: chemically synthesized oligonucleotide

<400> SEQUENCE: 2

augcagcggu ccccgcucga aaaggccagu gucgugucca aacucuucuu cucauggacu     60

cggccuaucc uuagaaaggg guaucggcag aggcuugagu ugucugacau cuaccagauc    120

cccucgguag auucggcgga uaaccucucg gagaagcucg aacgggaaug ggaccgcgaa    180

cucgcgucua agaaaaaccc gaagcucauc aacgcacuga gaaggugcuu cuucuggcgg    240

uucauguucu acgguaucuu cuuguaucuc ggggagguca caaaagcagu ccaaccccug    300

uuguuggguc gcauuaucgc cucguacgac cccgauaaca aagaagaacg gagcaucgcg    360

aucuaccucg ggaucggacu guguuugcuu uucaucguca gaacacuuuu guugcaucca    420

gcaaucuucg gccuccauca caucgguaug cagaugcgaa ucgcuauguu uagcuugauc    480

uacaaaaaga cacugaaacu cucgucgcgg guguuggaua agauuuccau cggucaguug    540

guguccccugc uuaguaauaa ccucaacaaa uucgaugagg gacuggcgcu ggcacauuuc    600

guguggauug ccccguugca agucgcccuu uugaugggcc uuauuuggga gcuguugcag    660

gcaucugccu uuuguggccu gggauuucug auuguguugg cauuguuuca ggcugggcuu    720

gggcggauga ugaugaagua ucgcgaccag agagcgggua aaaucucgga aagacucguc    780

aucacuucgg aaaugaucga aaacauccag ucggucaaag ccuauugcug ggaagaagcu    840

auggagaaga ugauugaaaa ccuccgccaa acugagcuga aacugacccg caaggcggcg    900

uauguccggu auuucaauuc gucagcguuc uucuuuuccg gguucuucgu ugucuuucuc    960

ucgguuuugc cuuaugccuu gauuaagggg auuauccucc gcaagauuuu caccacgauu   1020

ucguucugca uuguauugcg cauggcagug acacggcaau uuccgugggc cgugcagaca   1080

ugguaugacu cgcuuggagc gaucaacaaa auccaagacu ucuugcaaaa gcaagaguac   1140

aagacccugg aguacaaucu uacuacuacg gagguaguaa uggagaaugu gacggcuuuu   1200

ugggaagagg guuuuggaga acuguuugag aaagcaaagc agaauaacaa caaccgcaag   1260

accucaaaug gggacgauuc ccuguuuuuc ucgaacuucu cccugcucgg aacacccgug   1320

uugaaggaca ucaauuucaa gauugagagg ggacagcuuc ucgcgguagc gggaagcacu   1380

ggugcgggaa aaacuagccu cuugauggug auuauggggg agcuugagcc cagcgagggg   1440

aagauuaaac acuccgggcg uaucucauuc uguagccagu uuucauggau caugcccgga   1500

accauuaaag agaacaucau uuucggagua uccuaugaug aguaccgaua cagaucgguc   1560
```

-continued

```
auuaaggcgu gccaguugga agaggacauu ucuaaguucg ccgagaagga uaacaucguc   1620
uugggagaag gggguauuac auugucggga gggcagcgag cgcggaucag ccucgcgaga   1680
gcgguauaca aagaugcaga uuuguaucug cuugauucac cguuuggaua ccucgacgua   1740
uugacagaaa aagaaaucuu cgagucgugc guguguaaac uuauggcuaa uaagacgaga   1800
auccugguga caucaaaaau ggaacaccuu aagaaggcgg acaagauccu gauccuccac   1860
gaaggaucgu ccuacuuuua cggcacuuuc ucagaguugc aaaacuugca gccggacuuc   1920
ucaagcaaac ucaugggggug ugacucauuc gaccaguuca gcgcggaacg gcggaacucg   1980
aucuugacgg aaacgcugca ccgauucucg cuugagggug augccccggu aucguggacc   2040
gagacaaaga agcagucguu uaagcagaca ggagaauuug gugagaaaag aaagaacagu   2100
aucuugaauc cuauuaacuc aauucgcaag uucucaaucg uccagaaaac uccacugcag   2160
augaauggaa uugaagagga uucggacgaa ccccuggagc gcaggcuuag ccucgugccg   2220
gauucagagc aaggggaggc cauucuuccc cggauuucgg ugauuucaac cggaccuaca   2280
cuucaggcga ggcgaaggca auccgugcuc aaccucauga cgcauucggu aaaccagggg   2340
caaaacauuc accgcaaaac gacggccuca acgagaaaag ugucacuugc accccaggcg   2400
aauuugacug aacucgacau cuacagccgu aggcuuucgc aagaaaccgg acuugagauc   2460
agcgaagaaa ucaaugaaga agauuugaaa gaguguuucu uugaugacau ggaaucaauc   2520
ccagcgguga caacguggaa cacauacuug cguuacauca cggugcacaa guccuugauu   2580
uucguccuca ucuggugucu cgugaucuuu cucgcugagg ucgcagcguc acuuguggguc   2640
cucuggcugc uugguaauac gcccuugcaa gacaaaggca auucuacaca cucaagaaac   2700
aauuccuaug ccgugauuau cacuucuaca agcucguauu acguguuuua caucuacgua   2760
ggaguggccg acacucugcu cgcgaugggu uucuuccgag gacucccacu cguucacacg   2820
cuuaucacug ucuccaagau ucuccaccau aagaugcuuc auagcguacu gcaggcuccc   2880
auguccaccu ugaauacgcu caaggcggga gguauuuuga aucgcuucuc aaaagauauu   2940
gcaauuuugg augaccuucu gccccugacg aucuucgacu ucauccaguu guugcugauc   3000
gugauugggg cuauugcagu agucgcuguc cuccagccuu acauuuuugu cgcgaccguu   3060
ccggugaucg uggcguuuau caugcugcgg gccuauuucu ugcagacguc acagcagcuu   3120
aagcaacugg agucugaagg gaggucgccu aucuuuacgc aucuugugac caguuugaag   3180
ggauugugga cguugcgcgc cuuuggcagg cagcccuacu uugaaacacu guuccacaaa   3240
gcgcugaauc uccauacggc aaauugguuu uuguauuuga guacccuccg augguuucag   3300
augcgcauug agaugauuuu ugugaucuuc uuuaucgcgg ugacuuuuau cuccaucuug   3360
accacgggag agggcgaggg acgggucggu auuauccuga cacucgccau gaacauuaug   3420
agcacuuugc agugggcagu gaacagcucg auugaugugg auagccugau gagguccguu   3480
ucgaggggucu uuaaguucau cgacaugccg acggagggaa agcccacaaa aaguacgaaa   3540
cccuauaaga augggcaauu gaguaaggua augaucaucg agaacaguca cgugaagaag   3600
gaugacaucu ggccuagcgg gggucagaug accgugaagg accugacggc aaaauacacc   3660
gagggaggga acgcaauccu ugaaaacauc ucguucagca uuagccccgg ucagcgugug   3720
ggguugcucg ggaggaccgg gucaggaaaa ucgacguugc ugucggccuu cuugagacuu   3780
cugaauacag agggugagau ccagaucgac ggcguuucgu gggauagcau caccuugcag   3840
caguggcgga aagcguuugg aguaaucccc caaaaggucu uuaucuuuag cggaaccuuc   3900
```

-continued

```
cgaaagaauc ucgauccuua ugaacagugg ucagaucaag agauuuggaa agucgcggac   3960

gagguuggcc uucggagugu aaucgagcag uuuccgggaa aacucgacuu uguccuugua   4020

gaugggggau gcguccuguc gcaugggcac aagcagcuca ugugccuggc gcgauccguc   4080

cucucuaaag cgaaaauucu ucucuuggau gaaccuucgg cccaucugga cccgguaacg   4140

uaucagauca ucagaaggac acuuaagcag gcguuugccg acugcacggu gauucucugu   4200

gagcaucgua ucgaggccau gcucgaaugc cagcaauuuc uugucaucga agagaauaag   4260

guccgccagu acgacuccau ccagaagcug cuuaaugaga gaucauuguu ccggcaggcg   4320

auuucaccau ccgauagggu gaaacuuuuu ccacacagaa auucgucgaa gugcaagucc   4380

aaaccgcaga ucgcggccuu gaaagaagag acugaagaag aaguucaaga cacgcgucuu   4440

uaa                                                                  4443
```

<210> SEQ ID NO 3
<211> LENGTH: 4443
<212> TYPE: RNA
<213> ORGANISM: Artificial Sequence
<220> FEATURE:
<223> OTHER INFORMATION: chemically synthesized oligonucleotide

<400> SEQUENCE: 3

```
augcagcggu ccuagcucga aaaggccagu gucgugucca aacucuucuu cucauggacu     60

cggccuaucc uuagaaaggg guaucggcag aggcuugagu ugucugacau cuaccaguga    120

cccucgguag auucggcgga uaaccucucg gagaagcucg aacgggaaug ggaccgcgaa    180

cucgcgucua agaaaaaccc gaagcucauc aacgcacuga gaaggugcuu cuucuggcgg    240

uucauguucu acgguaucuu cuuguaucuc ggggagguca caaaagcagu ccaaccccug    300

uguugggguc gcauuaucgc cucguacgac cccgauaaca aagaagaacg gagcaucgcg    360

aucuaccucg ggaucggacu guguuugcuu uucaucguca gaacacuuuu guugcaucca    420

gcaaucuucg gccuccauca caucgguaug cagaugcgaa ucgcuauguu uagcuugauc    480

uacaaaaaga cacugaaacu cucgucgcgg guguuggaua agauuuccau cggucaguug    540

guguccccugc uuaguaauaa ccucaacaaa uucgaugagg gacuggcgcu ggcacauuuc    600

guguggauug ccccguugca agucgcccuu uugaugggcc uuauuuggga gcuguugcag    660

gcaucugccu uuguggccu gggauuucug auuguguugg cauuguuuca ggcugggcuu    720

gggcggauga ugaugaagua ucgcgaccag agagcgggua aaaucucgga aagacucguc    780

aucacuucgg aaaugaucga aaacauccag ucggucaaag ccuauugcug ggaagaagcu    840

auggagaaga ugauugaaaa ccuccgccaa acugagcuga aacugacccg caaggcggcg    900

uauguccggu auuucaauuc gucagcguuc uucuuuuccg gguucuucgu ugucuuucuc    960

ucgguuuugc cuuaugccuu gauuaagggg auuauccucc gcaagauuuu caccacgauu   1020

ucguucugca uuguauugcg cauggcagug acacggcaau uuccgugggc cgugcagaca   1080

ugguaugacu cgcuuggagc gaucaacaaa auccaagacu ucuugcaaaa gcaagaguac   1140

aagacccugg aguacaaucu uacuacuacg gagguaguaa uggagaaugu gacggcuuuu   1200

ugggaagagg guuuuggaga acuguuugag aaagcaaagc agaauaacaa caaccgcaag   1260

accucaaaug gggacgauuc ccuguuuuuc ucgaacuucu cccugcucgg aacacccgug   1320

uugaaggaca ucaauuucaa gauugagagg ggacagcuuc ucgcgguagc gggaagcacu   1380

ggugcgggaa aaacuagccu cuugauggug auuauggggg agcuugagcc cagcgagggg   1440

aagauuaaac acuccgggcg uaucucauuc uguagccagu uuucauggau caugcccgga   1500
```

```
accauuaaag agaacaucau uuucggagua uccuaugaug aguaccgaua cagaucgguc   1560
auuaaggcgu gccaguugga agaggacauu ucuaaguucg ccgagaagga uaacaucguc   1620
uugggagaag gggguauuac auugucggga gggcagcgag cgcggaucag ccucgcgaga   1680
gcgguauaca aagaugcaga uuuguaucug cuugauucac cguuuggaua ccucgacgua   1740
uugacagaaa aagaaaucuu cgagucgugc guguguaaac uuauggcuaa uaagacgaga   1800
auccuggug a caucaaaaau ggaacaccuu aagaaggcgg acaagauccu gauccuccac   1860
gaaggaucgu ccuacuuuua cggcacuuuc ucagaguugc aaaacuugca gccggacuuc   1920
ucaagcaaac ucauggggug ugacucauuc gaccaguuca gcgcggaacg gcggaacucg   1980
aucuugacgg aaacgcugca ccgauucucg cuugagggug augccccggu aucguggacc   2040
gagacaaaga agcagucguu uaagcagaca ggagaauuug gugagaaaag aaagaacagu   2100
aucuugaauc cuauuaacuc aauucgcaag uucucaaucg uccagaaaac uccacugcag   2160
augaauggaa uugaagagga uucggacgaa ccccuggagc gcaggcuuag ccucgugccg   2220
gauucagagc aaggggaggc cauucuuccc cggauuucgg ugauuucaac cggaccuaca   2280
cuucaggcga ggcgaaggca auccgugcuc aaccucauga cgcauucggu aaaccagggg   2340
caaaacauuc accgcaaaac gacggccuca acgagaaaag ugucacuugc accccaggcg   2400
aauuugacug aacucgacau cuacagccgu aggcuuucgc aagaaaccgg acuugagauc   2460
agcgaagaaa ucaaugaaga agauuugaaa gaguguuucu uugaugacau ggaaucaauc   2520
ccagcgguga caacguggaa cacauacuug cguuacauca cggugcacaa guccuugauu   2580
uucguccuca ucugguguc u cgugaucuuu cucgcugagg ucgcagcguc acuuguggu c   2640
cucuggcugc uugguaauac gcccuugcaa gacaaaggca auucuacaca cucaagaaac   2700
aauuccuaug ccgugauuau cacuucuaca agcucguauu acguguuuua caucuacgua   2760
ggaguggccg acacucugcu cgcgaugggu uucuucccgag gacucccacu cguucacacg   2820
cuuaucacug ucuccaagau ucuccaccau aagaugcuuc auagcguacu gcaggcuccc   2880
auguccaccu ugaauacgcu caaggcggga gguauuuuga aucgcuucuc aaaagauauu   2940
gcaauuuugg augaccuucu gccccugacg aucuucgacu ucauccaguu guugcugauc   3000
gugauugggg cuauugcagu agucgcuguc cuccagccuu acauuuuugu cgcgaccguu   3060
ccggugaucg uggcguuuau caugcugcgg gccuauuucu ugcagacguc acagcagcuu   3120
aagcaacugg agucugaagg gaggucgccu aucuuuacgc aucuugugac caguuugaag   3180
ggauugugga cguugcgcgc cuuuggcagg cagcccuacu uugaaacacu guuccacaaa   3240
gcgcugaauc uccauacggc aaauugguuu uuguauuuga guacccuccg augguuucag   3300
augcgcauug agaugauuuu ugugaucuuc uuuaucgcgg ugacuuuuau cuccaucuug   3360
accacgggag agggcgaggg acgggucggu auuauccuga cacucgccau gaacauuaug   3420
agcacuuugc agugggcagu gaacagcucg auugaugugg auagccugau gagguccguu   3480
ucgagggucu uuaaguucau cgacaugccg acggagggaa agcccacaaa aaguacgaaa   3540
cccuauaaga augggcaauu gaguaaggua augaucaucg agaacaguca cgugaagaag   3600
gaugacaucu ggccuagcgg gggucagaug accgugaagg accugacggc aaaauacacc   3660
gagggaggga acgcaauccu ugaaaacauc ucguucagca uuagccccgg ucagcgugug   3720
ggguugcucg ggaggaccgg gucaggaaaa ucgacguugc ugucggccuu cuugagacuu   3780
cugaauacag agggugagau ccagaucgac ggcguuucgu gggauagcau caccuugcag   3840
```

-continued

```
caguggcgga aagcguuugg aguaaucccc caaaaggucu uuaucuuuag cggaaccuuc   3900

cgaaagaauc ucgauccuua ugaacagugg ucagaucaag agauuuggaa agucgcggac   3960

gagguuggcc uucggagugu aaucgagcag uuuccgggaa aacucgacuu uguccuugua   4020

gauggggau gcguccuguc gcaugggcac aagcagcuca ugugccuggc gcgauccguc    4080

cucucuaaag cgaaaauucu ucucuuggau gaaccuucgg cccaucugga cccgguaacg   4140

uaucagauca ucagaaggac acuuaagcag gcguuugccg acugcacggu gauucucugu   4200

gagcaucgua ucgaggccau gcucgaaugc cagcaauuuc uugucaucga agagaauaag   4260

guccgccagu acgacuccau ccagaagcug cuuaaugaga gaucauuguu ccggcaggcg   4320

auuucaccau ccgauagggu gaaacuuuuu ccacacagaa auucgucgaa gugcaagucc   4380

aaaccgcaga ucgcggccuu gaaagaagag acugaagaag aaguucaaga cacgcgucuu   4440

uaa                                                                 4443


<210> SEQ ID NO 4
<211> LENGTH: 1480
<212> TYPE: PRT
<213> ORGANISM: Homo sapiens

<400> SEQUENCE: 4

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
```

```
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685
```

-continued

```
Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095
```

-continued

```
Phe Gln  Met Arg Ile Glu Met  Ile Phe Val Ile Phe  Phe Ile Ala
    1100                 1105                 1110

Val Thr  Phe Ile Ser Ile Leu  Thr Thr Gly Glu Gly  Glu Gly Arg
    1115                 1120                 1125

Val Gly  Ile Ile Leu Thr Leu  Ala Met Asn Ile Met  Ser Thr Leu
    1130                 1135                 1140

Gln Trp  Ala Val Asn Ser Ser  Ile Asp Val Asp Ser  Leu Met Arg
    1145                 1150                 1155

Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 5
<211> LENGTH: 140
<212> TYPE: RNA
<213> ORGANISM: Artificial Sequence
<220> FEATURE:
<223> OTHER INFORMATION: chemically synthesized oligonucleotide

<400> SEQUENCE: 5
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 6
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 6
cggguggcau cccugugacc ccuccccagu gccucuccug gcccuggaag uugccacucc 60
agugcccacc agccuugucc uaauaaaauu aaguugcauc aagcu 105

<210> SEQ ID NO 7
<211> LENGTH: 105
<212> TYPE: RNA
<213> ORGANISM: Artificial Sequence
<220> FEATURE:
<223> OTHER INFORMATION: chemically synthesized oligonucleotide

<400> SEQUENCE: 7
ggguggcauc ccugugaccc cuccccagug ccucuccugg cccuggaagu ugccacucca 60
gugcccacca gccuuguccu aauaaaauua aguugcauca aagcu 105

<210> SEQ ID NO 8
<211> LENGTH: 4688
<212> TYPE: RNA
<213> ORGANISM: Artificial Sequence
<220> FEATURE:
<223> OTHER INFORMATION: chemically synthesized oligonucleotide

<400> SEQUENCE: 8
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180
agcucuucuu cucguggacu agacccaucc ugagaaaggg guacagacag cgcuuggagc 240
uguccgauau cuaucaaauc ccuuccgugg acuccgcgga caaccugucc gagaagcucg 300
agagagaaug ggacagagaa cucgccucaa agaagaaccc gaagcugauu aaugcgcuua 360
ggcggugcuu uuucuggcgg uucauguucu acggcaucuu ccucuaccug ggagagguca 420
ccaaggccgu gcagccccug uugcugggac ggauuauugc cuccuacgac cccgacaaca 480
aggaagaaag aagcaucgcu aucuacuugg gcaucggucu gugccugcuu uucaucgucc 540
ggacccucuu guugcauccu gcuauuuucg gccugcauca cauuggcaug cagaugagaa 600
uugccauguu uucccugauc uacaagaaaa cucugaagcu cucgagccgc gugcuugaca 660
agauuuccau cggccagcuc guguccccugc ucuccaacaa ucugaacaag uucgacgagg 720
gccucgcccu ggcccacuuc guguggaucg ccccucugca aguggcgcuu cugaugggcc 780

-continued ugaucuggga gcugcugcaa gccucggcau ucugugggcu uggauuccug aucgugcugg 840
cacuguucca ggccggacug gggcggauga ugaugaagua cagggaccag agagccggaa 900
agauuuccga acggcuggug aucacuucgg aaaugaucga aaacauccag ucagugaagg 960
ccuacugcug ggaagaggcc auggaaaaga ugauugaaaa ccuccggcaa accgagcuga 1020
agcugacccg caaggccgcu uacgugcgcu auuucaacuc guccgcuuuc uucuucuccg 1080
gguucuucgu gguguuucuc uccgugcucc ccuacgcccu gauuaaggga aucauccuca 1140
ggaagaucuu caccaccauu uccuucugua ucgugcuccg cauggccgug acccggcagu 1200
ucccaugggc cgugcagacu ugguacgacu cccugggagc cauuaacaag auccaggacu 1260
uccuucaaaa gcaggaguac aagacccucg aguacaaccu gacuacuacc gaggucguga 1320
uggaaaacgu caccgccuuu ugggaggagg gauuuggcga acuguucgag aaggccaagc 1380
agaacaacaa caaccgcaag accucgaacg gugacgacuc ccucuucuuu ucaaacuuca 1440
gccugcucgg gacgcccgug cugaaggaca uuaacuucaa gaucgaaaga ggacagcucc 1500
uggcgguggc cggaucgacc ggagccggaa agacuucccu gcugauggug aucaugggag 1560
agcuugaacc uagcgaggga aagaucaagc acuccggccg caucagcuuc uguagccagu 1620
uuuccuggau caugcccgga accauuaagg aaaacaucau cuucggcgug uccuacgaug 1680
aauaccgcua ccgguccgug aucaaagccu gccagcugga agaggauauu ucaaaguucg 1740
cggagaaaga uaacaucgug cugggcgaag gggguauuac cuugucgggg ggccagcggg 1800
cuagaaucuc gcuggccaga gccguguaua aggacgccga ccuguaucuc cuggacuccc 1860
ccuucggaua ccuggacguc cugaccgaaa aggagaucuu cgaaucgugc gugugcaagc 1920
ugauggcuaa caagacucgc auccucguga ccuccaaaau ggagcaccug aagaaggcag 1980
acaagauucu gauucugcau gaggggucc u ccuacuuuua cggcaccuuc ucggaguugc 2040
agaacuugca gcccgacuuc ucaucgaagc ugaugggguug cgacagcuuc gaccaguucu 2100
ccgccgaaag aaggaacucg auccugacgg aaaccuugca ccgcuucucu uuggaaggcg 2160
acgccccugu gucauggacc gagacuaaga agcagagcuu caagcagacc ggggaauucg 2220
gcgaaaagag gaagaacagc aucuugaacc ccauuaacuc cauccgcaag uucucaaucg 2280
ugcaaaagac gccacugcag augaacggca uugaggagga cuccgacgaa ccccuugaga 2340
ggcgccuguc ccuggugccg gacagcgagc agggagaagc cauccugccu cggauuuccg 2400
ugaucuccac ugguccgacg cuccaagccc ggcggcggca guccgugcug aaccugauga 2460
cccacagcgu gaaccagggc caaaacauuc accgcaagac uaccgcaucc acccggaaag 2520
ugucccuggc accucaagcg aaucuuaccg agcucgacau cuacucccgg agacugucgc 2580
aggaaaccgg gcucgaaauu uccgaagaaa ucaacgagga ggaucugaaa gagugcuucu 2640
ucgacgauau ggagucgaua cccgccguga cgacuuggaa cacuuaucug cgguacauca 2700
cugugcacaa gucauugauc uucgugcuga uuuggugccu ggugauuuuc cuggccgagg 2760
ucgcggccuc acugguggug cucuggcugu ugggaaacac gccucugcaa gacaagggaa 2820
acuccacgca cucgagaaac aacagcuaug ccgugauuau cacuuccacc uccucuuauu 2880
acguguucua caucuacguc ggaguggcgg auacccugcu cgcgaugggu uucuucagag 2940
gacugccgcu gguccacacc uugaucaccg ucagcaagau ucuucaccac aagauguugc 3000
auagcgugcu gcaggccccc auguccaccc ucaacacucu gaaggccgga ggcauucuga 3060
acagauucuc caaggacauc gcuauccugg acgaucuccu gccgcuuacc aucuuugacu 3120
ucauccagcu gcugcugauc gugauuggag caaucgcagu gguggcggug cugcagccuu 3180
acauuuucgu ggccacugug ccggucauug uggcguucau caugcugcgg gccuacuucc 3240
uccaaaccag ccagcagcug aagcaacugg aauccgaggg acgaucccc aucuucacuc 3300 accuugugac gucguugaag ggacugugga cccuccgggc uuucggacgg cagcccuacu 3360
ucgaaacccu cuuccacaag gcccugaacc uccacaccgc caauugguuc cuguaccugu 3420
ccacccugcg gugguuccag augcgcaucg agaugauuuu cgucaucuuc uucaucgcgg 3480
ucacauucau cagcauccug acuaccggag agggagaggg acgggucgga auaauccuga 3540
cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780
accugaccgc aaaguacacc gagggaggaa acgccauucu cgaaaacauc agcuucucca 3840
uuucgccggg acagcggguc ggccuucucg ggcggaccgg uuccgggaag ucaacucugc 3900
ugucggcuuu ccuccggcug cugaauaccg agggggaaau ccaaauugac ggcgugucuu 3960
gggauuccau uacucugcag caguggcgga aggccuucgg cgugaucccc cagaaggugu 4020
ucaucuucuc ggguaccuuc cggaagaacc uggauccuua cgagcagugg agcgaccaag 4080
aaaucuggaa ggucgccgac gaggucggcc ugcgcuccgu gauugaacaa uuuccuggaa 4140
agcuggacuu cgugcucguc gacgggggau guguccuguc gcacggacau aagcagcuca 4200
ugugccucgc acgguccgug cucuccaagg ccaagauucu gcugcuggac gaaccuucgg 4260
cccaccugga uccggucacc uaccagauca ucaggaggac ccugaagcag gccuuugccg 4320
auugcaccgu gauucucugc gagcaccgca ucgaggccau gcuggagugc cagcaguucc 4380
uggucaucga ggagaacaag guccgccaau acgacuccau ucaaaagcuc cucaacgagc 4440
ggucgcuguu cagacaagcu auuucaccgu ccgauagagu gaagcucuuc ccgcaucgga 4500
acagcucaaa gugcaaaucg aagccgcaga ucgcagccuu gaaggaagag acugaggaag 4560
aggugcagga cacccggcuu uaacgggugg caucccugug accccucccc agugccucuc 4620
cuggcccugg aaguugccac uccagugccc accagccuug uccuaauaaa auuaaguugc 4680
aucaagcu 4688

<210> SEQ ID NO 9
<211> LENGTH: 4688
<212> TYPE: RNA
<213> ORGANISM: Artificial Sequence
<220> FEATURE:
<223> OTHER INFORMATION: chemically synthesized oligonucleotide

<400> SEQUENCE: 9
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180
agcucuucuu cucguggacu agacccaucc ugagaaaggg guacagacag cgcuuggagc 240
uguccgauau cuaucaaauc ccuuccgugg acuccgcgga caaccugucc gagaagcucg 300
agagagaaug ggacagagaa cucgccucaa agaagaaccc gaagcugauu aaugcgcuua 360
ggcggugcuu uuucuggcgg uucauguucu acggcaucuu ccucuaccug ggagagguca 420
ccaaggccgu gcagccccug uugcugggac ggauuauugc cuccuacgac cccgacaaca 480

-continued

```
aggaagaaag aagcaucgcu aucuacuugg gcaucggucu gugccugcuu uucaucgucc    540
ggacccucuu guugcauccu gcuauuuucg gccugcauca cauuggcaug cagaugagaa    600
uugccauguu uucccugauc uacaagaaaa cucugaagcu cucgagccgc gugcuugaca    660
agauuuccau cggccagcuc gugucccugc ucuccaacaa ucugaacaag uucgacgagg    720
gccucgcccu ggcccacuuc guguggaucg ccccucugca aguggcgcuu cugaugggcc    780
ugaucuggga gcugcugcaa gccucggcau ucugugggcu uggauuccug aucgugcugg    840
cacuguucca ggccggacug ggcggaugua ugaugaagua cagggaccag agagccggaa    900
agauuuccga acggcuggug aucacuucgg aaaugaucga aaacauccag ucagugaagg    960
ccuacugcug ggaagaggcc auggaaaaga ugauugaaaa ccuccggcaa accgagcuga   1020
agcugacccg caaggccgcu uacgugcgcu auuucaacuc guccgcuuuc uucuucuccg   1080
gguucuucgu gguguuucuc uccgugcucc ccuacgcccu gauuaaggga aucauccuca   1140
ggaagaucuu caccaccauu uccuucugua ucgugcuccg cauggccgug acccggcagu   1200
ucccaugggc cgugcagacu ugguacgacu cccugggagc cauuaacaag auccaggacu   1260
uccuucaaaa gcaggaguac aagacccucg aguacaaccu gacuacuacc gaggucguga   1320
uggaaaacgu caccgccuuu ugggaggagg gauuuggcga acuguucgag aaggccaagc   1380
agaacaacaa caaccgcaag accucgaacg gugacgacuc ccucuucuuu ucaaacuuca   1440
gccugcucgg gacgcccgug cugaaggaca uuaacuucaa gaucgaaaga ggacagcucc   1500
uggcgguggc cggaucgacc ggagccggaa agacuucccu gcugauggug aucaugggag   1560
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu ucaaaguucg   1740
cggagaaaga uaacaucgug cugggcgaag gggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggaccu ccuacuuuua cggcaccuuc ucggaguugc   2040
agaacuugca gcccgacuuc ucaucgaagc ugauggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
ugucccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acuggugguc cucuggcugu ugggaaacac gccucugcaa gacaagggaa   2820
acuccacgca cucgagaaac aacagcuaug ccgugauuau cacuuccacc uccucuuauu   2880
```

acguguucua caucuacguc ggaguggcgg auacccugcu cgcgaugggu uucuucagag 2940
gacugccgcu gguccacacc uugaucaccg ucagcaagau ucuucaccac aagauguugc 3000
auagcgugcu gcaggccccc auguccaccc ucaacacucu gaaggccgga ggcauucuga 3060
acagauucuc caaggacauc gcuauccugg acgaucuccu gccgcuuacc aucuuugacu 3120
ucauccagcu gcugcugauc gugauuggag caaucgcagu gguggcggug cugcagccuu 3180
acauuuucgu ggccacugug ccggucauug uggcguucau caugcugcgg gccuacuucc 3240
uccaaaccag ccagcagcug aagcaacugg aauccgaggg acgauccccc aucuucacuc 3300
accuugugac gucguugaag ggacugugga cccuccgggc uuucggacgg cagcccuacu 3360
ucgaaacccu cuuccacaag gcccugaacc uccacaccgc caauugguuc cuguaccugu 3420
ccacccugcg gugguuccag augcgcaucg agaugauuuu cgucaucuuc uucaucgcgg 3480
ucacauucau cagcauccug acuaccggag agggagaggg acgggucgga auaaauccuga 3540 cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780
accugaccgc aaaguacacc gagggaggaa acgccauucu cgaaaacauc agcuucucca 3840
uuucgccggg acagcggguc ggccuucucg ggcggaccgg uuccgggaag ucaacucugc 3900
ugucggcuuu ccuccggcug cugaauaccg agggggaaau ccaaauugac ggcgugucuu 3960
gggauuccau uacucugcag caguggcgga aggccuucgg cgugaucccc cagaaggugu 4020
ucaucuucuc ggguaccuuc cggaagaacc uggauccuua cgagcagugg agcgaccaag 4080
aaaucuggaa ggucgccgac gaggucggcc ugcgcuccgu gauugaacaa uuuccuggaa 4140
agcuggacuu cgugcucguc gacgggggau guguccuguc gcacggacau aagcagcuca 4200
ugugccucgc acgguccgug cucuccaagg ccaagauucu gcugcuggac gaaccuucgg 4260
cccaccugga uccggucacc uaccagauca ucaggaggac ccugaagcag gccuuugccg 4320
auugcaccgu gauucucugc gagcaccgca ucgaggccau gcuggagugc cagcaguucc 4380
uggucaucga ggagaacaag guccgccaau acgacuccau ucaaaagcuc cucaacgagc 4440
ggucgcuguu cagacaagcu auuucaccgu ccgauagagu gaagcucuuc ccgcaucgga 4500
acagcucaaa gugcaaaucg aagccgcaga ucgcagccuu gaaggaagag acugaggaag 4560
aggugcagga cacccggcuu uaagggugge aucccuguga ccccuccccca gugccucucc 4620 uggcccugga aguugccacu ccagugccca ccagccuugu ccuaauaaaa uuaaguugca 4680
ucaaagcu 4688

<210> SEQ ID NO 10
<211> LENGTH: 4688
<212> TYPE: RNA
<213> ORGANISM: Artificial Sequence
<220> FEATURE:
<223> OTHER INFORMATION: chemically synthesized oligonucleotide

<400> SEQUENCE: 10
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcagcggu ccccgcucga aaaggccagu gucgugucca 180

-continued aacucuucuu cucauggacu cggccuaucc uuagaaaggg guaucggcag aggcuugagu 240
ugucugacau cuaccagauc cccucgguag auucggcgga uaaccucucg gagaagcucg 300
aacgggaaug ggaccgcgaa cucgcgucua agaaaaaccc gaagcucauc aacgcacuga 360
gaaggugcuu cuucuggcgg uucauguucu acgguaucuu cuuguaucuc ggggagguca 420
caaaagcagu ccaaccccug uuguugggucc gcauuaucgc cucguacgac cccgauaaca 480
aagaagaacg gagcaucgcg aucuaccucg ggaucggacu guguuugcuu uucaucguca 540
gaacacuuuu guugcaucca gcaaucuucg gccuccauca caucgguaug cagaugcgaa 600
ucgcuauguu uagcuugauc uacaaaaaga cacugaaacu cucgucgcgg guguuggaua 660
agauuuccau cggucaguug guguccccugc uuaguaauaa ccucaacaaa uucgaugagg 720
gacuggcgcu ggcacauuuc guguggauug ccccguugca agucgcccuu uugaugggcc 780
uuauuuggga gcuguugcag gcaucugccu uuguggccu gggauuucug auuguguugg 840
cauuguuuca ggcugggcuu gggcggauga ugaugaagua ucgcgaccag agagcgggua 900
aaaucucgga aagacucguc aucacuucgg aaaugaucga aaacauccag ucggucaaag 960
ccuauugcug ggaagaagcu auggagaaga ugauugaaaa ccuccgccaa acugagcuga 1020
aacugacccg caaggcggcg uauguccggu auuucaauuc gucagcguuc uucuuuuccg 1080
gguucuucgu ugucuuucuc ucgguuuugc cuuaugccuu gauuaagggg auuauccucc 1140
gcaagauuuu caccacgauu ucguucugca uuguauugcg cauggcagug acacggcaau 1200
uuccgugggc cgugcagaca ugguaugacu cgcuuggagc gaucaacaaa auccaagacu 1260
ucuugcaaaa gcaagaguac aagacccugg aguacaaucu uacuacuacg gagguaguaa 1320
uggagaaugu gacggcuuuu ugggaagagg guuuuggaga acuguuugag aaagcaaagc 1380
agaauaacaa caaccgcaag accucaaaug ggacgauuc ccuguuuuuc ucgaacuucu 1440
cccugcucgg aacacccgug uugaaggaca ucaauuucaa gauugagagg ggacagcuuc 1500
ucgcgguagc gggaagcacu ggugcgggaa aaacuagccu cuugauggug auuauggggg 1560
agcuugagcc cagcgagggg aagauuaaac acuccgggcg uaucucauuc uguagccagu 1620
uuucauggau caugcccgga accauuaaag agaacaucau uuucggagua uccuaugaug 1680
aguaccgaua cagaucgguc auuaaggcgu gccaguugga agaggacauu ucuaaguucg 1740
ccgagaagga uaacaucguc uugggagaag gggguauuac auugucggga gggcagcgag 1800
cgcggaucag ccucgcgaga gcgguauaca aagaugcaga uuuguaucug cuugauucac 1860
cguuuggaua ccucgacgua uugacagaaa aagaaaucuu cgagucgugc guguguaaac 1920
uuauggcuaa uaagacgaga auccugguga caucaaaaau ggaacaccuu aagaaggcgg 1980
acaagauccu gauccuccac gaaggaucgu ccuacuuuua cggcacuuuc ucagaguugc 2040
aaaacuugca gccggacuuc ucaagcaaac ucauggggug ugacucauuc gaccaguuca 2100
gcgcggaacg gcggaacucg aucuugacgg aaacgcugca ccgauucucg cuugagggug 2160
augccccggu aucguggacc gagacaaaga agcagucguu uaagcagaca ggagaauuug 2220
gugagaaaag aaagaacagu aucuugaauc cuauuaacuc aauucgcaag uucucaaucg 2280
uccagaaaac uccacugcag augaauggaa uugaagagga uucggacgaa ccccuggagc 2340
gcaggcuuag ccucgugccg gauucagagc aaggggaggc cauucuuccc cggauuucgg 2400
ugauuucaac cggaccuaca cuucaggcga ggcgaaggca auccgugcuc aaccucauga 2460
cgcauucggu aaaccagggg caaaacauuc accgcaaaac gacggccuca acgagaaaag 2520
ugucacuugc accccaggcg aauuugacug aacucgacau cuacagccgu aggcuuucgc 2580

-continued

```
aagaaaccgg acuugagauc agcgaagaaa ucaaugaaga agauuugaaa gaguguuucu   2640
uugaugacau ggaaucaauc ccagcgguga caacguggaa cacauacuug cguuacauca   2700
cggugcacaa guccuugauu uucguccuca ucuggugucu cgugaucuuu cucgcugagg   2760
ucgcagcguc acuuguggue cucuggcugc uugguaauac gcccuugcaa gacaaaggca   2820
auucuacaca cucaagaaac aauuccuaug ccgugauuau cacuucuaca agcucguauu   2880
acguguuuua caucuacgua ggaguggccg acacucugcu cgcgaugggu uucuuccgag   2940
gacucccacu cguucacacg cuuaucacug ucuccaagau ucuccaccau aagaugcuuc   3000
auagcguacu gcaggcuccc auguccaccu ugaauacgcu caaggcggga gguauuuuga   3060
aucgcuucuc aaaagauauu gcaauuuugg augaccuucu gccccugacg aucuucgacu   3120
ucauccaguu guugcugauc gugauugggg cuauugcagu agucgcuguc cuccagccuu   3180
acauuuuugu cgcgaccguu ccggugaucg uggcguuuau caugcugcgg gccuauuucu   3240
ugcagacguc acagcagcuu aagcaacugg agucugaagg gaggucgccu aucuuuacgc   3300
aucuugugac caguuugaag ggauugugga cguugcgcgc cuuuggcagg cagcccuacu   3360
uugaaacacu guuccacaaa gcgcugaauc uccauacggc aaauugguuu uuguauuuga   3420
guacccuccg augguuucag augcgcauug agaugauuuu ugugaucuuc uuuaucgcgg   3480
ugacuuuuau cuccaucuug accacgggag agggcgaggg acgggucggu auuauccuga   3540
cacucgccau gaacauuaug agcacuuugc agugggcagu gaacagcucg auugaugugg   3600
auagccugau gagguccguu ucgagggucu uuaaguucau cgacaugccg acggagggaa   3660
agcccacaaa aaguacgaaa cccuauaaga augggcaauu gaguaaggua augaucaucg   3720
agaacaguca cgugaagaag gaugacaucu ggccuagcgg gggucagaug accgugaagg   3780
accugacggc aaaauacacc gagggaggga acgcaauccu ugaaaacauc ucguucagca   3840
uuagccccgg ucagcgugug ggguugcucg ggaggaccgg gucaggaaaa ucgacguugc   3900
ugucggccuu cuugagacuu cugaauacag agggugagau ccagaucgac ggcguuucgu   3960
gggauagcau caccuugcag caguggcgga aagcguuugg aguaaucccc caaaaggucu   4020
uuaucuuuag cggaaccuuc cgaaagaauc ucgauccuua ugaacagugg ucagaucaag   4080
agauuuggaa agucgcggac gagguuggcc uucggagugu aaucgagcag uuuccgggaa   4140
aacucgacuu uguccuugua gaugggggau gcguccuguc gcaugggcac aagcagcuca   4200
ugugccuggc gcgauccguc cucucuaaag cgaaaauucu ucucuuggau gaaccuucgg   4260
cccaucugga cccgguaacg uaucagauca ucagaaggac acuuaagcag gcguuugccg   4320
acugcacggu gauucucugu gagcaucgua ucgaggccau gcucgaaugc cagcaauuuc   4380
uugucaucga agagaauaag guccgccagu acgacuccau ccagaagcug cuuaaugaga   4440
gaucauuguu ccggcaggcg auuucaccau ccgauagggu gaaacuuuuu ccacacagaa   4500
auucgucgaa gugcaagucc aaaccgcaga ucgcggccuu gaaagaagag acugaagaag   4560
aaguucaaga cacgcgucuu uaacgggugg caucccugug accccucccc agugccucuc   4620
cuggcccugg aaguugccac uccagugccc accagccuug uccuaauaaa auuaaguugc   4680
aucaagcu                                                            4688
```

<210> SEQ ID NO 11
<211> LENGTH: 4688
<212> TYPE: RNA
<213> ORGANISM: Artificial Sequence
<220> FEATURE:

<223> OTHER INFORMATION: chemically synthesized oligonucleotide

<400> SEQUENCE: 11

```
ggacagaucg ccuggagacg ccauccacgc uguuuugacc uccauagaag acaccgggac     60
cgauccagcc uccgcggccg ggaacggugc auuggaacgc ggauuccccg ugccaagagu    120
gacucaccgu ccuugacacg augcagcggu ccccgcucga aaaggccagu gucgugucca    180
aacucuucuu cucauggacu cggccuaucc uuagaaaggg guaucggcag aggcuugagu    240
ugucugacau cuaccagauc cccucgguag auucggcgga uaaccucucg gagaagcucg    300
aacgggaaug ggaccgcgaa cucgcgucua agaaaaaccc gaagcucauc aacgcacuga    360
gaaggugcuu cuucuggcgg uucauguucu acgguaucuu cuuguaucuc ggggagguca    420
caaaagcagu ccaaccccug uuguugggguc gcauuaucgc cucguacgac cccgauaaca    480
aagaagaacg gagcaucgcg aucuaccucg ggaucggacu guguuugcuu uucaucguca    540
gaacacuuuu guugcaucca gcaaucuucg gccuccauca caucgguaug cagaugcgaa    600
ucgcuauguu uagcuugauc uacaaaaaga cacugaaacu cucgucgcgg guguuggaua    660
agauuuccau cggucaguug guguccougc uuaguaauaa ccucaacaaa uucgaugagg    720
gacuggcgcu ggcacauuuc guguggauug ccccguugca agucgcccuu uugaugggcc    780
uuauuuggga gcuguugcag gcaucugccu uuguggccu gggauuucug auuguguugg    840
cauuguuuca ggcugggcuu gggcggauga ugaugaagua ucgcgaccag agagcgggua    900
aaaucucgga aagacucguc aucacuucgg aaaugaucga aaacauccag ucggucaaag    960
ccuauugcug ggaagaagcu auggagaaga ugauugaaaa ccuccgccaa acugagcuga   1020
aacugacccg caaggcggcg uauguccggu auuucaauuc gucagcguuc uucuuuuccg   1080
gguucuucgu ugucuuucuc ucgguuuugc cuuaugccuu gauuaagggg auuauccucc   1140
gcaagauuuu caccacgauu ucguucugca uuguauugcg cauggcagug acacggcaau   1200
uuccgugggc cgugcagaca ugguaugacu cgcuuggagc gaucaacaaa auccaagacu   1260
ucuugcaaaa gcaagaguac aagacccugg aguacaaucu uacuacuacg gagguaguaa   1320
uggagaaugu gacggcuuuu ugggaagagg guuuuggaga acuguuugag aaagcaaagc   1380
agaauaacaa caaccgcaag accucaaaug gggacgauuc ccuguuuuuc ucgaacuucu   1440
cccugcucgg aacacccgug uugaaggaca ucaauuucaa gauugagagg ggacagcuuc   1500
ucgcgguagc gggaagcacu ggugcgggaa aaacuagccu cuugauggug auuauggggg   1560
agcuugagcc cagcgagggg aagauuaaac acuccgggcg uaucucauuc uguagccagu   1620
uuucauggau caugcccgga accauuaaag agaacaucau uuucggagua uccuaugaug   1680
aguaccgaua cagaucgguc auuaaggcgu gccaguugga agaggacauu ucuaaguucg   1740
ccgagaagga uaacaucguc uugggagaag gggguauuac auugucggga gggcagcgag   1800
cgcggaucag ccucgcgaga gcgguauaca aagaugcaga uuuguaucug cuugauucac   1860
cguuuggaua ccucgacgua uugacagaaa aagaaaucuu cgagucgugc guguguaaac   1920
uuauggcuaa uaagacgaga auccugguga caucaaaaau ggaacaccuu aagaaggcgg   1980
acaagauccu gauccuccac gaaggaucgu ccuacuuuua cggcacuuuc ucagaguugc   2040
aaaacuugca gccggacuuc ucaagcaaac ucaugggggug ugacucauuc gaccaguuca   2100
gcgcggaacg gcggaacucg aucuugacgg aaacgcugca ccgauucucg cuugagggug   2160
augccccggu aucguggacc gagacaaaga agcagucguu uaagcagaca ggagaauuug   2220
gugagaaaag aaagaacagu aucuugaauc cuauuaacuc aauucgcaag uucucaaucg   2280
```

-continued

```
uccagaaaac uccacugcag augaauggaa uugaagagga uucggacgaa ccccuggagc   2340
gcaggcuuag ccucgugccg gauucagagc aaggggaggc cauucuuccc cggauuucgg   2400
ugauuucaac cggaccuaca cuucaggcga ggcgaaggca auccgugcuc aaccucauga   2460
cgcauucggu aaaccagggg caaaacauuc accgcaaaac gacggccuca acgagaaaag   2520
ugucacuugc accccaggcg aauuugacug aacucgacau cuacagccgu aggcuuucgc   2580
aagaaaccgg acuugagauc agcgaagaaa ucaaugaaga agauuugaaa gaguguuucu   2640
uugaugacau ggaaucaauc ccagcgguga caacguggaa cacauacuug cguuacauca   2700
cggugcacaa guccuugauu uucguccuca ucuggugucu cgugaucuuu cucgcugagg   2760
ucgcagcguc acuuguggguc cucuggcugc uugguaauac gcccuugcaa gacaaaggca   2820
auucuacaca cucaagaaac aauuccuaug ccgugauuau cacuucuaca agcucguauu   2880
acguguuuua caucuacgua ggaguggccg acacucugcu cgcgaugggu uucuuccgag   2940
gacucccacu cguucacacg cuuaucacug ucuccaagau ucuccaccau aagaugcuuc   3000
auagcguacu gcaggcuccc auguccaccu ugaauacgcu caaggcggga gguauuuuga   3060
aucgcuucuc aaaagauauu gcaauuuugg augaccuucu gccccugacg aucuucgacu   3120
ucauccaguu guugcugauc gugauugggg cuauugcagu agucgcuguc cuccagccuu   3180
acauuuuugu cgcgaccguu ccggugaucg uggcguuuau caugcugcgg gccuauuucu   3240
ugcagacguc acagcagcuu aagcaacugg agucugaagg gaggucgccu aucuuuacgc   3300
aucuugugac caguuugaag ggauugugga cguugcgcgc cuuuggcagg cagcccuacu   3360
uugaaacacu guuccacaaa gcgcugaauc uccauacggc aaauugguuu uuguauuuga   3420
guacccuccg augguuucag augcgcauug agaugauuuu ugugaucuuc uuuaucgcgg   3480
ugacuuuuau cuccaucuug accacgggag agggcgaggg acgggucggu auuauccuga   3540
cacucgccau gaacauuaug agcacuuugc agugggcagu gaacagcucg auugaugugg   3600
auagccugau gagguccguu ucgagggucu uuaaguucau cgacaugccg acggagggaa   3660
agcccacaaa aaguacgaaa cccuauaaga augggcaauu gaguaaggua augaucaucg   3720
agaacaguca cgugaagaag gaugacaucu ggccuagcgg gggucagaug accgugaagg   3780
accugacggc aaaauacacc gagggaggga acgcaauccu ugaaaacauc ucguucagca   3840
uuagccccgg ucagcgugug ggguugcucg ggaggaccgg gucaggaaaa ucgacguugc   3900
ugucggccuu cuugagacuu cugaauacag agggugagau ccagaucgac ggcguuucgu   3960
gggauagcau caccuugcag caguggcgga aagcguuugg aguaaucccc caaaaggucu   4020
uuaucuuuag cggaaccuuc cgaaagaauc ucgauccuua ugaacagugg ucagaucaag   4080
agauuuggaa agucgcggac gagguuggcc uucggagugu aaucgagcag uuuccgggaa   4140
aacucgacuu uguccuugua gaugggggau gcguccuguc gcaugggcac aagcagcuca   4200
ugugccuggc gcgauccguc cucucuaaag cgaaaauucu ucucuuggau gaaccuucgg   4260
cccaucugga cccgguaacg uaucagauca ucagaaggac acuuaagcag gcguuugccg   4320
acugcacggu gauucucugu gagcaucgua ucgaggccau gcucgaaugc cagcaauuuc   4380
uugucaucga agagaauaag guccgccagu acgacuccau ccagaagcug cuuaaugaga   4440
gaucauuguu ccggcaggcg auuucaccau ccgauagggu gaaacuuuuu ccacacagaa   4500
auucgucgaa gugcaagucc aaaccgcaga ucgcggccuu gaaagaagag acugaagaag   4560
aaguucaaga cacgcgucuu uaagggguggc aucccuguga ccccuccccca gugccucucc   4620
```

-continued

```
uggcccugga aguugccacu ccagugccca ccagccuugu ccuaauaaaa uuaaguugca    4680

ucaaagcu                                                             4688
```